US012746264B2

(12) United States Patent
Kong

(10) Patent No.: US 12,746,264 B2
(45) Date of Patent: *Sep. 29, 2026

(54) PROBIOTICS COMPOSITIONS AND METHOD OF USING THE SAME TO ENHANCE GROWTH AND SOCIAL FUNCTION IN CHILDREN

(71) Applicant: The General Hospital Corporation, Boston, MA (US)

(72) Inventor: Xue-Jun Kong, Lexington, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/972,671

(22) Filed: Dec. 6, 2024

(65) Prior Publication Data

US 2025/0108077 A1 Apr. 3, 2025

Related U.S. Application Data

(63) Continuation of application No. 18/794,131, filed on Aug. 5, 2024, which is a continuation of application No. 18/267,969, filed as application No. PCT/US2021/064004 on Dec. 17, 2021.

(60) Provisional application No. 63/127,936, filed on Dec. 18, 2020.

(51) Int. Cl.

| | |
|---|---|
| ***A61K 35/747*** | (2015.01) |
| ***A61K 35/741*** | (2015.01) |
| ***A61K 35/742*** | (2015.01) |
| ***A61K 35/745*** | (2015.01) |
| ***A61K 36/064*** | (2006.01) |
| ***A61K 38/27*** | (2006.01) |
| ***A61P 25/28*** | (2006.01) |
| *A61K 35/00* | (2006.01) |

(52) U.S. Cl.

CPC .......... *A61K 35/747* (2013.01); *A61K 35/741* (2013.01); *A61K 35/742* (2013.01); *A61K 35/745* (2013.01); *A61K 36/064* (2013.01); *A61K 38/27* (2013.01); *A61P 25/28* (2018.01); *A61K 2035/115* (2013.01)

(58) Field of Classification Search

CPC .............................. A61K 35/741; A61P 43/00

See application file for complete search history.

(56) References Cited

U.S. PATENT DOCUMENTS

| | | | |
|---|---|---|---|
| 8,513,192 | B2 | 8/2013 | Olsen et al. |
| 2006/0094083 | A1 | 5/2006 | Choi et al. |
| 2006/0105939 | A1 | 5/2006 | Hollander |
| 2014/0079676 | A1 | 3/2014 | Olmstead |
| 2016/0143963 | A1 | 5/2016 | Martorell Guerola et al. |
| 2017/0326200 | A1* | 11/2017 | Danglas .................... A61P 3/04 |
| 2019/0070226 | A1 | 3/2019 | Costa-Mattioli et al. |
| 2020/0121756 | A1 | 4/2020 | Savignac et al. |
| 2020/0157625 | A1 | 5/2020 | Hicks et al. |

FOREIGN PATENT DOCUMENTS

| | | | | |
|---|---|---|---|---|
| CA | 3205469 | A1 | 6/2022 | |
| CN | 112980725 | A1 | 6/2021 | |
| FR | 3093642 | A1 * | 9/2020 | ........... A23L 33/135 |
| WO | WO-2017181158 | A1 * | 10/2017 | .............. A61P 25/28 |
| WO | 2018145294 | A1 | 8/2018 | |
| WO | WO-2019189408 | A1 * | 10/2019 | ........... A23L 33/135 |
| WO | 2022133198 | A1 | 6/2022 | |
| WO | 2022147251 | A1 | 7/2022 | |
| WO | 2023076874 | A1 | 5/2023 | |

OTHER PUBLICATIONS

Ramon-Kruel et al. J. Clin. Med. 2021, 10, 5328, pp. 1-9 (Year: 2021).*

Lalonde et al. Current Neuropharmacology, 2023, 21, pp. 2481-2486 (Year: 2023).*

Loy et al. Childhood Obesity, 2023, vol. 19, No. 3, pp. 146-159 (Year: 2023).*

Amat-Bou et al. Nutrients, 2020, 12, 3123, pp. 1-15 (Year: 2020).*

Fak et al. PLOS ONE, 2012, vol. 7, Issue 10, pp. 1-8 (Year: 2012).*

Kong et al. Frontiers in Psychiatry, 2020, vol. 11, Article 594934, pp. 1-8 (Year: 2020).*

Akhondzadeh, Microbiome and Schizophrenia, Avicenna Journal of Medical Biotechnology, 2019, p. 269, 11(4).

Alyousif et al., The effects of *Bifidobacterium animalis* ssp. lactis B94 on gastrointestinal wellness in adults with Prader-Willi syndrome: study protocol for a randomized controlled trial, Trials, 2018, pp. 1-6, 19:256.

Amat-Bou et al., Effects of *Bifidobacterium animalis* Subsp. lactis (BPL1) Supplementation in Children and Adolescents with Prader-Willi Syndrome: A Randomized Crossover Trial, Nutrients, 2020, pp. 1-15, 12(10):3123.

(Continued)

*Primary Examiner* — Louise W Humphrey

*Assistant Examiner* — Jessica Faye Edwards

(74) *Attorney, Agent, or Firm* — QUARLES & BRADY LLP

(57) ABSTRACT

Disclosed herein are methods and compositions useful for the treatment of subjects suffering from Prader-Willi Syndrome (PWS). The methods include administering compositions comprising probiotics, such as *Lactobacillus reuteri* (*L. reuteri*) and *Bifidobacterium animalis* subsp. *lactis* (*B. lactis*) to subjects in need thereof.

16 Claims, 52 Drawing Sheets

Specification includes a Sequence Listing.

(56) References Cited

OTHER PUBLICATIONS

Anhê et al., Type 2 diabetes influences bacterial tissue compartmentalisation in human obesity, Nature Metabolism, 2020, pp. 233-242, 2.
Aoun et al., The Influence of the Gut Microbiome on Obesity in Adults and the Role of Probiotics, Prebiotics, and Synbiotics for Weight Loss, Preventative Nutrition and Food Science, 2020, pp. 113-123, 25(2).
Ayyanna et al., Anti-inflammatory and Antioxidant Properties of Probiotic Bacterium Lactobacillus mucosae AN1 and Lactobacillus fermentum SNR1 in Wistar Albino Rats, Frontiers in Microbiology, 2018, pp. 1-13, 9:3063.
Carreras et al., Anti-obesity properties of the strain *Bifidobacterium animalis* subsp. lactis CECT 8145 in Zücker fatty rats, Beneficial Microbes, 2018, pp. 1-14, 9(4).
Chatuphonprasert et al., Physiology and Pathophysiology of Steroid Biosynthesis, Transport and Metabolism in the Human Placenta, Frontiers in Pharmacology, 2018, pp. 1-29, 9:1027.
Chen et al., Antiobesity Effect of Lactobacillus Reuteri 263 Associated With Energy Metabolism Remodeling of White Adipose Tissue in High-Energy-Diet-Fed Rats, Journal of Nutritional Biochemistry, 2018, pp. 87-94, 54.
Cox et al., Obesity, inflammation, and the gut microbiota, Lancet Diabetes & Endocrinology, 2015, pp. 207-215, 3.
Crovesy et al., Profile of the gut microbiota of adults with obesity: a systematic review, European Journal of Clinical Nutrition, 2020, pp. 1251-1262, 74(9).
Crusell et al., Gestational diabetes is associated with change in the gut microbiota composition in third trimester of pregnancy and postpartum, Microbiome, 2018, pp. 1-19, 6:89.
Deng et al., miRNA-Gene Regulatory Network in Gnotobiotic Mice Stimulated by Dysbiotic Gut Microbiota Transplanted From a Genetically Obese Child, Frontiers of Microbiology, 2019, pp. 1-20, 10:1517.
Dickerson et al., Adjunctive Probiotic Microorganisms to Prevent Rehospitalization in Patients With Acute Mania: A Randomized Controlled Trial, Bipolar Disorder, 2018, pp. 614-621, 20(7).
Dimidi et al., Randomised clinical trial: Bifdobacterium lactis NCC2818 probiotic vs placebo, and impact on gut transit time, symptoms, and gut microbiology in chronic constipation, Alimentary Pharmacology & Therapeutics, 2019, pp. 251-264, 49(3).
Elmassry et al., Osteoprotective effect of green tea polyphenols and annatto-extracted tocotrienol in obese mice is associated with enhanced microbiome vitamin K2 biosynthetic pathways, Journal of Nutritional Biochemistry, 2020, pp. 1-10, 86:108492.
Eshraghi et al., Early Disruption of the Microbiome Leading to Decreased Antioxidant Capacity and Epigenetic Changes: Implications for the Rise in Autism, Frontiers in Cellular Neuroscience, 2018, pp. 1-19, 12:256.
Forsyth et al., Children with autism spectrum disorder: Pilot studies examining the salivary microbiome and implications for gut metabolism and social behavior, Human Microbiome Journal, 2020, pp. 1-7, 15:100066.
Garcia-Ribera et al., Specific Dietary Components and Gut Microbiota Composition are Associated with Obesity in Children and Adolescents with Prader-Willi Syndrome, Nutrients, 2020, pp. 1-12, 12(4):E1063.
Gomes et al., The Human Gut Microbiota: Metabolism and Perspective in Obesity, Gut Microbes, 2018, pp. 308-325, 9(4).
Grembi et al., Gut microbiota plasticity is correlated with sustained weight loss on a low-carb or low-fat dietary intervention, 2020, pp. 1-14, 10(1):1405.
Grimaldi et al., A prebiotic intervention study in children with autism spectrum disorders (ASDs), Microbiome, 2018, pp. 1-13, 6:133.
Hall et al., A novel Ruminococcus gnavus clade enriched in inflammatory bowel disease patients, Genome Medicine, 2017, pp. 1-12, 9:103.
Hersoug et al., Role of microbiota-derived lipopolysaccharide in adipose tissue inflammation, adipocyte size and pyroptosis during obesity, Nutrition Research Reviews, 2018, pp. 153-163, 31(2).
Hibberd et al., Probiotic or synbiotic alters the gut microbiota and metabolism in a randomised controlled trial of weight management in overweight adults, Beneficial Microbes, 2019, pp. 121-135, 10:2.
Hiippala et al., Isolation of Anti-Inflammatory and Epithelium Reinforcing Bacteroides and Parabacteroides Spp. from A Healthy Fecal Donor, Nutrients, 2020, pp. 1-18, 12(4):935.
Huerta-Ávila et al., High Relative Abundance of Lactobacillus reuteri and Fructose Intake Are Associated With Adiposity and Cardiometabolic Risk Factors in Children From Mexico City, Nutrients, 2019, pp. 1-14, 11(6):1207.
Huo et al., *Bifidobacterium animalis* subsp. lactis A6 Alleviates Obesity Associated with Promoting Mitochondrial Biogenesis and Function of Adipose Tissue in Mice, Molecules, 2020, pp. 1-18, 25(7):1490.
Iakovlev et al., The structure of the proteomic profile and gut microbiota in patients with primary immunodeficiency, common variable immunodeficiency and inflammatory bowel disease, Journal of Crohn's and Colitis, pp. S175-176, 14. Supplement_1:P081.
Ibarra et al., Effects of 28-day *Bifidobacterium animalis* subsp. lactis HN019 supplementation on colonic transit time and gastro-intestinal symptoms in adults with functional constipation: A double-blind, randomized, placebo-controlled, and dose-ranging trial, Gut Microbes, 2018, pp. 236-251, 9(3).
Jang et al., The Preventive and Curative Effects of Lactobacillus reuteri NK33 and Bifidobacterium adolescentis NK98 on Immobilization Stress-Induced Anxiety/Depression and Colitis in Mice, Nutrients, 2019, pp. 1-16, 11(819).
Karkhaneh et al., Effectiveness of Probiotics in Infantile Colic: A Rapid Review, Paediatrics & Child Health, 2020, pp. 149-159, 25(3).
Ke et al., Synbiotic-driven improvement of metabolic disturbances is associated with changes in the gut microbiome in diet-induced obese mice, Molecular Metabolism, 2019, pp. 96-109, 22.
Kong et al., New and preliminary evidence on altered oral and gut microbiota in individuals with autism spectrum disorder (ASD): implications for ASD diagnosis and subtyping based on microbial biomarkers, Nutrients, 2019, pp. 1-26, 11:2128.
Kong et al., Early Screening and Risk Factors of Autism Spectrum Disorder in a Large Cohort of Chinese Patients with Prader-Willi Syndrome, Frontiers in Psychiatry, 2020, Frontiers in Psychiatry, pp. 1-8, 11:594934.
Kong et al., The Effects of Limosilactobacillus reuteri LR-99 Supplementation on Body Mass Index, Social Communication, Fine Motor Function, and Gut Microbiome Composition in Individuals with Prader-Willi Syndrome: a Randomized Double-Blinded Placebo-Controlled Trial, Probiotics and Antimicrobial Proteins, 2021, pp. 1508-1520, 13.
Kong et al., The Effects of Probiotic Supplementation on Anthropometric Growth and Gut Microbiota Composition in Patients With Prader-Willi Syndrome: A Randomized Double-Blinded Placebo-Controlled Trial, Frontiers Nutrition, 2021, pp. 1-14, 8:587974.
Kovatcheva-Datchary et al., Dietary Fiber-Induced Improvement in Glucose Metabolism Is Associated with Increased Abundance of Prevotella, Cell Metabolism, 2015, pp. 971-982, 22(6).
Le Barz et al., In vivo screening of multiple bacterial strains identifies *Lactobacillus rhamnosus* Lb102 and *Bifidobacterium animalis* ssp. lactis Bf141 as probiotics that improve metabolic disorders in a mouse model of obesity, The FASEB Journal, 2018, pp. 4921-4935, 33(4).
Li et al., Combination of *Lactobacillus acidophilus* and *Bifidobacterium animalis* subsp. lactis Shows a Stronger Anti-Inflammatory Effect than Individual Strains in HT-29 Cells, Nutrients, 2019, pp. 1-17, 11(5):969.
Li et al., Correlation of Gut Microbiome Between ASD Children and Mothers and Potential Biomarkers for Risk Assessment, Genomics, Proteomics and Bioinformatics, 2019, pp. 26-38, 17(1).
Liang et al., Gut microbiota dysbiosis in Polycystic ovary syndrome (PCOS): association with obesity—A preliminary report, Canadian Journal of Physiology and Pharmacology, 2019, pp. 803-809, 98(11).

(56) References Cited

OTHER PUBLICATIONS

Liu et al., Probiotic Therapy for Treating Behavioral and Gastrointestinal Symptoms in Autism Spectrum Disorder: A Systematic Review of Clinical Trials, Current Medical Science, 2019, pp. 173-184, 39(2).
Lloyd-Price et al., Multi-omics of the gut microbial ecosystem in inflammatory bowel diseases, Nature, 2019, pp. 655-662, 569.
Lv et al., The association between gut microbiota composition and BMI in Chinese male college students, as analysed by next-generation sequencing, British Journal of Nutrition, 2019, pp. 986-995, 122.
Ma et al., Leucine and isoleucine have similar effects on reducing lipid accumulation, improving insulin sensitivity and increasing the browning of WAT in high-fat diet-induced obese mice, Food & Function, 2020, pp. 2279-2290, 11(3).
Mekkes et al., The development of probiotic treatment in obesity: a review, Beneficial Microbes, 2014, pp. 19-28, 5(1).
Meng et al., Consumption of *Bifidobacterium animalis* subsp. lactis BB-12 in yogurt reduced expression of TLR-2 on peripheral blood-derived monocytes and pro-inflammatory cytokine secretion in young adults, European Journal of Nutrition, 2017, pp. 649-661, 56(2).
Mörkl et al., Gut microbiota, dietary intakes and intestinal permeability reflected by serum zonulin in women, Eur J Nutr, 2018, pp. 2985-2997, 57(8).
Mounien et al., Anti-Obesity Effect of Carotenoids: Direct Impact on Adipose Tissue and Adipose Tissue-Driven Indirect Effects, Nutrients, 2019, pp. 1-14, 11(7):1562.
Navarro et al., Can probiotics benefit children with autism spectrum disorders?, World Journal of Gastroenterology, 2016, pp. 10093-10102, 22(46).
Oliphant et al., Macronutrient metabolism by the human gut microbiome: major fermentation by-products and their impact on host health, Microbiome, 2019, pp. 1-15, 7(1):91.
Oliveira et al., Benefits of *Bifidobacterium animalis* subsp. lactis Probiotic in Experimental Periodontitis, Journal of Peridontology, 2017, pp. 197-208, 88(2).
Olsson et al., Gut microbiota of obese subjects with Prader-Willi syndrome is linked to metabolic health, Gut, 2020, pp. 1229-1238, 69(7).
Onubi et al., Effects of probiotics on child growth: a systematic review, Journal of Health, Population, and Nutrition, 2015, pp. 1-15, 34:8.
Parks et al., Genetic Control of Obesity and Gut Microbiota Composition in Response to High-Fat, High-Sucrose Diet in Mice, Cell Metabolism, 2013, pp. 141-152, 17(1).
Pedret et al., Effects of daily consumption of the probiotic *Bifidobacterium animalis* subsp. lactis CECT 8145 on anthropometric adiposity biomarkers in abdominally obese subjects: a randomized controlled trial, International Journal of Obesity, 2019, pp. 1863-1868, 43.
Poutahidis et al., Microbial Reprogramming Inhibits Western Diet-Associated Obesity, PLoS ONE, 2013, pp. 1-11, 8 (7):e68596.
Poutahidis et al., Microbial Symbionts Accelerate Wound Healing via the Neuropeptide Hormone Oxytocin, PLoS ONE, 2013, pp. 1-17, 8(10):e78898.
Reily et al., Glycosylation in health and disease, Nature Reviews Nephrology, 2019, pp. 346-366, 15(6).
Robinson et al., Ketonuria Is Associated with Changes to the Abundance of Roseburia in the Gut Microbiota of Overweight and Obese Women at 16 Weeks Gestation: A Cross-Sectional Observational Study, Nutrients, 2019, pp. 1-10, 11(8):1836.
Rose et al., Differential immune responses and microbiota profiles in children with autism spectrum disorders and co-morbid gastrointestinal symptoms, Brain, Behavior, and Immunity, 2018, pp. 354-368, 70.
Rosing et al., Oral Lactobacillus Counts Predict Weight Gain Susceptibility: A 6-Year Follow-Up Study, Obesity Facts, 2017, pp. 473-482, 10.
Simon et al., Intake of Lactobacillus reuteri Improves Incretin and Insulin Secretion in Glucose-Tolerant Humans: A Proof of Concept, Diabetes Care, 2015, pp. 1827-1834, 38(10).
Sgritta et al., Mechanism underlying microbial-mediated changes in social behavior in mouse models of Autism Spectrum Disorder, Neuron, 2019, pp. 246-259, 101(2).
Song et al., Calcium Signaling Pathways: Key Pathways in the Regulation of Obesity, International Journal of Molecular Sciences, 2019, pp. 1-24, 20(11):2768.
Srikantha et al., The Possible Role of the Microbiota-Gut-Brain-Axis in Autism Spectrum Disorder, International Journal of Molecular Sciences, 2019, pp. 1-28, 20(9):2115.
Strati et al., New evidences on the altered gut microbiota in autism spectrum disorders, Microbiome, 2017, pp. 1-11, 5(1):24.
Taipale et al., *Bifidobacterium animalis* subsp. lactis BB-12 in reducing the risk of infections in early childhood, Clinical Investigation, 2016, pp. 65-69, 79(1).
Tenorio-Jiménez et al., Lactobacillus reuteri V3401 Reduces Inflammatory Biomarkers and Modifies the Gastrointestinal Microbiome in Adults With Metabolic Syndrome: The PROSIR Study, Nutrients, 2019, pp. 1-14, 11 (8):1761.
Thingholm et al., Obese Individuals with and without Type 2 Diabetes Show Different Gut Microbial Functional Capacity and Composition, Cell Host & Microbe, 2019, pp. 252-264, 26.
Tun et al., Roles of Birth Mode and Infant Gut Microbiota in Intergenerational Transmission of Overweight and Obesity From Mother to Offspring, JAMA Pediatrics, 2018, pp. 1-23, 172(4).
Uusitupa et al., *Bifidobacterium animalis* subsp. lactis 420 for Metabolic Health: Review of the Research, Nutrients, 2020, pp. 1-17, 12(4):892.
Varian et al., Microbial lysate upregulates host oxytocin, Brain, Behavior, and Immunology, 2017, pp. 36-49, 61.
Varian et al., Beneficial bacteria inhibit cachexia, Oncotarget, 2016, pp. 11803-11816, 7(11); Correction: Beneficial bacteria inhibit cachexia, Oncotarget, 2018, p. 29536, 9(50).
Vindegaard et al., Gut microbial changes of patients with psychotic and affective disorders: A systematic review, Schizophrenia Research, 2021, pp. 41-50, 234.
Vojinovic et al., Relationship between gut microbiota and circulating metabolites in population-based cohorts, Nature Communications, 2019, pp. 1-23, 10(1):5813.
Wang et al., Alleviating effects of walnut green husk extract on disorders of lipid levels and gut bacteria flora in high fat diet-induced obesity rats, Journal of Functional Foods, 2019, pp. 576-586, 52.
West et al., Microvesicles from Lactobacillus reuteri (DSM-17938) completely reproduce modulation of gut motility by bacteria in mice, PLoS ONE, 2020, pp. 1-13, 15(1):e0225481.
Zeng et al., Structural and functional profiles of the gut microbial community in polycystic ovary syndrome with insulin resistance (IR-PCOS): a pilot study, Research in Microbiology, 2019, pp. 43-52, 170(1).
Zhang et al., Dietary Modulation of Gut Microbiota Contributes to Alleviation of Both Genetic and Simple Obesity in Children, EBioMedicine, 2015, pp. 968-984, 2.
Zhu et al., Current Treatments of Prader-Willi Syndrome: A Systematic Review, North American Journal of Medicine and Science, 2017, pp. 156-163, 10:4.
PCT International Search Report and Written Opinion, PCT/US2021/064004, Mar. 18, 2022, 13 pages.
Office Action in Japanese Patent Application No. 2023-536812; received on Oct. 14, 2025.

* cited by examiner

TABLE 2. ESTIMATED MARGINAL MEANS OF BMI AT EACH STUDY TIMEPOINT.

| INTERVENTION | STUDY VISIT | ESTIMATED MEANS (95% CI) | STANDARD ERROR | DEGREES OF FREEDOM |
|---|---|---|---|---|
| ACTIVE PROBIOTIC | 0–WEEKS | 20.28 (18.347;22.212) | 0.732 | 18.074 |
| | 6–WEEKS | 19.300 (17.34;21.261) | 0.754 | 21.041 |
| | 12–WEEKS | 18.988 (17.049;20.928) | 0.743 | 20.146 |
| PLACEBO CONTROL | 0–WEEKS | 19.455 (15.751;23.159) | 1.427 | 21.507 |
| | 6–WEEKS | 21.908 (17.249;26.567) | 1.838 | 30.166 |
| | 12–WEEKS | 17.996 (13.252;22.739) | 1.873 | 30.510 |

FIG. 3

TABLE 3. PAIRWISE COMPARISONS OF CHANGE IN BMI AT 6–WEEKS AND 12–WEEKS COMPARED TO BASELINE.

| INTERVENTION | CONTRAST | MEAN DIFFERENCE | STANDARD ERROR | DEGREES OF FREEDOM | T–RATIO | P–VALUE |
|---|---|---|---|---|---|---|
| ACTIVE PROBIOTIC | 12W–6W | –0.312 | 0.362 | 23.153 | –0.863 | 1.000 |
| | 12W–0W | –1.291 | 0.366 | 30.012 | –3.532 | 0.004 |
| | 6W–0W | –0.979 | 0.361 | 23.562 | –2.710 | 0.037 |
| PLACEBO CONTROL | 12W–6W | –3.912 | 1.929 | 17.072 | –2.028 | 0.175 |
| | 12W–0W | –1.459 | 1.782 | 20.078 | –0.819 | 1.000 |
| | 6W–0W | 2.453 | 1.734 | 18.679 | 1.414 | 0.521 |

FIG. 4

| | 6-WEEKS | | | 12-WEEKS | | |
|---|---|---|---|---|---|---|
| | PLACEBO CONTROL | ACTIVE PROBIOTIC | P-VALUE | PLACEBO CONTROL | ACTIVE PROBIOTIC | P-VALUE |
| GARS-3 | | | | | | |
| OVERALL SEVERITY | 2.09±0.54 | 2.08±0.86 | 0.720 | 2.00±0.47 | 1.92±0.76 | 1.000 |
| COGNITIVE STYLE (CS) | 9.36±5.54 | 10.3±4.17 | 0.647 | 8.55±4.11 | 11.1±5.59 | 0.120 |
| EMOTIONAL RESPONSES (ER) | 14.0±3.46 | 14.4±6.14 | 0.703 | 14.9±2.91 | 14.3±4.50 | 0.849 |
| MALADAPTIVE SPEECH (MS) | 6.00±3.97 | 7.85±5.47 | 0.426 | 5.09±4.13 | 6.15±4.86 | 0.819 |
| RESTRICTIVE / REPETITIVE BEHAVIORS (RRB) | 17.8±8.28 | 20.2±7.63 | 0.623 | 18.1±7.52 | 18.5±9.81 | 0.820 |
| SOCIAL COMMUNICATION (SC) | 17.8±5.64 | 12.7±4.96 | 0.088 | 18.8±5.93 | 11.5±6.01 | 0.007 |
| SOCIAL INTERACTION (SI) | 14.9±10.4 | 10.1±10.0 | 0.095 | 13.1±8.55 | 7.69±5.57 | 0.037 |
| ASQ-3 | | | | | | |
| TOTAL | 153±53.4 | 178±44.6 | 0.485 | 123±33.3 | 193±33.8 | 0.032 |
| COMMUNICATION | 42.5±10.8 | 41.3±10.6 | 0.415 | 32.0±15.2 | 45.0±14.1 | 0.346 |
| FINE MOTOR | 22.5±15.4 | 24.4±17.4 | 0.686 | 11.0±8.22 | 25.0±15.3 | 0.027 |
| GROSS MOTOR | 28.3±18.6 | 35.6±14.7 | 1.000 | 24.0±10.8 | 39.3±15.1 | 0.245 |
| PERSONAL-SOCIAL | 29.2±11.6 | 39.4±13.2 | 0.197 | 31.0±12.4 | 40.7±15.1 | 0.234 |
| PROBLEM SOLVING | 30.8±15.3 | 36.9±14.1 | 1.000 | 25.0±12.7 | 42.9±8.09 | 0.051 |

FIG. 5

| FEATURE | MEAN ABUNDANCE | | MEAN DIFFERENCE e(A–C) | MEAN RATIO (A / C) | P–VALUE | Q–VALUE |
|---|---|---|---|---|---|---|
| | ACTIVE PROBIOTIC | PLACEBO CONTROL | | | | |
| ARACHIDONIC ACID METABOLISM | 218.946 | 360.134 | –141.188 | 0.608 | <0.001 | 0.0038 |
| VALINE, LEUCINE, AND ISOLEUCINE BIOSYNTHESIS | 7469.337 | 6922.962 | 546.3745 | 1.079 | 0.0002 | 0.0067 |
| MEIOSIS (YEAST) | 55.66 | 27.301 | 28.35896 | 2.039 | 0.0013 | 0.0410 |
| FLAVONOID BIOSYNTHESIS | 49.178 | 20.943 | 28.23494 | 2.348 | <0.001 | 0.0038 |
| CAROTENOID BIOSYNTHESIS | 71.609 | 20.88 | 50.72969 | 3.430 | <0.001 | <0.001 |
| STEROID BIOSYNTHESIS | 14.106 | 2.167 | 11.93979 | 6.511 | <0.001 | 0.0038 |
| VARIOUS TYPES OF N–GLYCAN BIOSYNTHESIS | 2.941 | 0.035 | 2.905789 | 84.023 | <0.001 | <0.001 |
| PHOTOSYNTHESIS (ANTENNA PROTEINS) | 90.51 | 0.47 | 90.04026 | 192.575 | <0.001 | <0.001 |
| CALCIUM SIGNALING PATHWAY | 5.321 | 0.025 | 5.295618 | 209.204 | <0.001 | <0.001 |

FIG. 8

| CLINICAL INDEX | ESTIMATE | STANDARD ERROR | Z–VALUE | P–VALUE |
|---|---|---|---|---|
| BMI | 2.6988679 | 2.255 | 1.197 | 0.231 |
| GARS – 3 SOCIAL COMMMUNICATION | 0.02712652 | 0.359 | 0.076 | 0.940 |
| GARS – 3 SOCIAL INTERACTION | 0.18394807 | 0.217 | 0.847 | 0.397 |
| ASQ – 3 TOTAL SCORE | 0.10223581 | 0.0864 | 1.184 | 0.236 |
| ASQ – 3 FINE MOTOR | –0.3069883 | 0.263 | –1.166 | 0.244 |

FIG. 10

| METABOLIC PATHWAY | ESTIMATE | STANDARD ERROR | Z–VALUE | P–VALUE |
|---|---|---|---|---|
| ARGININE AND PROLINE METABOLISM | 1.173E–05 | 4.019E–05 | 0.292 | 0.770 |
| CAROTENOID BIOSYNTHESIS | –7.380E–04 | 1.362E–03 | –0.542 | 0.588 |
| FLAVONOID BIOSYNTHESIS | –1.331E–04 | 9.938E–04 | –0.134 | 0.893 |
| INSULIN SIGNALING PATHWAY | –7.032E–05 | 2.345E–04 | –0.300 | 0.764 |
| LIPOPOLYSACCHARIDE BIOSYNTHESIS | 4.598E–05 | 9.611E–05 | 0.478 | 0.632 |
| LIPOPOLYSACCHARIDE BIOSYNTHESIS PROTEINS | –8.925E–06 | 6.780E–05 | –0.132 | 0.895 |
| METHANE METABOLISM | 7.245E–05 | 4.201E–05 | 1.725 | 0.085 |
| STARCH AND SUCROSE METABOLISM | –4.026E–05 | 1.812E–05 | –2.222 | 0.026 |
| STEROID BIOSYNTHESIS | –4.805E–03 | 3.321E–03 | –1.447 | 0.148 |
| VALINE, LEUCINE, AND ISOLEUCINE BIOSYNTHESIS | –8.859E–05 | 5.710E–05 | –1.551 | 0.121 |

FIG. 11

| MICROBIOTA | CLINICAL FEATURE | COEFFICIENT | STANDARD ERROR | P–VALUE | Q–VALUE |
|---|---|---|---|---|---|
| BIFIDOBACTERIACEAE (F) | BMI | –0.431 | 0.12685 | 0.00433 | 0.06707 |
| ERYSIPELOTRICHACEAE (F) | BMI | 0.261 | 0.07384 | 0.00329 | 0.06707 |
| ALISTIPES (G) | ER | –0.644 | 0.11926 | 0.00043 | 0.01217 |
| ALISTIPES (G) | RRB | –0.595 | 0.14462 | 0.00262 | 0.07335 |
| FAECALIBACTERIUM (G) | BMI Z–SCORE | –0.546 | 0.16112 | 0.00438 | 0.09727 |
| SUBDOLIGRANULUM (G) | BMI Z–SCORE | 0.641 | 0.2027 | 0.00695 | 0.09727 |

FIG. 12

| | PROBIOTIC | PLACEBO | P–VALUE* |
|---|---|---|---|
| GI SYMPTOMS (N=41, 47.5% HAS ≥ 1) | 0.87±1.63 | 1.39±1.75 | 0.24 |
| ALLERGIES (N=41, 78.5% HAS ≥ 1) | 1.78±1.59 | 1.83±1.25 | 0.74 |
| RRB (N=41, 100% ≥ 1) | 19.2±10.3 | 16.7±6.61 | 0.56 |
| SLEEP APNEA (N=65) | 27% | 20% | 0.48 |
| SCOLIOSIS (N=65) | 33% | 17% | 0.12 |
| UNDESCENDED TESTICLE (N=65) | 58% | 51% | 0.61 |

FIG. 15

SEQUENCE LISTING

```
Sequence total quantity: 2
SEQ ID NO: 1            moltype = DNA  length = 67
FEATURE                 Location/Qualifiers
misc_feature            1..67
                        note = Synthetic- 16S rRNA V3-V4 library Forward
variation               59
                        note = note = n is a, c, g, or t
source                  1..67
                        mol_type = other DNA
                        organism = synthetic construct
SEQUENCE: 1
```

-continued

```
tcgtcggcag cgtcagatgt gtataagaga cagcctacgg gaggcagcag cctacgggnb  60
gcascag                                                             67

SEQ ID NO: 2            moltype = DNA  length = 56
FEATURE                 Location/Qualifiers
misc_feature            1..56
                        note = Synthetic- 16S rRNA V3-V4 library Reverse
variation               42
                        note = note = n is a, c, g, or t
source                  1..56
                        mol_type = other DNA
                        organism = synthetic construct
SEQUENCE: 2
gtctcgtggg ctcggagatg tgtataagag acagtgacta cnvgggtatc taatcc      56
```

PROBIOTICS COMPOSITIONS AND METHOD OF USING THE SAME TO ENHANCE GROWTH AND SOCIAL FUNCTION IN CHILDREN

CROSS-REFERENCE TO RELATED APPLICATIONS

This application is a continuation of U.S. application Ser. No. 18/794,131 filed Aug. 5, 2024, which is a continuation of U.S. application Ser. No. 18/267,969, filed Jun. 16, 2023, which is the U.S. National Stage of PCT/US2021/064004 filed Dec. 17, 2021, which claims the benefit of U.S. Appl. No. 63/127,936, filed Dec. 18, 2020. The content of each of the above referenced applications is incorporated herein by reference in its entirety.

STATEMENT REGARDING FEDERALLY SPONSORED RESEARCH OR DEVELOPMENT

N/A

SEQUENCE LISTING

The contents of the electronic sequence listing (125141.04346.xml; Size: 4,385 bytes; and Date of Creation: Jun. 24, 2024) is herein incorporated by reference in its entirety.

FIELD

The field of the invention relates to methods and compositions useful for the treatment of subjects suffering from Prader-Willi Syndrome (PWS). The methods include administering compositions comprising probiotics, such as *Lactobacillus reuteri* (*L. reuteri*) and *Bifidobacterium animalis* subsp. *lactis* (*B. Lactis*) to subjects in need thereof.

BACKGROUND

Prader-Willi Syndrome (PWS) is an uncommon genetic syndrome that affects approximately one out of every 15,000 people (Cassidy S B, Irizarry K A). PWS is recognized as the most common genetic cause of life-threatening childhood obesity (Butler M G, Irizarry K A). Morbid obesity and neuropsychiatric complications are leading causes of death or long term disabilities. Besides some reported efficacy of growth hormone (Bakker N E, Kuppens R J, Zhu J L), the treatments are mainly behavioral.

The gut microbiota has been implicated in the pathogenesis of obesity and associated comorbidities in PWS subjects (Olsson L M). Independent of the PWS population, the diversity and composition of the gut microbiome has been reported to have an impact on nutrient metabolism and energy expenditure (Aoun A). While gut microbiome diversity and composition were found to be different between obese and lean individuals (Lv Y), gut dysbiosis was found to be quite similar in PWS-related obesity and diet-related obesity (Zhang C).

Gut microbiome dysbiosis has been shown to activate the inflammatory process and contribute to the development of insulin resistance (Corado Gomes A). Dysbiotic gut microbiota transplanted from PWS patients to rats impacted expression of GLP-1 and decreased insulin-receptor signaling two weeks prior to an increase in body fat composition, indicating that gut microbiome dysbiosis may play a role in the development of obesity (Deng). Recent research has shown the potential for probiotics to improve gut microbiome and metabolic disturbance in diet-induced obese mice (Ke X) and also in a randomized controlled trial of weight management in overweight adults (Hibberd). Microbiome dysbiosis is not only related to obesity but is also closely associated with neuropsychiatric conditions, including schizophrenia (Akhondzadeh S), psychotic disorders (Vindegaard N), and autism spectrum disorders (ASD)(Navarro F). Past research conducted in our laboratory even indicates that the microbiome has the potential to serve as biomarker to assist in the diagnosis and subtyping of ASD (Kong X J et al). Probiotics treatments have already been broadly used to help people with neuropsychiatric disorders (Liu J, Dickerson F).

*Lactobacillus reuteri* (*L. reuteri*) is a well-studied probiotic bacterium that can colonize a large number of mammals. Direct supplementation or prebiotic modulation of *L. reuteri* may be an attractive preventive and/or therapeutic avenue against inflammatory and metabolic diseases (Navarro F). *L. reuteri* V3401 was reported to reduce inflammatory biomarkers, modify the gastrointestinal microbiome and motility, and improve metabolic syndrome in adults (Tenorio-Jimenez, West C L). *L. reuteri* was also shown to improve incretin and insulin secretion in glucose-tolerant humans (Simons M C). Notably, *L. reuteri* 263 demonstrated anti-obesity effects through promoting remodeling of white adipose tissue in high-energy-diet-fed rats (Chen L H). Despite these findings that detail the positive effects of *L. reuteri* on the gut microbiome and metabolism, the direct effect of *L. reuteri* on obesity in humans is still debated. In fact, one study even found an correlation between the endogenous abundance of *L. reuteri* and adiposity in Mexican children (Huerta-Avila). In addition to these metabolic benefits, *L. reuteri* has also been shown to exert beneficial effects on the brain and behavior. *L. reuteri* (DSM-17938) was associated with a significant decrease in average crying time in infantile colic (Karkhaneh M). *L. reuteri* NK33, in combination with *B. adolescentis* NK98, alleviated and prevented development of immobilization stress-induced anxiety/depression and colitis in mice (Jang H M). A research group at MIT reported that *L. reuteri* up-regulates the neuropeptide hormone oxytocin (OXT), a factor integral to social bonding and reproduction, within a vagus nerve-mediated pathway in mice, while preventing age-related weight gain (Poutahidis T[1], Varian B). The same group reported that these benefits extended to human subjects; similarly to as in mice, OXT-producing cells were found to be increased in the caudal paraventricular nucleus (PVN) of the hypothalamus after consumption of *L. reuteri* lysate (Poutahidis T[2]). Additional research has found that *L. reuteri* acts in a vagus nerve-dependent manner to rescue deficits in social interaction-induced synaptic plasticity in the ventral tegmental area via oxytocin signaling modulation in multiple models of ASD (Sgritta M). *L. reuteri* treatments were found to improve unsocial behavior in male Shank3 mice and decrease repetitive behaviors in both male and female Shank3 KO mice (Sgritta M).

*Bifidobacterium animalis* subsp. *lactis* (*B. lactis*) is a rod-shaped, anaerobic bacteria that can be found in the gastrointestinal tract of most mammals, including humans [16]. Anti-obesity effects have been linked to administration of some strains of *B. lactis*, such as A6, CECT 8145, Bf141, B420 and BB-12 (Alyousif et al., 2018; Barz et al., 2019; Carreras et al., 2018; Dimidi et al., 2019; Huo et al., 2020; Ibarra et al., 2018; Pedret et al., 2019b; Uusitupa et al., 2020a). Increase in the abundance of *B. lactis* in the gut has been associated with general health and anti-inflammatory benefits. Many strains of *B. lactis* are considered to be health-promoting probiotics and are commonly formulated into fermented dairy foods. Topical application of *B. lactis* HN019 was shown to slow the development of symptoms related to experimental periodontitis in rats(Oliveira et al., 2017). One study reported that administration of *B. lactis* BB-12 reduced the risk of respiratory tract infections in early childhood(Taipale et al., 2016). Another study found combination use of *B. lactis* with *Lactobacillus acidophilus* reduced inflammatory signaling in intestinal epithelial cells (S.-C. Li et al., 2019).

While the positive effects of probiotics have been well documented in the general population, it is unclear whether similar effects would be observed in subjects with a different genetic background, such as subjects suffering from PWS.

SUMMARY

Disclosed herein are methods and compositions useful for the treatment of a subjects suffering from or suspected of having PWS. The methods include administering an effective amount of a composition comprising one or more probiotics. In some embodiments, the probiotic comprises one or more of a *Lactobacillus*, sp., *Saccharomyces*, sp., *Bifidobacterium*, sp., *Bacillus*, sp. and *Eubacterium hallii*. In some embodiments, the probiotic comprises a *Lactobacillus*, sp. (e.g., *Lactobacillus reuteri* (*L. reuteri*) and *Bifidobacterium animalis* subsp. *lactis* (*B. lactis*), and *Bifidobacterium animalis*, subsp.

In some embodiments, the subject is suffering from one or more of the following symptoms or conditions: obesity, short statue, social deficits, fine motor abnormalities, developmental delay, and abnormal behavioral characteristics; wherein after treatment, the subject's symptoms or conditions are decreased as compared to before treatment. In some embodiments, the developmental delay comprises one or more of communication, gross motor control, fine motor control, problem-solving, and personal-social interaction by *L. reuteri*. In some embodiments, the abnormal behavioral characteristics comprise one or more of restrictive, repetitive behaviors (RRB), aberrant social interaction (SI), aberrant social communication (SC), aberrant emotional responses (ER), aberrant cognitive style (CS), and maladaptive speech (MS) by *L. reuteri*. In some embodiments, the subject is suffering from obesity, short statue, and wherein the subject's body-mass index (BMI) after treatment is lower than the subject's BMI before treatment by *L. reuteri* and wherein the subject's height after treatment is higher than the subject's height before treatment by *B. lactis*. In some embodiments, the subject is suffering from varying severities of psychopathology measured via Clinical Global Impression-Improvement (CGI-I) after treatment is lower than the subject's baseline CGI severity before treatment by *B. lactis*. In some embodiments, the subject is suffering from developmental delays, and wherein the subject's Ages and Stages Questionnaires, 3rd Edition (ASQ-3) score is statistically improved for one or more of communication, gross motor function, fine motor function, problem-solving, and personal-social interaction after treatment as compared to the subject's ASQ-3 score before treatment by *L. reuteri*. In some embodiments, wherein the subject is suffering from abnormal behavioral characteristics, and wherein the subject's Third Edition GARS-3 score (GARS-3) is statistically improved for one or more of RRB, SI, SC, ER, CS and MS after treatment as compared to the subjects GARS-3 score before treatment for *L. reuteri*. In some embodiments, the subject is suffering from varying severities of psychopathology and wherein the subject's Clinical Global Impression-Improvement (CGI-I) is statistically improved for one or more scores of improvement (CGI-I) and severity (CGI-S) after treatment as compared to the subject's CGI-I and CGI-S score before treatment for *B. lactis*.

In some embodiments, the treatment comprises administering an effective dose of the probiotic once per day, twice per day, three times per day, or four times per day. In some embodiments, the treatment comprises administering an effective dose of the probiotic for at least about 3 weeks, 4 weeks, 5 weeks, 6 weeks, 7 weeks, 8 weeks, 9 weeks, 10 weeks 11 weeks, or at least about 12 weeks. In some embodiments, the effective dose comprises about $1\times10^3$, about $2\times10^3$, about $3\times10^3$ about $4\times10^3$, about $5\times10^3$ about $6\times10^3$ about $7\times10^3$, about $8\times10^3$, about $9\times10^3$ or about $10\times10^3$ colony forming units (CFU) of probiotic. In some embodiments, the subject is administered one or more additional therapeutics.

In some embodiments, the probiotic comprises either *L. reuteri* or *B. lactis*, wherein the probiotic is administered twice per day at a dose of about $3\times10^3$ CFU for 12 weeks, and wherein after treatment, the subject exhibits a statistically relevant improvement in one or more of BMI, fine motor function, and problem solving skills as measured by ASQ-3 testing. In some embodiments, the microbiome composition of the subject is different after the treatment as compared to before the treatment. In some embodiments, the difference comprises a decrease in one of more of *Escherichia-Shigella, Porphyromonas*, and *Ruminococcus torques* by *L. reuteri*. In some embodiments, the difference comprises an increase in one of more of *Bifidobacterium, Lactobacillus, Faecalibacteria, Roseburia*, and *Alistipes* by *L. reuteri*. In some embodiments, the difference comprises a significant positive association of *Rothia* against RRB after treatment with *B. lactis*.

In some embodiments, a composition is provided comprising an effective dose of one or more probiotics, and a growth hormone. In some embodiments, the probiotic comprises *Lactobacillus* sp. In some embodiments, the probiotic comprises *Lactobacillus reuteri* and the growth hormone comprises human growth hormone.

BRIEF DESCRIPTION OF THE DRAWINGS

These and other embodiments, aspects, advantages, and features of the present invention will be set forth in part in the description which follows, and will become apparent to those skilled in the art by reference to the following description of the invention and referenced drawings or by practice of the invention. The accompanying drawings illustrate one or more implementations, and these implementations do not necessarily represent the full scope of the invention.

FIG. 3. Table summary of estimated marginal means of BMI at each study timepoint for the study on *L. reuteri*.

FIG. 4. Table summary of pairwise comparisons of change in BMI at 6-weeks and 12-weeks compared to baseline for the study on *L. reuteri*.

FIG. 5. Table summary of psychological measurements, including the ASQ-3 and GARS-3 measures at study timepoints 6- and 12-weeks for the study on *L. reuteri*.

FIG. 8. Table of predicted KEGG enzyme abundance based on PICSRUSt-2 predictive functional profiling for subjects receiving either active probiotic or placebo control. The average abundance of KEGG enzyme abundances are differentially enriched in placebo and probiotics at level 3.

FIG. 10. Provides a table showing a summary of clinical logistic regression model indices used in ROC analysis for the study on *L. reuteri*.

FIG. 11. Provides a table showing a summary of predictive metagenomic profiling logistic regression model indices used in ROC analysis for the study on *L. reuteri*.

FIG. 12. Provides a table showing the univariat association between genus and family level bacterial abundance and clinical measurements at weeks 6 and 12 combined based on general linear model using MaAsLin2 package. Shown significant correlations are based on the active probiotic group. Taxonomic ranking is labeled in parentheses with "f" denoting family level and "g" denoting genus level microbiota.

FIG. 15. Table showing co-morbid symptoms of study participants.

DETAILED DESCRIPTION

Figure 1:
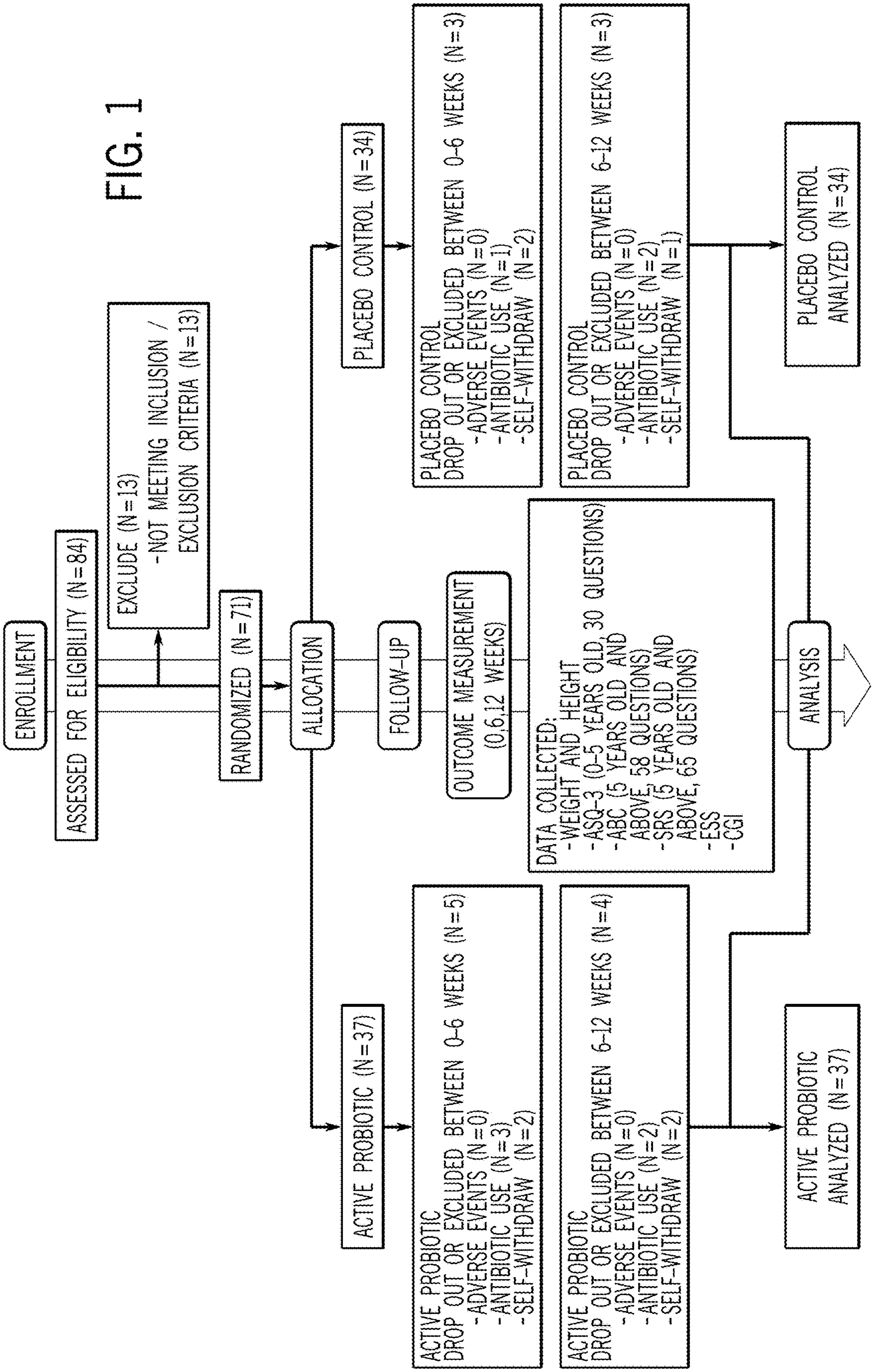
FIG. 1. Flowchart summary of study conduct and participant enrollment and dropout for the study on *L. reuteri*.

Herein describes two independent, randomized, double-blind, placebo-controlled trial to test whether probiotic consumption has beneficial effects on obesity, social behaviors, anthropomorphic growth, and neurodevelopment in PWS, and to determine whether these effects are associated with gut microbiome changes. To perform these studies, the present inventors enrolled a total of 71 PWS patients for evaluating the efficacy of a *L. reuteri* strain (LR-99) and a total of 65 PWS patients for evaluating the efficacy of a *B. lactis* strain (BB-11) on their body-mass index (BMI), psychological measurements, and gut microbiome composition and functions relative to placebo controls. In addition to potentially supporting a new intervention for patients with PWS, the microbiome composition data collected from this study may shed light on the underlying mechanisms of PWS pathology and the gut-brain axis.

The presently disclosed subject matter is described herein using several definitions, as set forth below and throughout the application.

Definitions

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

Wherever embodiments are described with the language "comprising," otherwise analogous embodiments described in terms of "consisting of" and/or "consisting essentially of" are included.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value).

Numeric ranges are inclusive of the numbers defining the range, and any individual value provided herein can serve as an endpoint for a range that includes other individual values provided herein. For example, a set of values such as 1, 2, 3, 8, 9, and 10 is also a disclosure of a range of numbers from 1-10, from 1-8, from 3-9, and so forth. Likewise, a disclosed range is a disclosure of each individual value encompassed by the range. For example, a stated range of 5-10 is also a disclosure of 5, 6, 7, 8, 9, and 10.

The present invention has been described in terms of one or more preferred embodiments, and it should be appreciated that many equivalents, alternatives, variations, and modifications, aside from those expressly stated, are possible and within the scope of the invention.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition. For purposes of this disclosure, "treating" or "treatment" describes the management and care of a patient for the purpose of combating the disease, condition, or disorder. The terms embrace both preventative, i.e., prophylactic, and palliative treatment. "Treating" includes the administration of a composition of present disclosure to prevent the onset of the symptoms or complications, alleviating the symptoms or complications, or eliminating the disease, condition, or disorder. The term "treat" and words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the methods of this disclosure can provide any amount of any level of treatment or prevention of disease in a mammal. Furthermore, the treatment or prevention provided by the inventive method can include treatment or prevention of one or more conditions or symptoms of the disease or disease state, e.g., PWS, being treated or prevented. Also, for purposes herein, "prevention" can encompass delaying the onset of the disease, or a symptom or condition thereof for purposes of the present disclosure, "treating" or "treatment" comprises the management and care of a subject for the purpose of combating a disease, condition, or disorder. Treating includes the administration of a probiotic as described herein to prevent the onset of the symptoms or complications, and/or to alleviate the symptoms or complications of a disease, condition, or disorder.

The term "treating" can be characterized by one or more of the following: (a) improvement in body-mass index (BMI) e.g., by reduction in body weight and/or increase in height; (b) improvement in developmental delay characteristics, and/or (c) an improvement in abnormal behavioral characteristics. By way of example but not by way of limitation, treatment can be characterized by an improvement in one or more characteristics such as body weight, height, BMI, communication, gross motor control/function, fine motor control/function, problem-solving, personal-social interaction, restrictive, repetitive behaviors (RRB), aberrant social interaction (SI), aberrant social communication (SC), aberrant emotional responses (ER), aberrant cognitive style (CS), and maladaptive speech (MS). Furthermore, individuals with PWS are known to have short statue, failure to thrive, poor muscular tone, foods cravings, delayed development, cognitive disabilities, mood and behavioral issues, obesity, sleep apnea, and co-morbid autism; alleviation or favorable changes of such common symptoms are also considered improvements in PWS symptoms.

As used herein, the terms "effective amount" and "therapeutically effective amount" refer to the quantity of active therapeutic agent or agents sufficient to yield a desired therapeutic response without undue adverse side effects such as toxicity, irritation, or allergic response. The specific "effective amount" will, obviously, vary with such factors as the particular condition being treated, the physical condition of the subject, the duration of the treatment, the nature of concurrent therapy (if any), and the specific formulations employed and the structure of the therapeutic or its derivatives. The exact dosage is chosen by the individual physician in view of the patient to be treated. Dosage and administration are adjusted to provide sufficient levels of the active agent(s) or to maintain the desired effect.

By "subject" or "individual" or "animal" or "patient" is meant any subject, particularly a mammalian subject, for whom diagnosis, prognosis, or therapy is desired. The present invention is generally applied to humans, but one may use the present invention for veterinary purposes. For example, one may wish to treat, or test a treatment, on commercially important farm animals, such as cows, horses, pigs, rabbits, goats, and sheep, or relevant laboratory animals, such as rats, mice, rabbits, and so on. One may also wish to treat companion animals, such as cats and dogs.

In some embodiments, the optimum effective amounts can be readily determined by one of ordinary skill in the art using routine experimentation. In some embodiments, a therapeutically effective amount is achieved by administering multiple therapeutically effective doses, e.g., over the course of a day, several days, a week, several weeks, months, or years.

Any appropriate method can be practiced to determine, detect, or monitor a subject's response to treatment according to a method provided herein. As used herein, "determining a subject's response to treatment" refers to the assessment of the results of a therapy in a subject in response to administration of a composition provided herein or to treatment according to a method provided herein.

As used herein, body mass index (BMI) refers to a number that is used as an estimate of an individual's body fat. BMI can be calculated by dividing a person's weight in kilograms by the square of the person's height in meters, or by dividing a person's weight in pounds by the square of the person's height in inches and multiplying by a factor of 703. Moreover, a high BMI is associated with an increased risk for chronic diseases such as heart disease, high blood pressure, and type 2 diabetes in adults. Additionally, BMI also provides a reasonable estimate of body fat for most people.

Clinical Global Impression (CGI) is a scale used to measure symptom severity and treatment response. It is a three-item observer-rated scale that is used by clinicians and researches to track symptom changes, e.g., prior to versus after initiating a treatment. The three items that it assesses are: 1) Severity of Illness (CGI-S), 2) Global Improvement (CGI-I), and 3) Efficacy Index (CGI-E), which is a measure of treatment effect and side effects specific to drugs that were administered. The CGI was developed for use in NIMH-sponsored clinical trials to provide a brief, stand-alone assessment of the clinician's view of the patient's global functioning prior to and after initiating a study medication. The CGI comprises two companion one-item measures evaluating the following: (a) severity of psychopathology from 1 to 7 (CGI-S) and (b) change from the initiation of treatment on a similar seven-point scale (CGI-I).

As used herein the Ages & Stages Questionnaires®, Third Edition (ASQ®-3) is a questionnaire that is commonly used to track developmental progress in children between the ages of one month to 5½ years. The ASQ-3 has five scoring domains: communication, gross motor, fine motor, problem-solving, and personal-social. Each domain contains 6 question which are age matched. It is one of the most widely available development, communication, and behavior screening tools for young children (Perera et al. 2017, Squires et al. 2009). While this is one of the most common there are other similar scales that are less common or are meant for studies of a different format.

As used herein, the Gilliam Autism Rating Scale, Third Edition (GARS-3) is a questionnaire that helps identify autism in individuals and assess its severity. It consists of 56 items describing characteristic behaviors of individuals with autism. The items are grouped into six subscales: restrictive, repetitive behaviors (RB), social interaction (SI), social communication (SC), emotional responses (ER), cognitive style (CS), and maladaptive speech (MS). GARS-3 is a norm-referenced screening instrument used to identify persons with autism spectrum disorders for age 3-22, third edition since 1995 (Gilliam, 1995; Gilliam, 2014). It has proven to have a high rate of validity and reliability, which makes it highly utilized in the psychology field (Benjamin C K 2016, Duffy et al. 2017).

Prader-Willi Syndrome

As used herein, the term "Prader-Willi syndrome" (PWS) refers to a rare genetic imprinting disorder with an estimated prevalence of $1/10{,}000$-$1/30{,}000$[1]. Three mechanisms cause this genetic disorder: deletion (DEL) of the 15q11.2-q13 region from the paternal chromosome (~74% of cases), maternal uniparental disomy (UPD) from the mother (~25%), and imprinting defect (~1%) (Cassidy, 1997). PWS is characterized by severe hypotonia and feeding difficulties in early infancy, and subsequent hyperphagia and morbid obesity starting during early childhood (Cassidy, 2012). PWS patients also typically experience generalized neurodevelopmental delays and numerous neuropsychiatric comorbidities(Salehi, 2018).

Prader-Willi syndrome currently has no cure. Of the symptomatic treatments available, growth hormone replacement therapy has proven to be most effective, especially when administered early in development (WHO Multicentre Growth Reference Study Group, 2006). Growth hormone has been shown to improve not only height but also cognition and motor function. Other treatment options mainly include treatment of co-morbid psychiatric conditions through cognitive behavioral therapy and counseling.

PWS, like many other neurodevelopmental disorders, exists on a spectrum with a diverse set of signs and symptoms that include poor muscle tone and lack of eye coordination during infancy, hypotonia and abnormal neurological function, hypogonadism, developmental and cognitive delays (e.g., delays in milestones regarding communication, gross motor control, fine motor control, problem-solving, and personal-social interaction), hyperphagia and obesity, short stature, and abnormal behavioral characteristics (e.g., restrictive, repetitive behaviors (RRB), aberrant social interaction (SI), aberrant social communication (SC), aberrant emotional responses (ER), aberrant cognitive style (CS), and maladaptive speech (MS)), and psychiatric disturbances.

As used herein, "Autism spectrum disorder" (ASD) refers to a developmental condition characterized by social communication deficits and restricted/repetitive behaviors. ASD, like PWS, exists on a spectrum with a diverse set of signs and symptoms with highly variable severity. While most cases of autism are idiopathic, it is estimated that about 90% of cases are genetically caused. According to the latest estimates from the Centers for Disease Control, ASD has a prevalence of 1 in 54 births (Maenner et al., 2020). Approximately 25-40% of children with PWS have co-morbid ASD (Bennett et al., 2015). PWS and ASD are both forms of developmental delay, which is a group of conditions that impair learning and functioning of children during early developmental stages.

As used herein, the term "probiotic" refers to organisms, generally bacteria, which are considered to be beneficial rather than detrimental to their animal host. In terms of digestive health the concept of consuming beneficial bacteria has been popular in recent years, even though the benefit of consuming specific strains of bacteria was first proposed by Elie Metchnikoff in 1907. He suggested that since lactic acid bacteria can prevent putrefaction of stored food, they may also benefit the gastrointestinal tract; Bulgarian *bacillus* (later identified as *Lactobacillus delbruickii* subspecies *bulgaricus*) isolated from a fermented milk product was of particular interest. Metchnikoff proposed it was the optimal strain to consume because of its ability to produce large amounts of lactic acid with little succinic or acetic acid; its ability to coagulate milk rapidly; and the lack of alcohol and acetone produced. Interest in probiotics waned with the advent of antibiotics. However, with the emergence of antibiotic-resistant bacteria, there is renewed interest in probiotic bacteria, which are now defined as "live microorganisms which when administered in adequate amounts confer a health benefit on the host." It is now a popular concept that the accumulation of probiotic organisms in the gut is beneficial to the general health of the host organism and there are reports which indicate that the administration of probiotics is useful in the treatment of intestinal disease. Surprisingly and unexpectedly, therapeutic probiotic compositions are also useful for the treatment of Prader-Willi syndrome, as disclosed herein.

Exemplary probiotic bacteria include, without limitation *Lactobacillus*, sp., *Saccharomyces*, sp., *Bifidobacterium*, sp., *Streptococcus*, sp., *Escherichia coli., Bacillus*, sp., and *Eubacterium hallii*. Specific examples of such probiotics include: *L. reuteri* V3401, which was reported to reduce inflammatory biomarkers and modify the gastrointestinal microbiome and subsequently improve metabolic syndrome in adult (Tenorio-Jiménez et al., 2019), *L. Reuteri* 263, which demonstrated anti-obesity effect associated with energy metabolism remodeling of white adipose tissue in high-energy-diet-fed rats (Chen et al., 2018), and L. *Reuteri* (West et al., 2020) (DSM-17938), which was reported to modulate gut motility in mice. Furthermore, *L. Reuteri* NK33 along with *B. adolescentis* NK98 demonstrated immobilization stress-induced anxiety/depression and colitis in mice.

*Bifidobacterium animalis* subsp. *lactis* (*B. lactis*): administration of some strains of *B. lactis*, such as A6, CECT 8145, Bf141, B420, and BB-12, mostly in animals(Chen et al., 2018; Hibberd et al., 2019; Huerta-Avila et al., 2019; Simon et al., 2015; Tenorio-Jimenez et al., 2019; West et al., 2020). Anti-inflammatory effects of some strains of *B. lactis*, such as HN019 and BB-12, have also been reported in recent years (Akhondzadeh, 2019; Vindegaard et al., 2020).

The probiotic compositions disclosed herein may include one type of probiotic organism or a combination of different probiotic organisms. While the two present probiotic studies involve the administration of single-strain probiotics, there exists an increasing trend of multi-strain probiotic research to evaluate potential additive or synergistic effects between the probiotic strains. Specifically, previous research has shown that the combined use of *B. lactis* with *Lactobacillus acidophilus* reduced inflammatory signaling in intestinal epithelial cells.

Disclosed herein are therapeutic probiotic compositions comprising one or more probiotic microorganism. In some embodiments, the therapeutic probiotic compositions are formulated for oral administration, for example, as a food product or a food supplement. By way of example but not by way of limitation, probiotic compositions may be formulated as a milk-based product, and may be provided in milk, yogurt, cheese, or ice cream. The food product may be formulated as a non-dairy product, such as a fruit-based product, or a soya-based product. Such foods products can be in solid or liquid/drinkable form. Further, the food product can contain all customary additives, including but not limited to, proteins, vitamins, minerals, trace elements, and other nutritional ingredients.

In some embodiments, a therapeutic probiotic composition is formulated as a liquid, a powder, a capsule, a tablet, or a sachet for oral administration. In some embodiments, a capsule or tablet may include an enteric coating, and a therapeutic probiotic composition may include one or more pharmaceutically acceptable carriers. In some embodiments, the carrier may be a capsule for oral administration. In such an embodiment, an outer housing of the capsule may optionally be made of gelatin or cellulose. Cellulose has the benefit of maintaining the formulation in intestinal fluid, disallowing premature breakdown in the upper gastrointestinal tract, so the product can reach the desired destination. Alternatively, the ingredients may be combined and formed into a tablet. In tablet form, cellulose may also be present to act as a binder to hold the tablet together. Probiotic compositions may further comprise one or more excipients to facilitate the manufacturing process by preventing the ingredients from adhering to machines. Moreover, such excipients may render the capsule or tablet form easier to swallow and digest through the intestinal tract. The excipients may be a vegetable stearate, magnesium stearate, steric acid, ascorbyl palmitate, retinyl palmitate, or hyproxypropyl methylcellulose. Additional colors, flavors, and excipients known in the art may also be added. The formulated probiotic composition may be administered as formulated (e.g., as a capsule or tablet), or may be combined with food or drink for administration.

Therapeutic probiotic compositions may include lyophilized microorganisms, live cultures, or a combination thereof, and the microorganisms may be provided in therapeutically effective doses. In some embodiments, a therapeutically effective dose may comprise between about $1\times10^5$-$1\times10^{15}$ microorganisms per dose (colony forming units (CFU) per dose); between about $1\times10^6$-$1\times10^{14}$ microorganisms per dose; between about $1\times10^7$-$1\times10^{13}$ microorganisms per dose; between about $1\times10^8$-$1\times10^{12}$ microorganisms per dose, between about $1\times10^9$-$1\times10^{11}$ microorganisms per dose; between about $1\times10^{10}$-$9\times10^{10}$ microorganisms per dose; or about $3\times10^{10}$ microorganisms per dose. For both present studies that evaluated the effects of *L. reuteri* and *B. lactis* in individuals with PWS, each subject randomized to the active probiotic group were instructed to take $3\times10^{10}$ colony forming units (CFUs) per dose of the respective probiotics twice a day.

An effective does of a therapeutic probiotic composition may be administered to a subject in need thereof once per day, twice per day, three times per day, four times per day or more. In some embodiments the therapeutic probiotic compositions are administering an effective dose of the probiotic for at least about 3 weeks, 4 weeks, 5 weeks, 6 weeks, 7 weeks, 8 weeks, 9 weeks, 10 weeks 11 weeks, or at least about 12 weeks. In some embodiments, a therapeutic probiotic composition is administered for several years, or for the lifetime of a subject, continuously, or periodically, as symptoms dictate. By way of example, but not by way of limitation, in some embodiments, an effective dose of a therapeutic probiotic composition is administered daily, for example, twice per day, over the course of 12 weeks.

In some embodiments, a therapeutic composition comprising a probiotic such as *L. reuteri*, is administered in combination with one or more additional active agents. By way of example, additional active agents include growth hormone (e.g., human growth hormone), oxytocin, serotonin, dopamine. The additional active agent may be administered simultaneously with the probiotic composition (e.g., as part of the same formulation), or it may be administered separately, either at the same time or at a different time than the probiotic composition. Thus in some embodiments, a subject in need thereof (e.g., a subject diagnosed with or suspected of having PWS) is administered a composition comprising a probiotic and one or more additional active agents.

In some embodiments, the methods of the present inventions change the microbiome composition of the subject such that it is different after the treatment as compared to before the treatment. In the Examples, the inventors demonstrate that the composition of the gut microbiome underwent substantial changes following administration of *L. reuteri* LR-99 probiotic (see, e.g., FIG. 6 and FIG. 7), and they have associated changes in microbiota abundances with clinical indices (see FIG. 13). Specifically, they determined that the abundance of certain bacteria (i.e., *Escherichia-Shigella, Porphyromonas*, and *Ruminococcus torques*) was decreased following treatment, whereas the abundance of other bacteria (i.e., *Bifidobacterium, Lactobacillus, Faecalibacteria, Roseburia*, and *Alistipes*) was increased following treatment with *L. reuteri*. Given that *Bifidobacterium* is widely regarded as beneficial to gut health and weight reduction,(Pedret et al., 2019a; Uusitupa et al., 2020b) the inventors also observed significant alterations to the gut microbiome profiles and specific gut microbiota of individuals with PWS following supplementation with *B. lactis* (see FIG. 18-20). Interestingly, the inventors found that the improvement in Clinical Global Impression-Improvement (CGI-I) was significantly improved following 12 weeks of *B. lactis* supplementation. These findings demonstrated that both *L. reuteri* and *B. lactis* as potent probiotics induce significant favorable gut microbiome composition changes which led reduced fat deposit via insulin and calcium signaling regulation, and improved mental health via gut brain axis.

*Lactobacillus* is known to have protective effects against weight gain in humans and has been found to inhibit the activity of proinflammatory interleukins linked to obesity and poor obesity-related outcomes.(Cox et al., 2015; Rosing et al., 2017a) Surprisingly, the inventors observed an improvement in overall development measured by ASQ-3 total scores ($P<0.05$), fine motor function ($P<0.05$) and also possible problem solving skill ($P=0.051$) following supplementation with *L. reuteri*. Such results have not been found within any literature reports of such observed effects in the above areas. Furthermore, *L. reuteri* intervention significantly improved social communication ($P<0.01$) and social interaction ($P<0.05$) compared to controls for those older than 3 years old. *L. reuteri* rescues social interaction-induced synaptic plasticity in the ventral tegmental area of ASD mice, but not in oxytocin receptor-deficient mice.(Sgritta et al., 2019) Oxytocin nasal spray has been used to treat PWS subjects with beneficial effects,(Junli Zhu & Xuejun Kong, 2017) use of *L. reuteri* has not yet reported to improve social function in human study, which could induce endogenous oxytocin release will be more cost effective, convenient, and potentially longer lasting than using oxytocin directly. This finding warrant further study of the internal mechanism via oxytocin or other neurotransmitters/hormones involved in pathogenesis of PWS and its co-morbidities.

Thus, these findings strongly support the use of probiotics as a valuable early intervention to improve the overall developmental level and therefore change the prognosis of those with PWS. Furthermore, such probiotic strains could potentially apply to the children with developmental delays of other causes and further studies in these areas are urgently indicated.

EXAMPLES

The examples provided herein are not intended to be limiting, and are provided to demonstrate aspects of the present technology.

Example 1: Supplementation with *L. reuteri*

Study Design

The inventors designed and conducted a randomized, double-blinded, placebo-controlled clinical trial (flowchart, FIG. 1). In this trial, the inventors randomly assigned enrolled PWS participants, with a 1:1 ratio, to either the probiotics or placebo group. The inventors anticipated that a 12-week treatment period would be sufficient for probiotics supplementation to induce detectable changes. To achieve a statistical power of 80% for primary outcomes with a large effect size of 0.8 (Cohen's d) assumed, a total of 52 participants (26 in each arm) were required. We enrolled and randomized 71 subjects (Probiotics group=37, Placebo group=34), 56 of them (Probiotics group=28, Placebo group=28) finished 12-week trial who were included in the final intention-treat data analysis.

Ethical Considerations

Ethical Approval was issued by the Internal Review Board (IRB) of the Second Affiliated Hospital of Kunming Medical University (Review-YJ-2016-06). Clinical Trial of Probiotics was registered at the Chinese Clinical Trial Registry (ChiCTR), with a number ChiCTR1900022646. Signed informed consent was obtained from the parents or legal guardians of the subjects according to the IRB requirements. The study was conducted in accordance with the Declaration of Helsinki.

Participants

Study participants were recruited through the PWS Care & Support Center, located in Zhejiang, China. Participants were included if they met the following criteria: they had been genetically confirmed to have PWS; had not been administered any forms of probiotics for at least 4 weeks; had stable medications for at least 4 weeks; had no planned changes in medications or psychosocial interventions during the trial; had a willingness to provide stool samples in a timely manner; and had a willingness to cooperate with interviews and study procedures. Potential participants were excluded if they had other known genetic disorders, or if they were pregnant or breast-feeding before the study.

Randomization and Blinding

Randomization and allocation concealment were performed by a statistician who was not part of the research team. Randomization sampling numbers were electronically generated for each de-identified subject. Coded probiotics and placebo of identical appearance were prepared by Beijing Huayuan Academy of Biotechnology to ensure allocation concealment. Both the participants and the research staff/investigators who collected and analyzed the outcome data were blinded to treatment status. Blinding was also maintained by making the probiotics package appear identical to the placebo sachet.

Intervention

Probiotics LR-99 (Beijing Huayuan Academy of Biotechnology) was used in the study in the format of a sachet. Each sachet of probiotics supplement contained $3\times10^{10}$ colony forming units (CFUs). The placebo was maltodextrin in the sachet with similar color, flavor, and taste as the probiotic sachets. Subjects received 1 sachet twice a day of either probiotics or placebo for a duration of 12 weeks. Notably, probiotics are supplements, with minimal adverse effects. Placebo maltodextrin also has minimal adverse effects.

Primary Outcomes:

1. Weight and height measurements were obtained by parents using standard scales and collected by the research staff. BMI calculated by weight and height was converted to z-score using age growth references provided by WHO (2006).
2. Psychological measurements (a) Ages and Stages Questionnaires, 3rd Edition (ASQ-3). The ASQ-3 is one of the most widely available development screening tools for young children. The ASQ-3 has five domains: communication, gross motor, fine motor, problem-solving, and personal-social (Squires J 2009). Total scores were calculated. We interviewed all subjects younger than 5 years old.

(b) Gilliam Autism Rating Scale Third Edition (GARS-3) (Gilliam J E). It consists of 56 items describing characteristic behaviors of individuals with autism. The items are grouped into six subscales: restrictive, repetitive behaviors (RRB), social interaction (SI), social communication (SC), emotional responses (ER), cognitive style (CS), and maladaptive speech (MS). Total scores and subscales were calculated. We interviewed all subjects older than 3 years old.

Secondary Outcomes:

1. Fecal Microbiome (a) Sample Handling and Collection

Stool samples were collected with DNA/RNA shield faecal collection tubes (Zymo, Cat #R1101) containing 1 mL preservation solution and were transported to the laboratory by ice bags and then frozen at −80° C. TIANmap stool DNA kit was used to extract DNA (TIANGEN, Cat #DP328) according to the manufacturer's instructions, and DNA samples were carefully quantified with a Nanodrop Spectrophotometer. A260/A280 ratios were also measured to confirm high-purity DNA yield. DNA samples were frozen at −20° C. until use.

(b) 16S rRNA Gene Amplicon Sequencing

The 16S rRNA V3-V4 library was constructed by two rounds of PCR with the following primers: 341F: 5'TCGTCGGCAGCGTCAGATGTGTATAAGA-GACAGCCTACGGGAGGCAGCAGC CTACGGG-NBGCASCAG3' (SEQ ID NO: 1) and 805R: 5'GTCTCGTGGGCTCGGAGATGTGTATAAGAGA CAGTGACTACNVGGGTATCTA ATCC3' (SEQ ID NO: 2) via reaction procedure (95° C. for 2 min, followed by 25 cycles at 95° C. for 30 s, 55° C. for 30 s, and 72° C. for 30 s, and a final extension at 72° C. for 5 min). PCR products were purified with 1×KAPA AMPure beads (KAPA, Cat #KK8002). Then, products were put through a second PCR reaction procedure (95° C. for 2 min, followed by 8 cycles at 95° C. for 30 s, 55° C. for 30 s, and 72° C. for 30 s, and a final extension at 72° C. for 5 min). PCR products were purified with 1×KAPA AMPure beads and analyzed using a Bioanalyzer DNA kit, followed by quantification with real-time PCR. DNA libraries were pooled and sequenced on Illumina MiSeq (Illumina; CA) using a 2×250 bp paired-end protocol with overlapping reads.

Statistical Analysis

All raw data were recorded and processed in Microsoft Excel 2007 and R. The presentation of data follows the CONSORT recommendations for reporting results of Randomised Clinical Trials (RCTs). Statistical procedures were carried out using $\alpha=0.05$ as the significance level.

Receiver operated characteristic (ROC) curves were constructed via the plotROC package for multiple logistic regression models using either select clinical or predictive functional profiling indices.

The Wilcoxon rank-sum test was applied to explore the intergroup differences in the z-scores of weight, height, total scores and sub-scores of ASQ-3, GARS-3, ABC, and SRS at baseline, per-subject changes from 0 to 6 weeks, and per-subject changes from 6 to 12 weeks.

Primary outcomes were analyzed using linear mixed effect models (LME) to assess for differences within each primary outcome over the course of the study (0-6 weeks, 6-12 weeks, and 0-12 weeks) for each group. For all LME analyses, time, age, and gender were included as fixed effects and a random intercept to account for within-subject correlation due to repeated measures overtime. In the case of a significant main effect, Bonferroni-corrected pairwise comparisons were conducted.

Secondary outcomes were analyzed using similar methods as that of primary outcomes. In addition, linear regression was performed to check for correlations between clinical indices and microbiome compositions.

Microbiome Data Processing and Analysis

The sequencing reads were filtered using the QIIME2 (v2019.10) based on quality scores (Bolyen E 2019). Deblur was used to de-noise with default parameters and obtain an abundance table of samples by amplicon sequence variants (ASVs) Amir A 2017).

Alpha diversities were calculated with QIIME2. Bray-Curtis distance was used to characterize microbiome beta diversity. Taxonomies for ASVs were assigned using the sklearn-based taxonomy classifier trained on the sequences at 99% similarity level from Greengenes v13.8. Significant differences in the relative abundance of microbial phyla, genera, and alpha diversity between placebo and probiotics groups were identified by Kruskal-Wallis tests. A false discovery rate (FDR) based on the Benjamini-Hochberg (BH) adjustment was applied for multiple comparisons (jiang J 2017).

PICSRUSt-2 was used to infer microbial functional content based on ASVs' abundant tables and then produced Kyoto Encyclopedia of Genes and Genomes (KEGG) orthologs (KO), Enzyme Classification numbers, and pathway abundance table (Douglas G M, Czech L). The differential analyses were performed on the fold ratios between probiotics and placebo group with a permutation-based nonparametric test, and the top differential features were rendered and plotted with Calour (Xu Z Z). All 16S rRNA raw data is pending to be submitted to NCBI Sequence Read Archive (SRA).

Results

1. Demographic Features of PWS Participants

Figure 2:
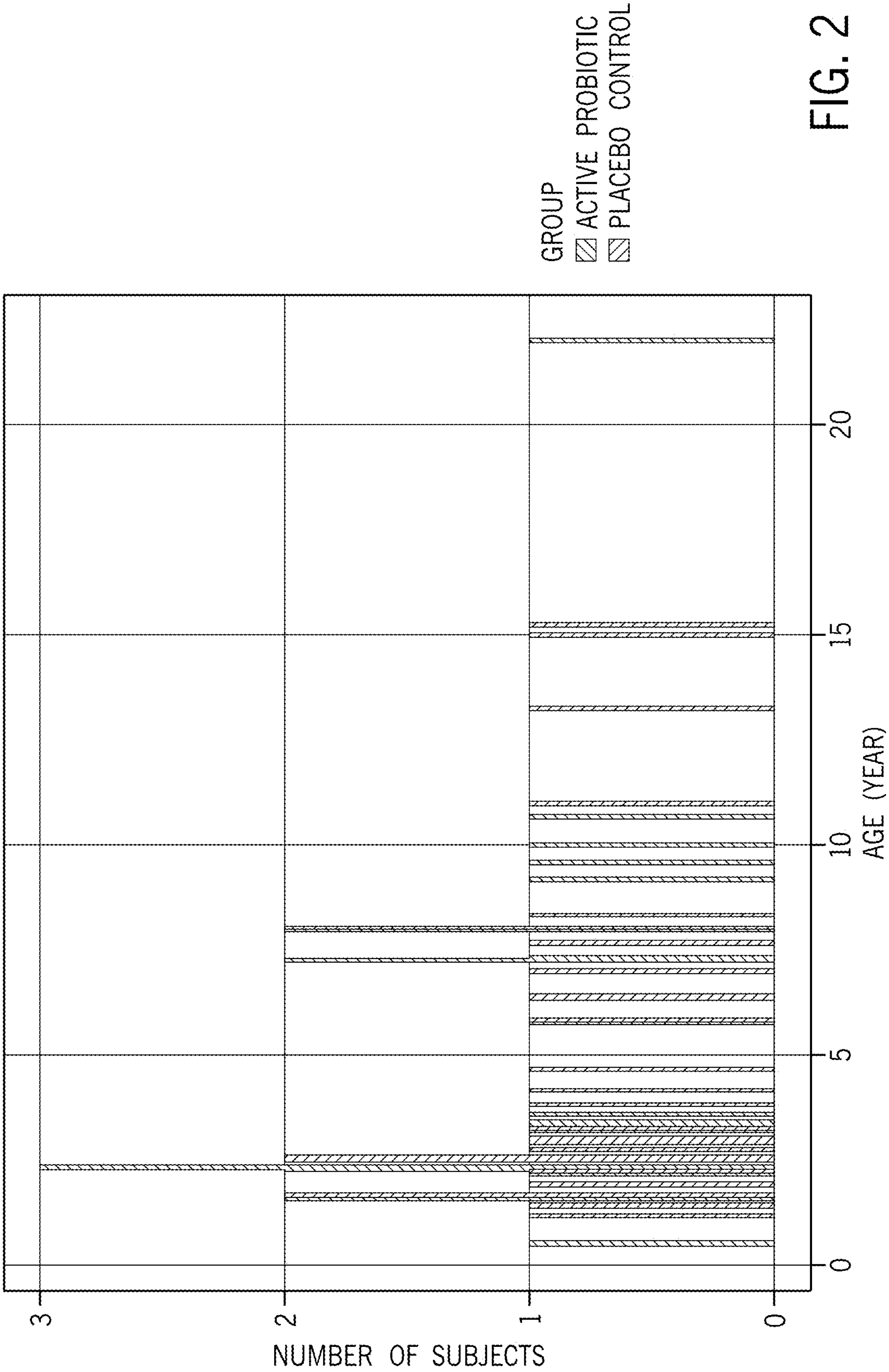
FIG. 2. Study participant age distribution for the study on *L. reuteri*. Participant groups are indicated by the color of the frequency bar. The age of subjects receiving placebo control ranges from 1 to 15 years while those receiving the active probiotic have ages ranging from 0.5 to 23 years.

The study included a total of 71 subjects aged 64.4±51.0 months (ranging from 6-264 months) with genetically confirmed diagnosis of Prader-Willi syndrome. Of which, 37 subjects aged 65.0±53.8 months were randomized to receive active probiotic, *L. reuteri*, while 34 subjects aged 64.0±49.0 months were randomized to receive placebo. An overview of the subject age distribution is shown in FIG. 2. Additionally, due to difficulties in data collection, a total of 56 subjects (n=28 in each arm) have available baseline clinical indices. Group-wise comparisons of baseline age, sex, genotype, and other characteristics did not indicate any significant differences (P>0.05). Detailed demographic characteristics of the enrolled participants are summarized in Table 1.

TABLE 1

Demographic features and baseline characteristics of study participants.

| | | Active Probiotic (N = 37) | Placebo Control (N = 34) | P-value |
|---|---|---|---|---|
| Age (months, n (mean ± SD)) | All Subjects | 28 (65 ± 53.8) | 28 (64 ± 49.0) | 1.00 |
| | >5 years | 12 (113 ± 50.2) | 11 (113 ± 42.7) | 0.81 |
| | ≤5 years | 16 (29 ± 9.8) | 17 (32 ± 11.5) | 0.52 |
| Sex (n (%)) | Male | 12 (43%) | 18 (64%) | 0.18 |
| | Female | 16 (57%) | 10 (36%) | |
| Genotype (n (%)) | Deletion | 16 (57%) | 15 (54%) | 0.56 |
| | Disomy | 4 (14%) | 2 (7%) | |
| | Other/Unknown | 8 (29%) | 11 (39%) | |
| Weight (kg, mean ± SD) | | 25.8 ± 15.3 | 26.2 ± 21.0 | 0.71 |
| Height (cm, mean ± SD) | | 109.6 ± 23.9 | 107.2 ± 26.6 | 0.66 |
| BMI (mean ± SD) | | 19.3 ± 4.58 | 19.7 ± 6.87 | 0.53 |

The study recruitment procedure and dropouts at each study time point are illustrated as a flowchart in FIG. 1. No serious or severe adverse events were observed. There were no significant differences found between the two groups for experiencing any observed adverse events (P>0.05). Of 71 initially enrolled subjects, 15 dropped over the course of the trial. Eight subjects were dropped due to antibiotics use, which led to termination; seven of those dropped were due to self-withdrawal; none of those dropped were due to adverse effects (FIG. 1).

2. Effects of Probiotics on BMI and Psychological Measurements

To assess for groupwise longitudinal changes in primary outcomes, we applied Bonferroni-corrected pairwise comparisons on linear mixed effects models, using age, gender, and study timepoint as fixed effects and the subject as a random intercept to account for repeated measures over time. The estimated marginal means of BMI at each study visit is shown per group as a table in FIG. 3. Based on such an analysis, we determined that subjects receiving active probiotic display a significant reduction in BMI. Specifically, such significant differences are uniquely observed in the active probiotic group for BMI between baseline and week 6, and between baseline and week 12 (FIG. 4, P<0.05).

Group-wise comparisons of psychological assessment scores were performed at weeks 6 and 12 via the Wilcoxon rank-sum test. A summary of psychological assessment scores, including GARS-3 and ASQ-3, as well as associated statistics for both groups at weeks 6 and 12 is provided in FIG. 5. Such results suggest that *L. reuteri* LR-99 significantly reduced the BMI in subjects receiving the active probiotic compared to those receiving placebo at both 6 weeks (P<0.05) and 12 weeks (P<0.01) of the treatment relative to measures at baseline.

3. Changes in Microbiome Composition and Function with Probiotics Intervention

Figure 6A:
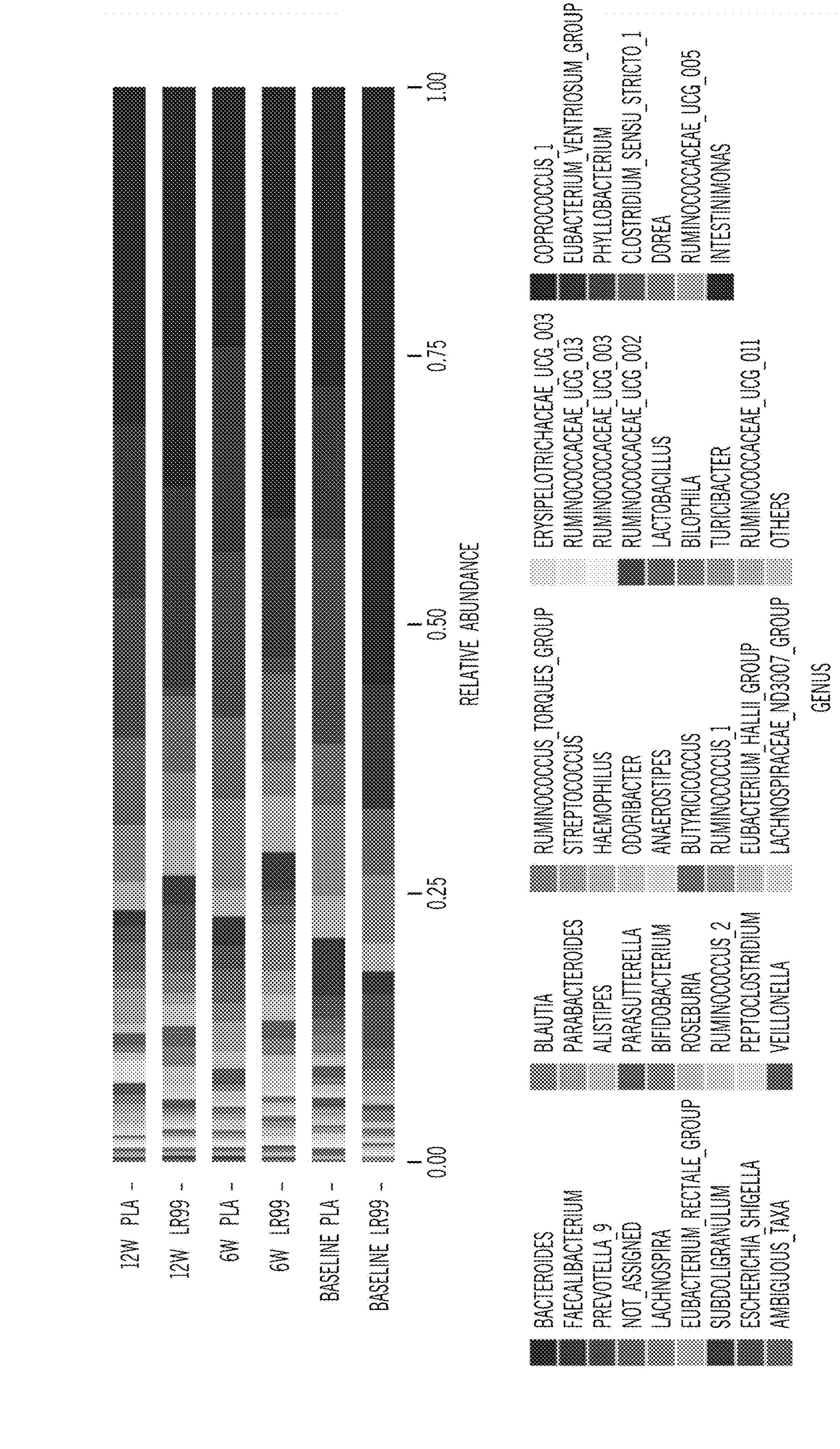
FIG. 6A-6C. Overview of genus level relative abundances and measures of microbial diversity for the study on *L. reuteri*. (A) Relative abundance plots of the gut microbiota at baseline, 6 weeks, and 12 weeks at the genus level. (B) Mean α diversity measured via Shannon, Simpson, ACE, and Chao1 indices. (C) β diversity with Principal Coordinates Analysis (PCoA) score plots of gut microbial data based on a Bray-Curtis dissimilarity matrix.

After sequencing, we obtained a total of 3198401 raw reads and an average of 49206.169 reads per sample (ranging from 29501-71027 reads per sample). Overall phylum and genus level variations in gut microbiota composition over the intervention course are shown in FIG. 6A for both probiotics and placebo groups.

Figure 6B:
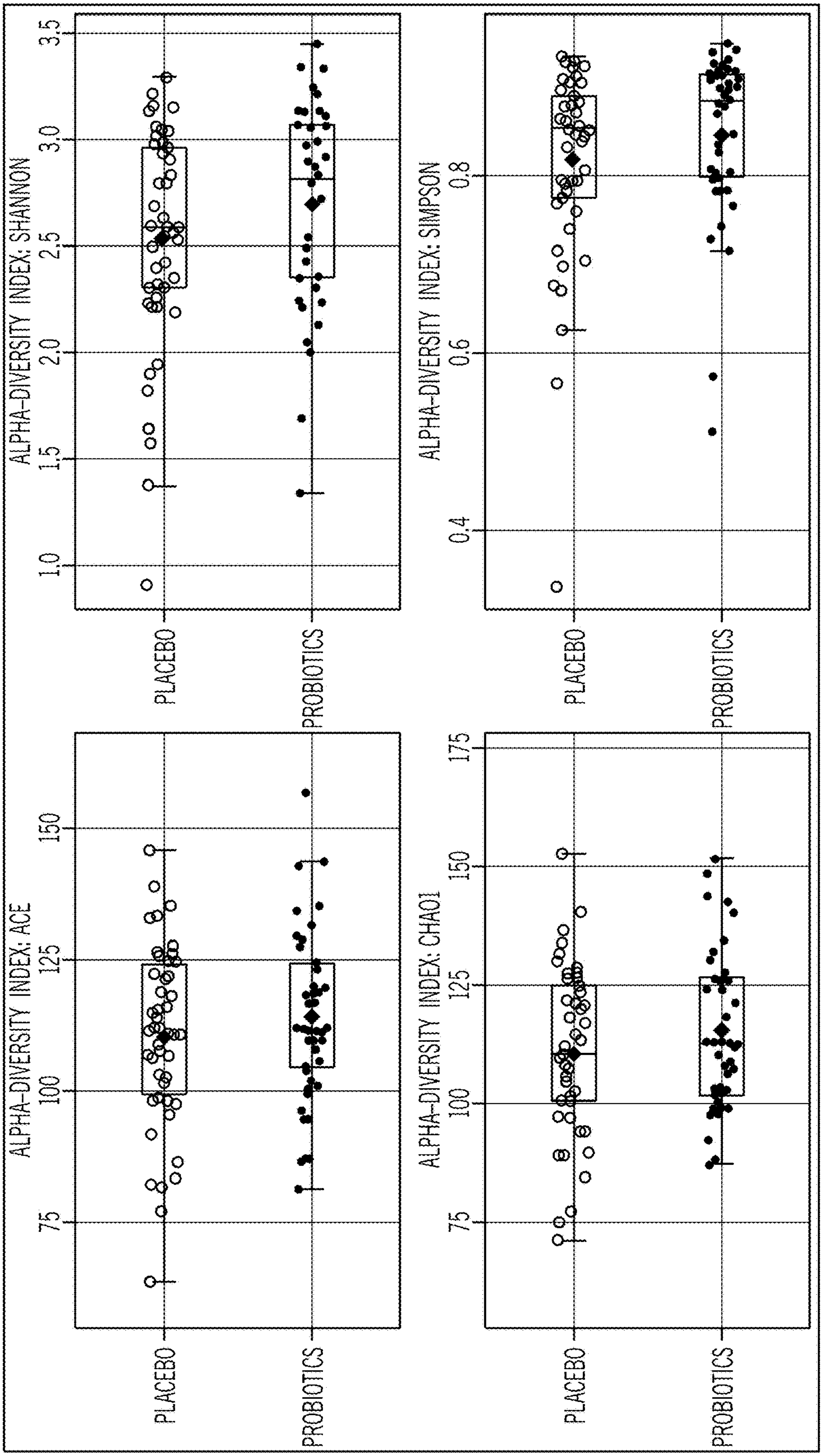
Figure 6C:
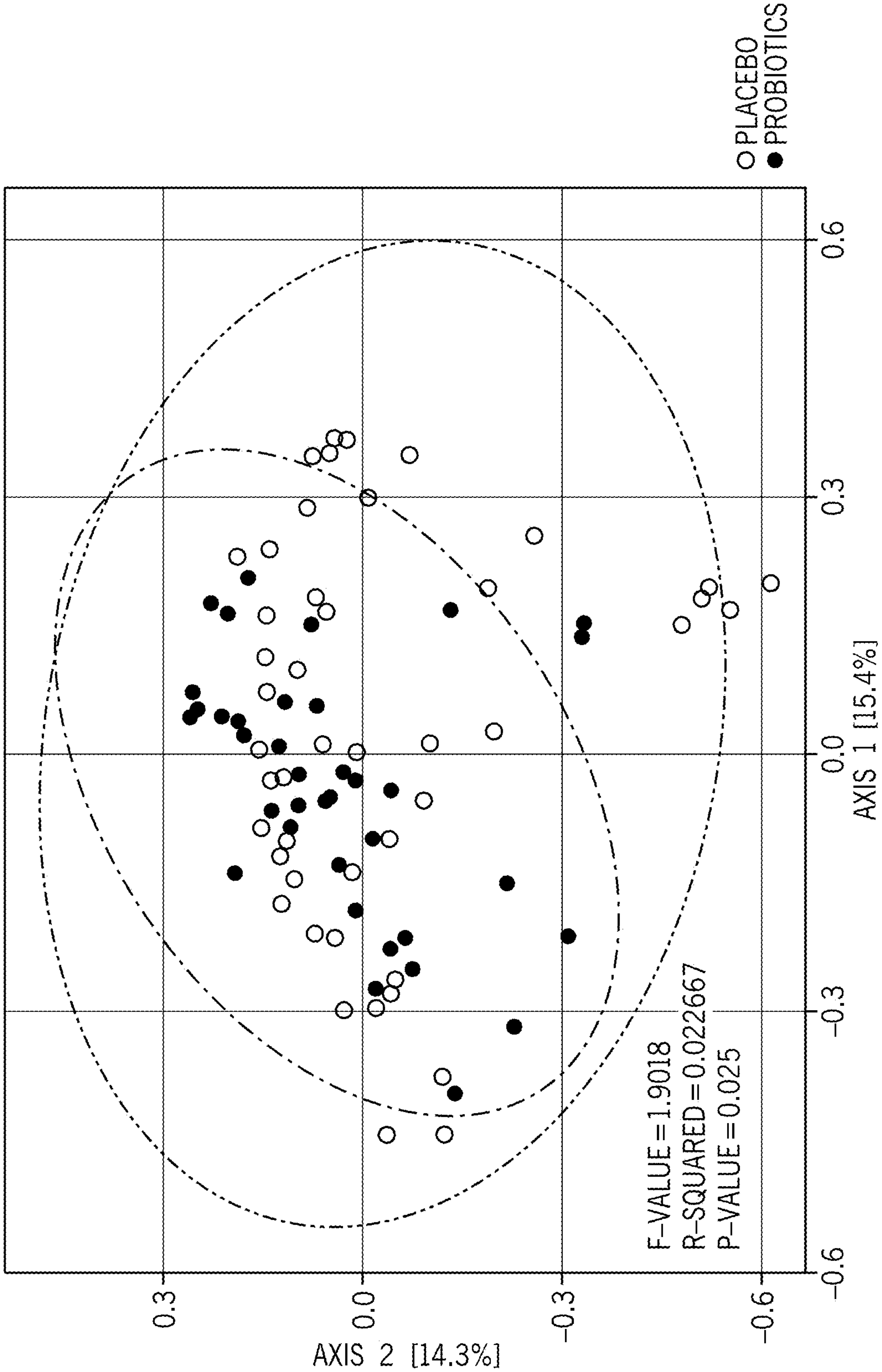
Figure 7A:
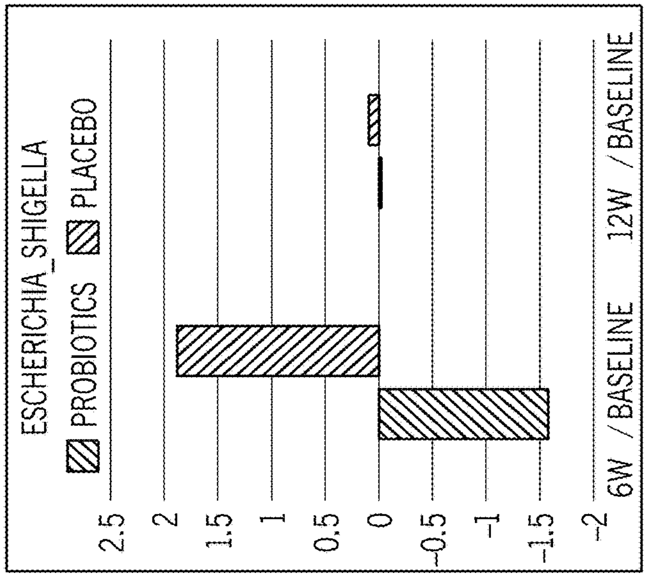
FIG. 7A-7I. Fold change of relative abundance at genus level over the course of intervention for the probiotics group (green) and placebo (blue) for the study on *L. reuteri*. Each bar represents the log 2-transformed relative change of gut microbial abundance of 6 and 12 weeks compared with the baseline.
Figure 7B:
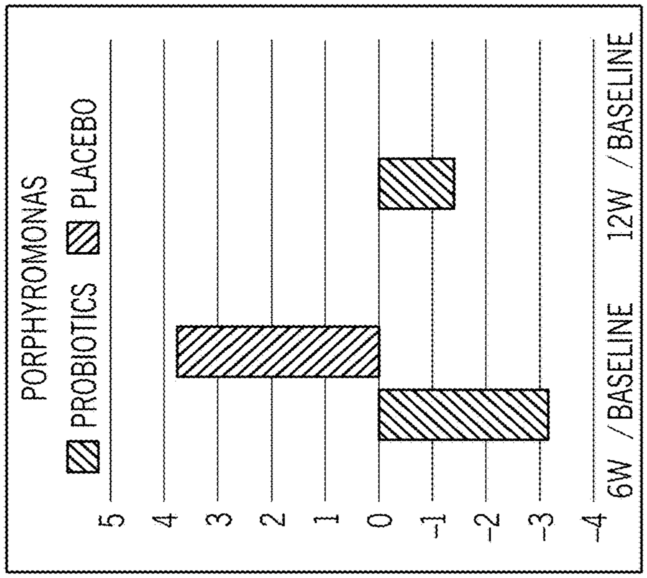
Figure 7C:
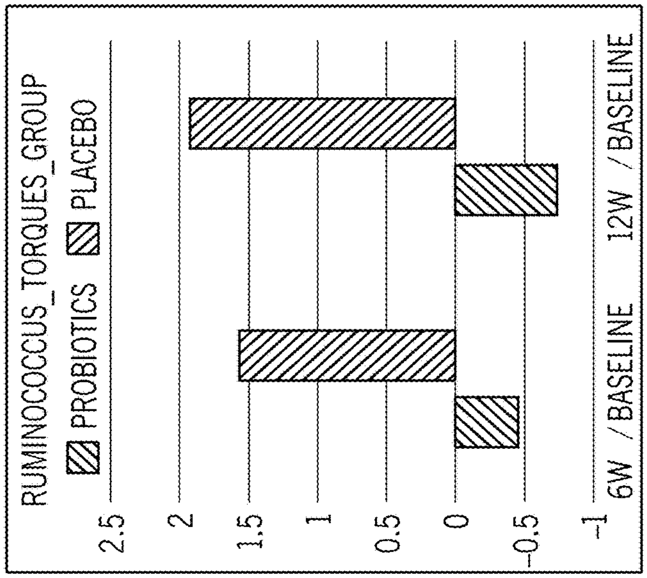
Figure 7D:
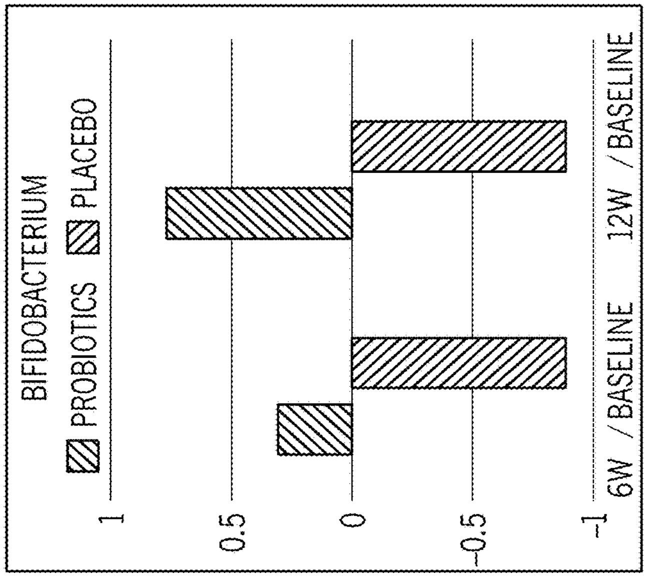
Figure 7E:
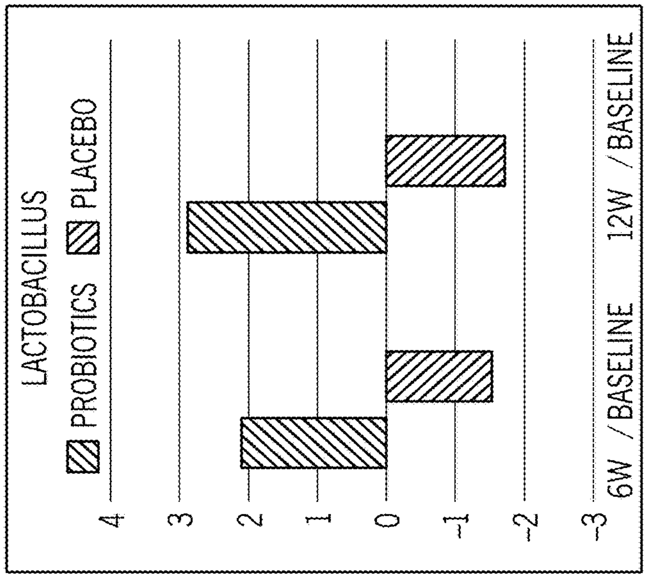
Figure 7F:
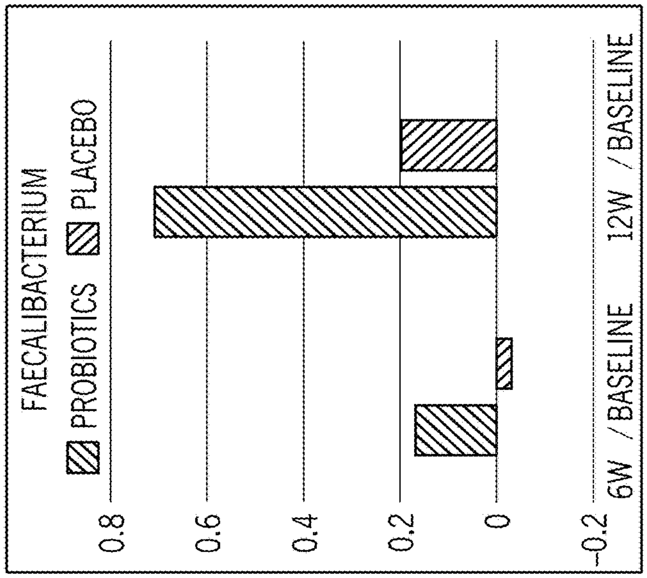
Figure 7G:
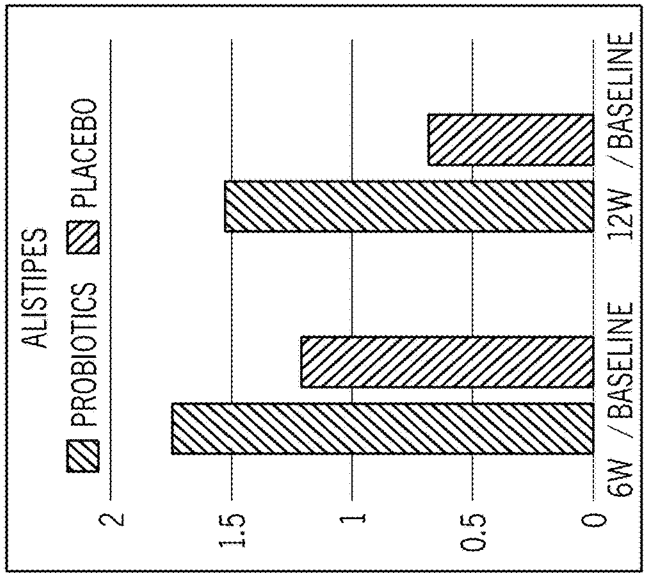
Figure 7H:
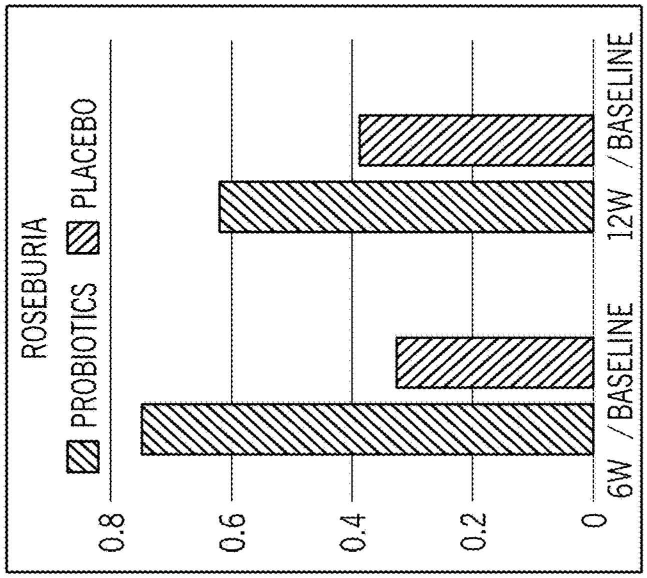
Figure 7I:
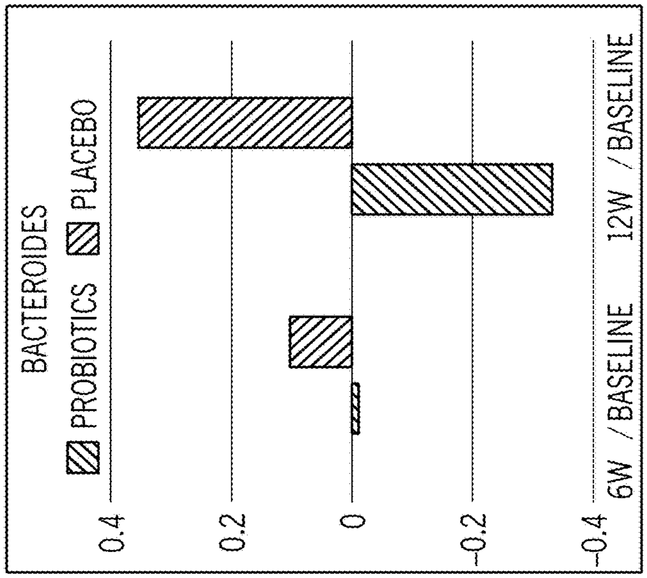

Overall, α diversity determined using Shannon, Simpson, ACE, and Chao1 indices did not show any significant group-wise differences (FIG. 6B). However, β diversity showed a significant separation with probiotics treatment via permutational multivariate ANOVA (PERMANOVA, F-statistic=1.9018; $R^2$=0.022667; P<0.05, FIG. 6C).

To characterize the change in abundance of potentially clinically significant bacteria over the intervention course, we calculated the Log 2-fold changes of detected and identified gut microbiota. Fold changes of gut microbiota abundance agglomerated at the genus levels are presented in FIG. 7.

In an attempt to elucidate the changes in the gut microbiome functional profile between those receiving active probiotic and those receiving placebo, we applied predictive functional profiling and performed group-wise comparisons of mean abundance differences for each identified functional pathway. Several functional pathways were determined to be differentially expressed among subjects receiving active probiotic (FIG. 8, Q-value<0.1).

Figure 9A:
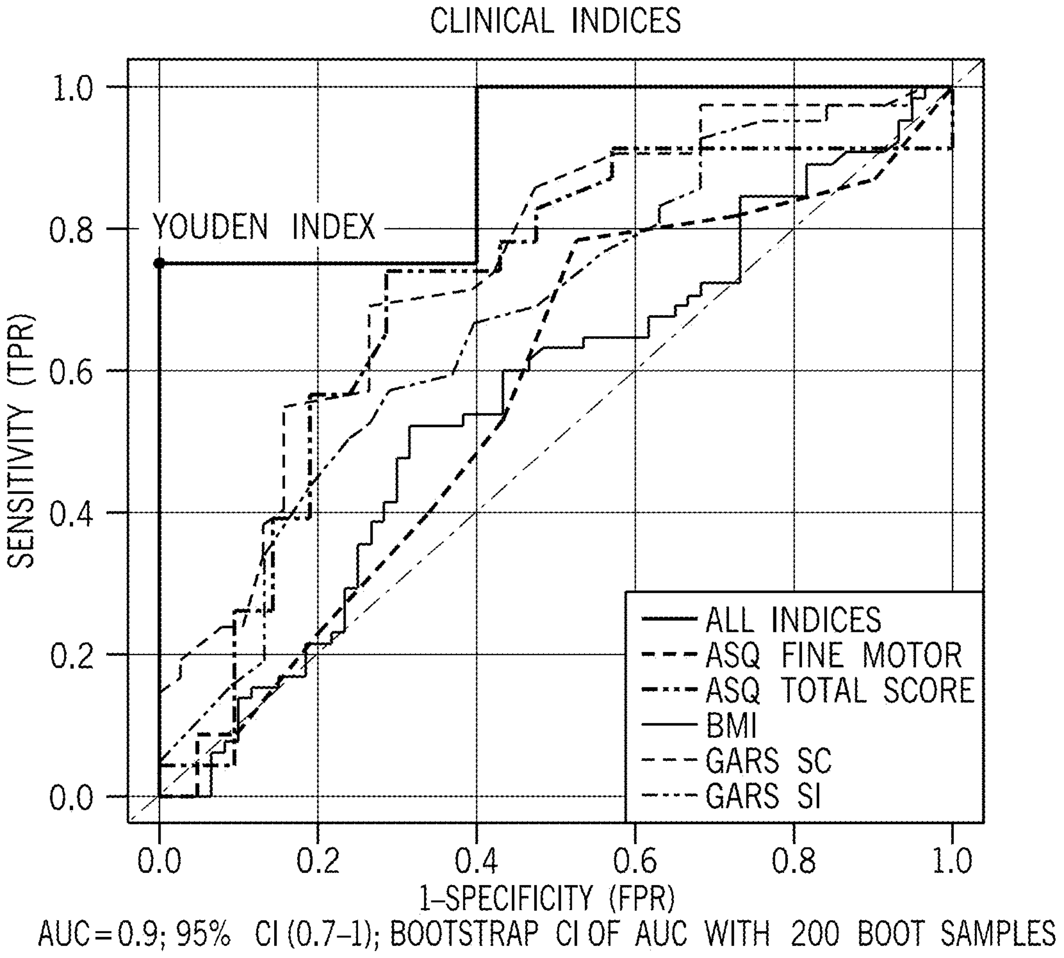
FIG. 9A-9B. ROC curve of classification between treatment and placebo groups based on select clinical indices and functional metagenomic features using logistic regression for the study on *L. reuteri*. (A) Classification using clinical indices, including ASQ-3 total and fine motor scores and GARS-3 SC and SI scores. (B) Classification using select functional features of the gut metagenome.
Figure 9B:
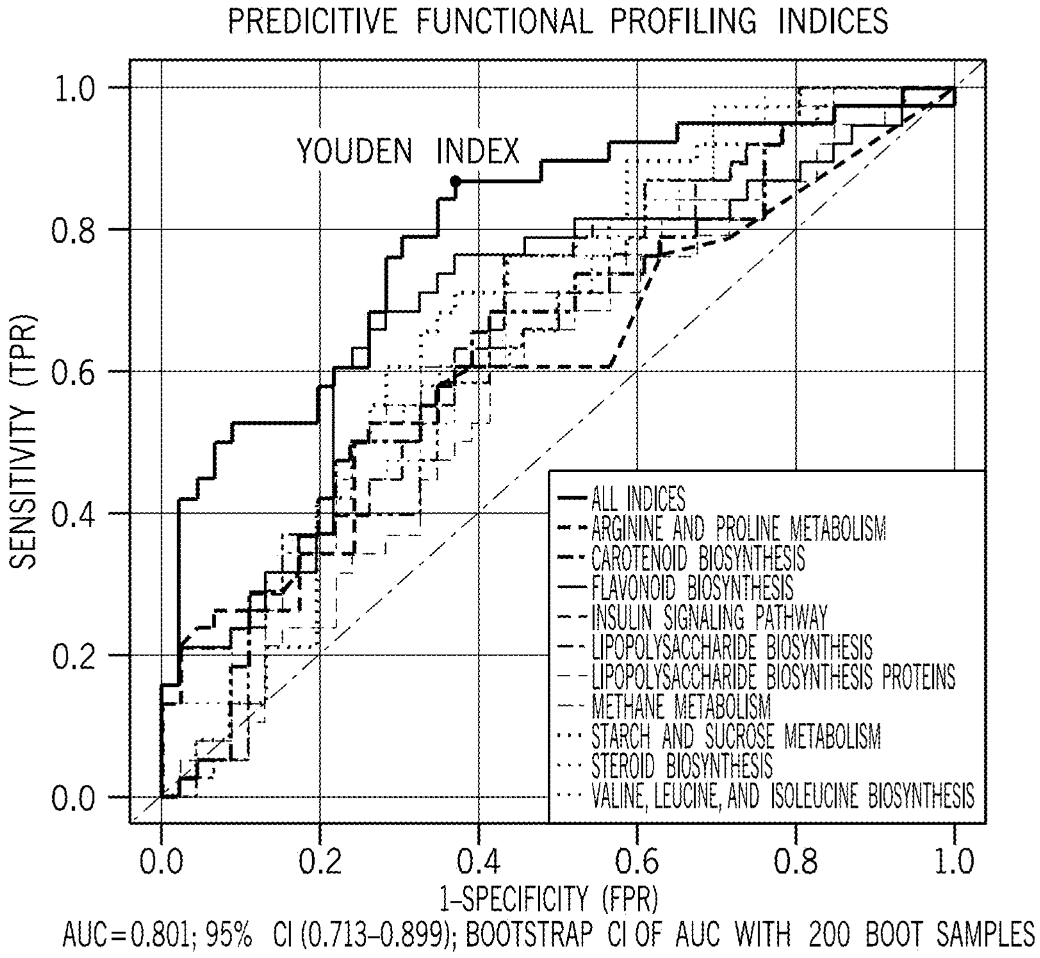

Subsequently, using receiver operated characteristic (ROC) curve analysis, we identified the significant clinical parameters (BMI, social communication, social interaction, total ASQ, fine motor) that can be used as biomarkers for treatment response and characterize subjects either receiving probiotics or placebo (FIG. 9A); the fitted logistic regression model is summarized in the table provided as FIG. 10. We then identified several key metagenomic functional pathways that can be used to characterize subjects receiving either active probiotics or placebo (FIG. 9B); the fitted logistic regression model is summarized in the table provided as FIG. 11. Classification using clinical indices, including ASQ-3 total and fine motor scores and GARS-3 SC and SI scores, resulted in an AUC of 0.9 (95% CI=0.7-1). Similarly, classification using select functional features of the gut metagenome resulted in an AUC of 0.801 (95% CI=0.713-0.899).

As several strains of *Lactobacillus* are known probiotics to have protective effects against weight gain in humans and has been found to inhibit proinflammatory interleukin activity linked to obesity and poor obesity-related outcomes,(Cox et al., 2015; Rosing et al., 2017a) the observed reduction in BMI and improvement in social function among subject receiving the active probiotic is consistent with expectations. However, due to the lack of literature support, improvements in fine motor function, overall development, and alterations in the predicted metagenomic functional profile are surprising results that were unexpected.

4. Correlation Between Gut Microbiota Abundances and Clinical Indices

Associations between family and genus level microbiota abundances and clinical indices were assessed via MaAsLin2 as univariate linear correlations. Significant correlations at the family and genus levels against clinical indices for measurements at weeks 6 and 12 combined are reported in the table presented as FIG. 12.

Discussion

In our 12-week, randomized, double-blind, placebo-controlled trial of 71 subjects with PWS, *L. reuteri* LR-99 significantly reduced the BMI in those receiving the active probiotic compared to those receiving placebo at both 6 weeks (P<0.05) and 12 weeks (P<0.01) of the treatment relative to measures at baseline.

In the past, interventions with *L. reuteri* have failed to elicit improvements in BMI in humans (Maes M et al, Agusti A et al). Such novel findings in this study provides a new avenue of PWS early intervention to prevent obesity and related complications. This is important for early intervention as among all subjects of this study cohort, more than half of the subjects are aged less than 5 years old. In past studies, other strains of *L. Reuteri*, such as *L. Reuteri* 263, have demonstrated anti-obesity effects associated with energy metabolism remodeling of white adipose tissue in high-energy-diet-fed rats (Chen L H). *L. Reuteri* SD5865 has been shown to improve incretin and insulin secretion in glucose-tolerant humans (Simons M C). Another strain, *L. reuteri* V3401, was reported to improve metabolic syndrome in adult because it reduces inflammatory biomarkers and modifies the gastrointestinal microbiome (Tenorio-Jimenez). PWS individuals were found to have absolute or functional Growth Hormone (GH) deficiency, and GH replacement is currently the most effective treatment for PWS (Zhu J L, Bakker N E). GH was found not only to increase height, but also decrease body fat and improve cognition, motor, and mental function (Bakker N E, Kuppens R J). With earlier initiation of GH treatment, increased efficacy and prognostic benefit have been observed (Bakker N E). One study found probiotics *L. reuteri* could increase growth hormone level in mice (Varian B J), which reveals a potential mechanism by which probiotics can reduce BMI and treat PWS patients: promotion of endogenous growth hormone release. Our findings warrant further investigation into the biological mechanisms of probiotics, a promising intervention for PWS with better tolerance and convenience than GH replacement (Onubi O J).

Interestingly, we found that *L. reuteri* intervention significantly improved social communication (P<0.01) and social interaction (P<0.05) compared to controls for those older than 3 years old. Moreover, we found a significant increase in total ASQ-3 score (P<0.05) and fine motor sub-scale (P<0.05) in *L. reuteri* intervention group compared with placebo control group when compared at the last study visit (week 12).

These novel and important findings opened new avenues of using probiotics to improve BMI, social function, fine motor function, and overall developmental milestones in those affected children with PWS. As previously mentioned, researchers have reported in the past that *L. reuteri* upregulates the neuropeptide hormone oxytocin (OXT), a factor integral in social bonding and reproduction (Poutahidis T). OXT-producing cells were found to be increased in the caudal paraventricular nucleus (PVN) of the hypothalamus after feeding of a sterile lysed preparation of *L. reuteri* (Varian B). Further studies indicated that *L. reuteri* rescues social interaction-induced synaptic plasticity in the ventral tegmental area of ASD mice, but not in oxytocin receptor-deficient mice (Sqritta M). Oxytocin nasal spray has been used to treat PWS subjects with beneficial effects (Zhu J), use of *L. reuteri* which could induce endogenous oxytocin release will be more cost effective, convenient, and potentially longer lasting than using oxytocin directly. This finding warrants further study of the internal mechanism via oxytocin or other neurotransmitters/hormones involved in pathogenesis of PWS and its co-morbidities. In terms of the observed improvement of overall development (via BMI, P<0.05), fine motor function (P<0.05) and also possible problem solving skill (P=0.051) with probiotics, we have not found any literature reports in these regards. These findings are very supportive of probiotic use as a valuable early intervention to improve the overall developmental level and therefore change the prognosis of those with PWS. Further studies in these areas are indicated.

The microbiome composition changes we observed with the intervention have been previously linked to weight reduction and inflammatory attenuation. Notably, we found a significant separation of the gut microbiome β-diversity between the probiotics and the placebo group after treatment. Baseline β-diversity has been directly correlated with long-term weight loss when adhering to a controlled diet (Grembi J A). Therefore, probiotics supplementation may have preventative effects or may facilitate diet-induced weight reduction. As previous studies on *Lactobacillus* probiotic supplementation in healthy individuals have shown to modulate the overall gut microbiome composition, (Ferrario et al., 2014) such changes in the gut microbial diversity following supplementation with *L. reuteri* is consistent with expectations.

After administration of *L. reuteri*, we also noted a trend of reduction in the abundance of several bacterial including *Escherichia-Shigella, Porphyromonas* and *Ruminococcus torques*. *Escherichia-Shigella* is well recognized pathogenic bacteria that is enriched in individuals with obesity and type 2 diabetes (Anhê, F. F, Thingolm L B), and is also enriched in autism and related to its constipation (Eshraghi R S). The role of periodontal pathogens, notably *Porphyromonas gingivalis* (*P. gingivalis*), in the onset or exacerbation of systemic diseases has been proposed (Mulhall H). *Ruminococcus torques* is one of the prominent species in IBD enriched in gut dysbiosis (Lloyd-Price, J). *Bacteroides* was found to be enriched in subjects with type 1 and II diabetes (Alkanani A. K, Remely M), however some controversial results reported for the anti-inflammatory effects of *Bacteroides* (Hiippala K). These findings were demonstrated only in probiotics treatment group, not in the placebo group in PWS patients. This indicated that the probiotics we used can significantly change the gut microbiome composition, further change gut and brain function through their anti-inflammatory effects and gut brain axis signaling.

Conversely, *Bifidobacterium, Lactobacillus, Faecalibacteria, Roseburia* and *Alistipes* were increased in the gut after LR-99 treatment. *Lactobacillus*, the genus to which the interventional probiotic belongs, has protective effects against weight gain in humans, and also has been found to inhibit the activity of proinflammatory interleukins, which have been linked to obesity and poor obesity-related outcomes (Rosing J A, Cox A J). *Bifidobacterium* is widely regarded as beneficial to gut health and weight reduction (Pedret A, Uusitupa H-M). *Alistipes* abundance was inversely correlated to adiposity, lipid and glucose homeostasis parameters (Garcia-Ribera S, 2020). *Roseburia* is more abundant in the microbiome of pregnant women with ketonuria which correlates increased maternal lipid metabolism and reduced glucose levels (Robinson H), *Roseburia* and *Faecalibacteria* are butyrate-producing bacteria which is anti-inflammatory, *Faecalibacteria* was found to decrease gut permeability and lower inflammation (Mörkl S, et al). These findings were demonstrated only in probiotics treatment group, not in the placebo group in PWS patients. This indicated that the probiotics we used can significantly change the gut microbiome composition, further change gut and brain function through their active metabolites influenced fat metabolism and gut brain axis signaling.

Furthermore, using predictive functional gene analysis, we identified a significant upregulation of calcium signaling pathway, flavonoid biosynthesis, carotenoid biosynthesis, steroid biosynthesis, N-glycan biosynthesis, photosynthesis, valine, leucine, isoleucine biosynthesis and meiosis (yeast), with both P- and Q-values are both <0.05. Calcium signal pathway is critical for regulation of obesity (Song Z); Flavonoids are signature classes of secondary metabolites formed from a relatively simple collection of scaffolds. They are extensively decorated by chemical reactions including glycosylation, methylation, and acylation (Tobge T, Jiang T). Carotenoid, an antioxidant, previously found to have beneficial effects on obesity and obesity-associated pathologies (Mounien L); Steroid biosynthesis favors anti-inflammation and stress response (Chatuphonprasert W); N-glycan biosynthesis promotes immune modulation and anti-inflammation (Reily C). Dietary supplementation with Leu or Ile reduced body weight by regulating lipid metabolism-related genes, insulin sensitivity and hepatic steatosis impaired by HFD were alleviated after Leu or Ile supplementation (Ma Q). Valine, leucine, isoleucine refer as branched-chain amino acids (BCAAs). BCAA supplementation has been used in patients (Garcia-Cazorla A) with BCKDK deficiency to successfully reduce ASD symptoms and improve cognitive function. These findings were demonstrated only in probiotics treatment group, not in the placebo group in PWS patients. This indicated that the probiotics we used can significantly change the gut microbiome composition, further change gut and brain function through their anti-inflammatory effects, reduce gut permeability, reduce cytokines and influence gut brain axis signaling.

Insulin signaling pathway and starch and sucrose metabolism were also found to be upregulated with P<0.05, but Q>0.1. The insulin transduction pathway is a biochemical pathway by which insulin increases the uptake of glucose into fat and muscle cells and reduces the synthesis of glucose in the liver and hence is involved in maintaining glucose homeostasis (Bevan P). The starch and sucrose metabolism pathways have been found to be down-regulated in ASD (Rose D R 2018). The human gut microbiome is a critical component of digestion, as it facilitates the breakdown of complex carbohydrates and proteins (Oliphant, K 2019). As such, while it is likely that such functional changes in the fecal metagenome can be beneficial to the host, the underlying mechanistic role of such changes in the gut microbiome remain unclear.

The predictive functional gene analysis also showed the significant downregulation of arachidonic acid metabolism with both P and Q<0.05. Arachidonic acid metabolism is involved in inflammatory process (Violette Said Hanna, FA Kuehl Jr). Lipopolysaccharide (LPS) and phosphotransferase system (PTS) are also found to be down-regulated with P<0.05 but Q>0.05. Lipopolysaccharide (LPS), endotoxin from gram negative pathogenic bacteria such as *Escherichia_Shigella*, has been reported involved in causing obesity (Hersoug L G), autism and gut brain axis (Srikantha P). The phosphoenolpyruvate-dependent sugar phosphotransferase system (PTS) is a major carbohydrate transport system in bacteria. The PTS catalyses the phosphorylation of incoming sugar substrates and coupled with translocation across the cell membrane, makes the PTS a link between the uptake and metabolism of sugars (Postmna P W, Meadow N D). Taken together, the microbiome composition data and predictive functional gene analysis indicate that the diversity separation caused by LR-99 probiotics treatment favors protection against obesity and obesity-related pathology.

Furthermore, using receiver operated characteristic (ROC) curve analysis, we found the clinical indices, including ASQ-3 total, fine motor scores and GARS-3 SC and SI scores, resulted in an AUC of 0.9 (95% CI=0.7-1). Similarly, classification using select functional features of the gut metagenome resulted in an AUC of 0.801 (95% CI=0.713-0.899). These further confirmed that our novel findings of improved clinical indices and gut microbiome by *L. reuteri* have high sensitivity and specificity to predict of the therapeutic response which was not seen in placebo group.

RRB is one of the core symptoms of Autism Spectrum Disorder (ASD), which has been reported in as many as 25-40% of PWS cases (Salehi P, Bennett J A). *Alitipes* was found to be negatively correlated with RRB; *Subdoligranulum* is positively correlated with BMI.

*Faecalibacterium* was negatively correlated with BMI. A decrease in the relative abundance of *Alistipes* (Strati F, Srikantha P) was found in ASD. *Subdoligranulum* was found to be increased in obese mice (Elmassry M M). Individuals with obesity have less abundance of *Faecali-*

*bacterium* (Crovesy, L). *Bifidobacterium* is negatively correlated with BMI as expected.

In conclusion, this randomized double blinded placebo control trial for PWS children showed that treatment with probiotic LR-99 for 12 weeks significantly decreased BMI at week 6 and has more pronounced effects when examined after 12 weeks of administration, significantly improved social communication and interaction, development especially fine motor function at week 12. These novel findings are with vital implications for early treatment in PWS. Probiotic treatment also altered microbiome composition and function to favor anti-obesity and anti-inflammation.

There are some limitations to the study that deserve consideration. First, despite our adoption of proper recruitment and retention strategies, PWS participant enrollment and retention for this trial were challenging, the sample size was relatively small and limited further subgroup analysis. Second, the broad age range used in this study resulted in high subject population heterogeneity and potentially variable treatment efficacy. Third, assessment of fecal microbiome was not controlled for dietary habits, which may influence the microbial abundances at the individual level. Thus, future studies with larger sample sizes, improved control for environmental factors, and subgroup stratification are warranted. Due to the limitations of the study listed above, further studies are warranted to investigate the mechanism and efficacy of LR-99 probiotics treatment in PWS.

REFERENCES

1. Cassidy S B, Schwartz S, Miller J L, Driscoll D J. Prader-Willi syndrome. Genetics in Medicine: Official Journal of the American College of Medical Genetics. 2012; 14(1):10-26. doi:10.1038/gim.0b013e31822bead0
2. Irizarry K A, Miller M, Freemark M, Haqq A M. Prader Willi Syndrome: Genetics, Metabolomics, Hormonal Function, and New Approaches to Therapy. Advances in Pediatrics. 2016; 63(1):47-77. doi:10.1016/j.yapd.2016.04.005
3. Butler M G, Manzardo A M, Forster J L. Prader-Willi Syndrome: Clinical Genetics and Diagnostic Aspects with Treatment Approaches. Current Pediatric Reviews. 2016; 12(2):136-166. doi:10.2174/1573396312666151123115250
4. Bakker N E, Lindberg A, Heissler J, Wollmann H A, Camacho-Hübner C, Hokken-Koelega A C, on behalf of the KIGS Steering Committee. Growth Hormone Treatment in Children With Prader-Willi Syndrome: Three Years of Longitudinal Data in Prepubertal Children and Adult Height Data From the KIGS Database. The Journal of Clinical Endocrinology & Metabolism. 2017; 102(5): 1702-1711. doi:10.1210/jc.2016-2962
5. Kuppens R J, Bakker N E, Siemensma E P C, Tummers-de Lind van Wijngaarden R F A, Donze S H, Festen D A M, van Alfen-van der Velden JAEM, Stijnen T, Hokken-Koelega A C S. Beneficial Effects of GH in Young Adults With Prader-Willi Syndrome: A 2-Year Crossover Trial. The Journal of Clinical Endocrinology & Metabolism. 2016; 101(11):4110-4116. doi:10.1210/jc.2016-2594
6. Junli Zhu B S, Xuejun Kong M D. Current Treatments of Prader-Willi Syndrome: A Systematic Review. North American Journal of Medicine and Science. 2017 [accessed 2020 Dec. 14]; 10(4). najms.com/index.php/najms/article/view/370
7. Olsson L M, Poitou C, Tremaroli V, Coupaye M, Aron-Wisnewsky J, Backhed F, Clement K, Caesar R. Gut microbiota of obese subjects with Prader-Willi syndrome is linked to metabolic health. Gut. 2020; 69(7):1229-1238. doi:10.1136/gutjnl-2019-319322
8. Aoun A, Darwish F, Hamod N. The Influence of the Gut Microbiome on Obesity in Adults and the Role of Probiotics, Prebiotics, and Synbiotics for Weight Loss. Preventive Nutrition and Food Science. 2020; 25(2):113-123. doi:10.3746/pnf.2020.25.2.113
9. Lv Y, Qin X, Jia H, Chen S, Sun W, Wang X. The association between gut microbiota composition and BMI in Chinese male college students, as analysed by next-generation sequencing. The British Journal of Nutrition. 2019; 122(9):986-995. doi:10.1017/S0007114519001909
10. Zhang C, Yin A, Li H, Wang R, Wu G, Shen J, Zhang M, Wang L, Hou Y, Ouyang H, et al. Dietary Modulation of Gut Microbiota Contributes to Alleviation of Both Genetic and Simple Obesity in Children. EBioMedicine. 2015; 2(8):968-984. doi:10.1016/j.ebiom.2015.07.007
11. Gomes A C, Hoffmann C, Mota J F. The human gut microbiota: Metabolism and perspective in obesity. Gut Microbes. 2018; 9(4):308-325. doi:10.1080/19490976.2018.1465157
12. Deng L, Wang R, Li H, Zhang C, Zhao L, Zhang M. miRNA-Gene Regulatory Network in Gnotobiotic Mice Stimulated by Dysbiotic Gut Microbiota Transplanted From a Genetically Obese Child. Frontiers in Microbiology. 2019; 10:1517. doi:10.3389/fmicb.2019.01517
13. Ke X, Walker A, Haange S-B, Lagkouvardos I, Liu Y, Schmitt-Kopplin P, von Bergen M, Jehmlich N, He X, Clavel T, et al. Synbiotic-driven improvement of metabolic disturbances is associated with changes in the gut microbiome in diet-induced obese mice. Molecular Metabolism. 2019; 22:96-109. doi:10.1016/j.molmet.2019.01.012
14. Hibberd A A, Yde C C, Ziegler M L, Honore A H, Saarinen M T, Lahtinen S, Stahl B, Jensen H M, Stenman L K. Probiotic or synbiotic alters the gut microbiota and metabolism in a randomised controlled trial of weight management in overweight adults. Beneficial Microbes. 2019; 10(2):121-135. doi:10.3920/BM2018.0028
15. Tenorio-Jimenez C, Martinez-Ramirez M J, Del Castillo-Codes I, Arraiza-Irigoyen C, Tercero-Lozano M, Camacho J, Chueca N, Garcia F, Olza J, Plaza-Diaz J, et al. *Lactobacillus reuteri* V3401 Reduces Inflammatory Biomarkers and Modifies the Gastrointestinal Microbiome in Adults with Metabolic Syndrome: The PROSIR Study. Nutrients. 2019; 11(8). doi:10.3390/nu11081761
16. West C L, Stanisz A M, Mao Y-K, Champagne-Jorgensen K, Bienenstock J, Kunze W A. Microvesicles from *Lactobacillus reuteri* (DSM-17938) completely reproduce modulation of gut motility by bacteria in mice. PloS One. 2020; 15(1):e0225481. doi:10.1371/journal-.pone.0225481
17. Simon M-C, Strassburger K, Nowotny B, Kolb H, Nowotny P, Burkart V, Zivehe F, Hwang J-H, Stehle P, Pacini G, et al. Intake of *Lactobacillus reuteri* improves incretin and insulin secretion in glucose-tolerant humans: a proof of concept. Diabetes Care. 2015; 38(10):1827-1834. doi:10.2337/dc14-2690
18. Chen L-H, Chen Y-H, Cheng K-C, Chien T-Y, Chan C-H, Tsao S-P, Huang H-Y. Antiobesity effect of *Lactobacillus reuteri* 263 associated with energy metabolism remodeling of white adipose tissue in high-energy-diet-fed rats. The Journal of Nutritional Biochemistry. 2018; 54:87-94. doi:10.1016/j.jnutbio.2017.11.004
19. Huerta-Ávila EE, Ramírez-Silva I, Torres-Sánchez LE, Díaz-Benítez CE, Orbe-Orihuela Y C, Lagunas-Martínez A, Galván-Portillo M, Flores M, Cruz M, Burguete-García AI. High Relative Abundance of *Lactobacillus reuteri* and Fructose Intake are Associated with Adiposity and Cardiometabolic Risk Factors in Children from Mexico City. Nutrients. 2019; 11(6). doi:10.3390/nu11061207

20. Akhondzadeh S. Microbiome and Schizophrenia. Avicenna Journal of Medical Biotechnology. 2019; 11(4): 269-269.
21. Vindegaard N, Speyer H, Nordentoft M, Rasmussen S, Benros M E. Gut microbial changes of patients with psychotic and affective disorders: A systematic review. Schizophrenia Research. 2020 Jan. 14. doi:10.1016/j.schres.2019.12.014
22. Navarro F, Liu Y, Rhoads J M. Can probiotics benefit children with autism spectrum disorders? World Journal of Gastroenterology. 2016; 22(46):10093-10102. doi: 10.3748/wjg.v22.i46.10093
23. Kong X, Liu J, Cetinbas M, Sadreyev R, Koh M, Huang H, Adeseye A, He P, Zhu J, Russell H, et al. New and Preliminary Evidence on Altered Oral and Gut Microbiota in Individuals with Autism Spectrum Disorder (ASD): Implications for ASD Diagnosis and Subtyping Based on Microbial Biomarkers. Nutrients. 2019; 11(9). doi: 10.3390/nu11092128
24. Liu J, Wan G-B, Huang M-S, Agyapong G, Zou T, Zhang X-Y, Liu Y-W, Song Y-Q, Tsai Y-C, Kong X-J. Probiotic Therapy for Treating Behavioral and Gastrointestinal Symptoms in Autism Spectrum Disorder: A Systematic Review of Clinical Trials. Current Medical Science. 2019; 39(2):173-184. doi:10.1007/s11596-019-2016-4
25. Dickerson F, Adamos M, Katsafanas E, Khushalani S, Origoni A, Savage C, Schweinfurth L, Stallings C, Sweeney K, Goga J, et al. Adjunctive probiotic microorganisms to prevent rehospitalization in patients with acute mania: A randomized controlled trial. Bipolar Disorders. 2018; 20(7):614-621. doi:doi.org/10.1111/bdi.12652
26. Karkhaneh M, Fraser L, Jou H, Vohra S. Effectiveness of probiotics in infantile colic: A rapid review. Paediatrics & Child Health. 2020; 25(3):149-159. doi:10.1093/pch/pxz007
27. Jang H-M, Lee K-E, Kim D-H. The Preventive and Curative Effects of *Lactobacillus reuteri* NK33 and *Bifidobacterium adolescentis* NK98 on Immobilization Stress-Induced Anxiety/Depression and Colitis in Mice. Nutrients. 2019; 11(4). doi:10.3390/nu11040819
28. Poutahidis T, Kearney S M, Levkovich T, Qi P, Varian B J, Lakritz J R, Ibrahim Y M, Chatzigiagkos A, Alm E J, Erdman S E. Microbial symbionts accelerate wound healing via the neuropeptide hormone oxytocin. PloS One. 2013; 8(10):e78898. doi:10.1371/journal.pone.0078898
29. Poutahidis T, Kleinewietfeld M, Smillie C, Levkovich T, Perrotta A, Bhela S, Varian B J, Ibrahim Y M, Lakritz J R, Kearney S M, et al. Microbial reprogramming inhibits Western diet-associated obesity. PloS One. 2013; 8(7): e68596. doi:10.1371/journal.pone.0068596
30. Varian B J, Poutahidis T, DiBenedictis B T, Levkovich T, Ibrahim Y, Didyk E, Shikhman L, Cheung H K, Hardas A, Ricciardi C E, et al. Microbial lysate upregulates host oxytocin. Brain, Behavior, and Immunity. 2017; 61:36-49. doi:10.1016/j.bbi.2016.11.002
31. Sgritta M, Dooling S W, Buffington S A, Momin E N, Francis M B, Britton R A, Costa-Mattioli M. Mechanisms Underlying Microbial-Mediated Changes in Social Behavior in Mouse Models of Autism Spectrum Disorder. Neuron. 2019; 101(2):246-259.e6. doi:10.1016/j.neuron.2018.11.018
32. WHO Multicentre Growth Reference Study Group. WHO Child Growth Standards based on length/height, weight and age. Acta Paediatrica (Oslo, Norway: 1992). Supplement. 2006; 450:76-85. doi:10.1111/j.1651-2227.2006.tb02378.x
33. Squires J, Bricker D, Twombly E. Ages & stages questionnaires. 2009.
34. Gilliam J E. GARS-3: Gilliam Autism Rating Scale-Third Edition. 2014.
35. Bolyen E, Rideout J R, Dillon M R, Bokulich N A, Abnet C C, Al-Ghalith G A, Alexander H, Alm E J, Arumugam M, Asnicar F, et al. Reproducible, interactive, scalable and extensible microbiome data science using QIIME 2. Nature Biotechnology. 2019; 37(8):852-857. doi:10.1038/s41587-019-0209-9
36. Amir A, McDonald D, Navas-Molina J A, Kopylova E, Morton J T, Zech Xu Z, Kightley E P, Thompson L R, Hyde E R, Gonzalez A, et al. Deblur Rapidly Resolves Single-Nucleotide Community Sequence Patterns. mSystems. 2017; 2(2). doi:10.1128/mSystems.00191-16
37. Jiang L, Amir A, Morton J T, Heller R, Arias-Castro E, Knight R. Discrete False-Discovery Rate Improves Identification of Differentially Abundant Microbes. mSystems. 2017; 2(6). doi:10.1128/mSystems.00092-17
38. Douglas G M, Maffei V J, Zaneveld J, Yurgel S N, Brown J R, Taylor C M, Huttenhower C, Langille M G I. PICRUSt2: An improved and customizable approach for metagenome inference. bioRxiv. 2020 Mar. 20:672295. doi:10.1101/672295
39. Czech L, Barbera P, Stamatakis A. Genesis and Gappa: processing, analyzing and visualizing phylogenetic (placement) data. Bioinformatics (Oxford, England). 2020; 36(10):3263-3265. doi:10.1093/bioinformatics/btaa070
40. Xu Z Z, Amir A, Sanders J, Zhu Q, Morton J T, Bletz M C, Tripathi A, Huang S, McDonald D, Jiang L, et al. Calour: an Interactive, Microbe-Centric Analysis Tool. mSystems. 2019; 4(1). doi:10.1128/mSystems.00269-18
41. Varian B J, Gourishetti S, Poutahidis T, Lakritz J R, Levkovich T, Kwok C, Teliousis K, Ibrahim Y M, Mirabal S, Erdman S E. Beneficial bacteria inhibit cachexia. Oncotarget. 2016; 7(11):11803-11816. doi:10.18632/oncotarget.7730
42. Onubi O J, Poobalan A S, Dineen B, Marais D, McNeill G. Effects of probiotics on child growth: a systematic review. Journal of Health, Population, and Nutrition. 2015; 34:8. doi:10.1186/s41043-015-0010-4
43. Grembi J A, Nguyen L H, Haggerty T D, Gardner C D, Holmes S P, Parsonnet J. Gut microbiota plasticity is correlated with sustained weight loss on a low-carb or low-fat dietary intervention. Scientific Reports. 2020; 10(1):1405. doi:10.1038/s41598-020-58000-y
44. Anhê F F, Jensen B A H, Varin T V, Servant F, Van Blerk S, Richard D, Marceau S, Surette M, Biertho L, Lelouvier B, et al. Type 2 diabetes influences bacterial tissue compartmentalisation in human obesity. Nature Metabolism. 2020; 2(3):233-242. doi:10.1038/s42255-020-0178-9
45. Thingholm L B, Ruhlemann M C, Koch M, Fuqua B, Laucke G, Boehm R, Bang C, Franzosa E A, Hübenthal M, Rahnavard A, et al. Obese Individuals with and without Type 2 Diabetes Show Different Gut Microbial Functional Capacity and Composition. Cell Host & Microbe. 2019; 26(2):252-264.e10. doi:10.1016/j.chom.2019.07.004
46. Eshraghi R S, Deth R C, Mittal R, Aranke M, Kay S-IS, Moshiree B, Eshraghi A A. Early Disruption of the Microbiome Leading to Decreased Antioxidant Capacity and Epigenetic Changes: Implications for the Rise in Autism. Frontiers in Cellular Neuroscience. 2018; 12:256. doi:10.3389/fncel.2018.00256

47. Mulhall H, Huck O, Amar S. *Porphyromonas gingivalis*, a Long-Range Pathogen: Systemic Impact and Therapeutic Implications. Microorganisms. 2020; 8(6). doi: 10.3390/microorganisms8060869
48. Lloyd-Price J, Arze C, Ananthakrishnan A N, Schirmer M, Avila-Pacheco J, Poon T W, Andrews E, Ajami N J, Bonham K S, Brislawn C J, et al. Multi-omics of the gut microbial ecosystem in inflammatory bowel diseases. Nature. 2019; 569(7758):655-662. doi:10.1038/s41586-019-1237-9
49. Hiippala K, Kainulainen V, Suutarinen M, Heini T, Bowers J R, Jasso-Selles D, Lemmer D, Valentine M, Barnes R, Engelthaler D M, et al. Isolation of Anti-Inflammatory and Epithelium Reinforcing *Bacteroides* and Parabacteroides Spp. from A Healthy Fecal Donor. Nutrients. 2020; 12(4):935. doi:10.3390/nu12040935
50. Rosing J A, Walker K C, Jensen B A H, Heitmann B L. Oral *Lactobacillus* Counts Predict Weight Gain Susceptibility: A 6-Year Follow-Up Study. Obesity Facts. 2017; 10(5):473-482. doi:10.1159/000478095
51. Cox A J, West N P, Cripps A W. Obesity, inflammation, and the gut microbiota. The Lancet. Diabetes & Endocrinology. 2015; 3(3):207-215. doi:10.1016/S2213-8587(14)70134-2
52. Pedret A, Valls R M, Calderón-Pérez L, Llauradó E, Companys J, Pla-Pagà L, Moragas A, Martín-Luján F, Ortega Y, Giralt M, et al. Effects of daily consumption of the probiotic *Bifidobacterium animalis* subsp. *lactis* CECT 8145 on anthropometric adiposity biomarkers in abdominally obese subjects: a randomized controlled trial. International Journal of Obesity (2005). 2019; 43(9): 1863-1868. doi:10.1038/s41366-018-0220-0
53. Uusitupa H-M, Rasinkangas P, Lehtinen M J, Mäkelä SM, Airaksinen K, Anglenius H, Ouwehand A C, Maukonen J. *Bifidobacterium animalis* subsp. *lactis* 420 for Metabolic Health: Review of the Research. Nutrients. 2020; 12(4). doi:10.3390/nu12040892
54. Garcia-Ribera S, Amat-Bou M, Climent E, Llobet M, Chenoll E, Corripio R, Ibáñez L, Ramon-Krauel M, Lerin C. Specific Dietary Components and Gut Microbiota Composition are Associated with Obesity in Children and Adolescents with Prader-Willi Syndrome. Nutrients. 2020; 12(4). doi:10.3390/nu12041063
55. Robinson H, Barrett H, Gomez-Arango L, McIntyre H D, Callaway L, Dekker Nitert M. Ketonuria Is Associated with Changes to the Abundance of *Roseburia* in the Gut Microbiota of Overweight and Obese Women at 16 Weeks Gestation: A Cross-Sectional Observational Study. Nutrients. 2019; 11(8). doi:10.3390/nu11081836
56. Morkl S, Lackner S, Meinitzer A, Mangge H, Lehofer M, Halwachs B, Gorkiewicz G, Kashofer K, Painold A, Holl A K, et al. Gut microbiota, dietary intakes and intestinal permeability reflected by serum zonulin in women. European Journal of Nutrition. 2018; 57(8):2985-2997. doi: 10.1007/s00394-018-1784-0
57. Song Z, Wang Y, Zhang F, Yao F, Sun C. Calcium Signaling Pathways: Key Pathways in the Regulation of Obesity. International Journal of Molecular Sciences. 2019; 20(11):2768. doi:10.3390/ijms20112768
58. Tohge T, de Souza L P, Fernie A R. Current understanding of the pathways of flavonoid biosynthesis in model and crop plants. Journal of Experimental Botany. 2017; 68(15):4013-4028. doi:10.1093/jxb/erx177
59. Mounien L, Tourniaire F, Landrier J-F. Anti-Obesity Effect of Carotenoids: Direct Impact on Adipose Tissue and Adipose Tissue-Driven Indirect Effects. Nutrients. 2019; 11(7):1562. doi:10.3390/nu11071562
60. Chatuphonprasert W, Jarukamjorn K, Ellinger I. Physiology and Pathophysiology of Steroid Biosynthesis, Transport and Metabolism in the Human Placenta. Frontiers in Pharmacology. 2018 [accessed 2020 Dec. 14]; 9. frontiersin.org/articles/10.3389/fphar.2018.01027/full. doi:10.3389/fphar.2018.01027
61. Reily C, Stewart T J, Renfrow M B, Novak J. Glycosylation in health and disease. Nature Reviews. Nephrology. 2019; 15(6):346-366. doi:10.1038/s41581-019-0129-4
62. Ma Q, Zhou X, Hu L, Chen J, Zhu J, Shan A. Leucine and isoleucine have similar effects on reducing lipid accumulation, improving insulin sensitivity and increasing the browning of WAT in high-fat diet-induced obese mice. Food & Function. 2020; 11(3):2279-2290. doi: 10.1039/c9fo03084k
63. Bevan P. Insulin signalling. Journal of Cell Science. 2001; 114(8):1429-1430.
64. Rose D R, Yang H, Serena G, Sturgeon C, Ma B, Careaga M, Hughes H K, Angkustsiri K, Rose M, Hertz-Picciotto I, et al. Differential immune responses and microbiota profiles in children with autism spectrum disorders and co-morbid gastrointestinal symptoms. Brain, Behavior, and Immunity. 2018; 70:354-368. doi: 10.1016/j.bbi.2018.03.025
65. Oliphant K, Allen-Vercoe E. Macronutrient metabolism by the human gut microbiome: major fermentation by-products and their impact on host health. Microbiome. 2019; 7(1):91. doi:10.1186/s40168-019-0704-8
66. Hanna V S, Hafez E A A. Synopsis of arachidonic acid metabolism: A review. Journal of Advanced Research. 2018; 11:23-32. doi:10.1016/j.jare.2018.03.005
67. Kuehl F A, Egan R W. Prostaglandins, arachidonic acid, and inflammation. Science (New York, N.Y.). 1980; 210(4473):978-984. doi:10.1126/science.6254151
68. Hersoug L-G, Møller P, Loft S. Role of microbiota-derived lipopolysaccharide in adipose tissue inflammation, adipocyte size and pyroptosis during obesity. Nutrition Research Reviews. 2018; 31(2):153-163. doi: 10.1017/S0954422417000269
69. Srikantha P, Mohajeri M H. The Possible Role of the Microbiota-Gut-Brain-Axis in Autism Spectrum Disorder. International Journal of Molecular Sciences. 2019; 20(9). doi:10.3390/ijms20092115
70. Postma P W, Lengeler J W, Jacobson G R. Phosphoenolpyruvate:carbohydrate phosphotransferase systems of bacteria. Microbiological Reviews. 1993; 57(3):543-594.
71. Meadow N D, Fox D K, Roseman S. The bacterial phosphoenolpyruvate: glycose phosphotransferase system. Annual Review of Biochemistry. 1990; 59:497-542. doi:10.1146/annurev.bi.59.070190.002433
72. Salehi P, Herzig L, Capone G, Lu A, Oron A P, Kim S-J. Comparison of Aberrant Behavior Checklist profiles across Prader-Willi syndrome, Down syndrome, and autism spectrum disorder. American Journal of Medical Genetics. Part A. 2018; 176(12):2751-2759. doi:10.1002/ajmg.a.40665
73. Bennett J A, Germani T, Haqq A M, Zwaigenbaum L. Autism spectrum disorder in Prader-Willi syndrome: A systematic review. American Journal of Medical Genetics. Part A. 2015; 167A(12):2936-2944. doi:10.1002/ajmg.a.37286

74. Strati F, Cavalieri D, Albanese D, De Felice C, Donati C, Hayek J, Jousson O, Leoncini S, Renzi D, Calabrò A, et al. New evidences on the altered gut microbiota in autism spectrum disorders. Microbiome. 2017 [accessed 2020 Dec. 16]; 5. ncbi.nlm.nih.gov/pmc/articles/PMC5320696/. doi:10.1186/s40168-017-0242-1
75. Elmassry M M, Chung E, Cao J J, Hamood A N, Shen C-L. Osteoprotective effect of green tea polyphenols and annatto-extracted tocotrienol in obese mice is associated with enhanced microbiome vitamin K2 biosynthetic pathways. The Journal of Nutritional Biochemistry. 2020; 86:108492. doi:10.1016/j.jnutbio.2020.108492
76. Crovesy L, Masterson D, Rosado E L. Profile of the gut microbiota of adults with obesity: a systematic review. European Journal of Clinical Nutrition. 2020; 74(9):1251-1262. doi:10.1038/s41430-020-0607-6

Example 2: Supplementation with *B. lactis*

Study Design

Figure 13:
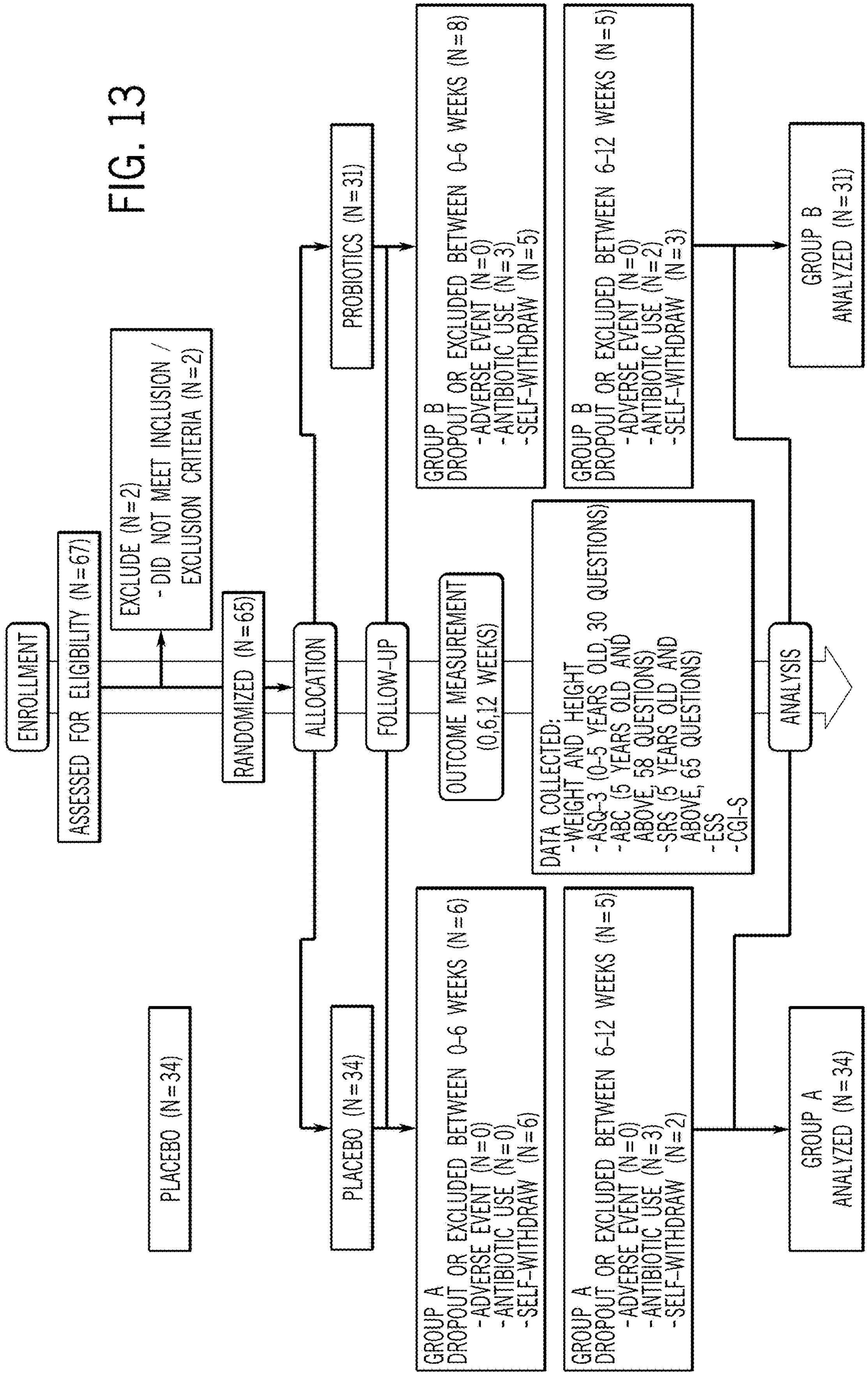
FIG. 13. Flowchart summary of study conduct and participant enrollment and dropout for the study on *B. lactis*.

We designed and conducted a randomized, double-blinded, placebo-controlled clinical trial (flowchart, FIG. 13). In this trial, we randomly assigned the eligible PWS participants, with a 1:1 ratio, to either the probiotics or placebo group. We hypothesize that a 12-week treatment period is sufficient for probiotics supplementation to induce detectable changes. To achieve a statistical power of 80% for primary outcomes with a large effect size of 0.8 (Cohen's d) assumed, a total of 52 participants (26 in each arm) were required.

Ethical Considerations

Ethical Approval was issued by the Internal Review Board (IRB) of the Second Affiliated Hospital of Kunming Medical University (Review-YJ-2016-06). Clinical Trial of Probiotics was registered at the Chinese Clinical Trial Registry (ChiCTR), with a number ChiCTR1900022646. Signed informed consent was obtained from the parents or legal guardians of the subjects according to the IRB requirements. The study was conducted in accordance with the Declaration of Helsinki.

Participants

We enrolled 65 subjects aged 52.5±38.2 months (69.1% male, 30.9% female) with genetically confirmed diagnosis of Prader-Willi syndrome. Study participants were recruited through the PWS Care & Support Center, located in Zhejiang, China. Participants were included if they met the following criteria: they had been genetically confirmed to have PWS; had not been on any forms of probiotics for at least four weeks; had stable medications for at least four weeks; had no planned changes in medications or psychosocial interventions during the trial; had a willingness to provide stool samples in a timely manner; and had a willingness to collaborate with interviews and study procedures. Potential participants were excluded if they had other known genetic disorders, or if they were pregnant or breast-feeding before the study.

Randomization and Blinding

Randomization and allocation concealment were performed by a statistician who was not part of the research team. Randomization sampling numbers were electronically generated for each de-identified subject. Coded probiotics and placebo of identical appearance were prepared by the Beijing Huayuan Academy of Biotechnology to ensure allocation concealment. Both the participants and the research staff/investigators who collected and analyzed the outcome data were blinded to treatment status. Blinding was also maintained by making the probiotics package appear identical to the placebo sachet.

Intervention

Probiotics BL-11 (Beijing Huayuan Academy of Biotechnology) was used in the study in the format of a sachet containing the probiotic BL-11 in powder form. Each sachet of probiotics supplement contained $3\times10^{10}$ colony forming units (CFUs). The placebo was maltodextrin in the sachet with similar color, flavor, and taste as the probiotic sachets. Subjects received one sachet twice a day of either probiotics or a placebo for a duration of 12 weeks and were instructed to consume the sachet contents orally with water.

Primary Outcomes:

1. Weight and height measurements were obtained by parents using standard scales and collected by the research staff. Weight, height, and BMI were converted to z-score using age growth references provided by WHO (WHO Multicentre Growth Reference Study Group, 2006).
2. Psychological measurements 1) Ages and Stages Questionnaires, 3rd Edition (ASQ-3) (Parent-Completed, n.d.). ASQ-3 is one of the most widely available development screening tools for young children. The ASQ-3 has five domains: communication, gross motor, fine motor, problem-solving, and personal-social. Total scores were calculated. We interviewed all subjects younger than five years old.

2) Aberrant Behavior Checklist (ABC) (Bolyen et al., 2019). ABC is a 58-item behavior rating scale used to measure behavior problems across five subscales: irritability, lethargy/social withdrawal, stereotypic behavior, hyperactivity/noncompliance, and inappropriate speech. Total scores were calculated. We interviewed all subjects older than five years old.

3) Social Responsiveness Scale (SRS)(Constantino & Gruber, 2005). SRS consists of 65 items used for quantitative assessment of the severity of social behaviors. Total scores were calculated. We interviewed all subjects older than five years old.

4) Restricted and repetitive behaviors (RRB) is based on a 4-point scale (0-3) adopted from the Gilliam Autism Rating Scale, Third Edition (GARS-3) (Gilliam, 2014). Total scores were calculated. We interviewed all subjects older than three years old.

Secondary Outcomes:

1. Fecal Microbiome

1) Sample Handling and Collection

Stool samples were collected at three study timepoints: prior to intervention (0-weeks), 6-weeks, and 12-weeks. Sample collection was performed with DNA/RNA shield fecal collection tubes (Zymo, Cat #R1101) containing 1 mL preservation solution and were transported to the laboratory by ice bags and then frozen at −80° C. TIANmap stool DNA kit was used to extract DNA (TIANGEN, Cat #DP328) according to the manufacturer's instructions, and DNA samples were carefully quantified with a Nanodrop Spectrophotometer. A260/A280 ratios were also measured to confirm high-purity DNA yield. DNA samples were frozen at −20° C. until use.

2) 16S rRNA Gene Amplicon Sequencing

The 16S rRNA V3-V4 library was constructed by two rounds of PCR with the following primers: 341F: 5'TCGTCGGCAGCGTCAGATGTGTATAAGA-GACAGCCTACGGGAGGCAGCAGC CTACGGG-NBGCASCAG3' (SEQ ID NO: 1) and 805R: 5'GTCTCGTGGGCTCGGAGATGTGTATAAGAG ACAGTGACTACNVGGGTATCTA ATCC3' (SEQ ID NO:

2) via reaction procedure (95° C. for 2 min, followed by 25 cycles at 95° C. for 30 s, 55° C. for 30 s, and 72° C. for 30 s, and a final extension at 72° C. for 5 min). PCR products were purified with 1×KAPA AMPure beads (KAPA, Cat #KK8002). Then, products were put through a second PCR reaction procedure (95° C. for 2 min, followed by eight cycles at 95° C. for 30 s, 55° C. for 30 s, and 72° C. for 30 s, and a final extension at 72° C. for 5 min). PCR products were purified with 1×KAPA AMPure beads and analyzed using a Bioanalyzer DNA kit, followed by quantification with real-time PCR. DNA libraries were pooled and sequenced on Illumina MiSeq (Illumina; CA) using a 2×250 bp paired-end protocol with overlapping reads.

2. Clinical Global Impression (CGI) was developed for use in clinical trials to provide a brief, stand-alone assessment of the clinician's view of the patient's global functioning prior to and after initiating a study medication. The CGI comprises two companion one-item measures evaluating the following: (a) severity of psychopathology from 1 to 7 (CGI-S) and (b) change from the initiation of treatment on a similar seven-point scale (CGI-I)31.
3. GI symptoms were assessed based on the total number of existing GI symptoms at baseline, including constipation, diarrhea, abdominal pain, excessive flatulence, bloody stool, nausea, difficulty swallowing, poor appetite, indigestion, and acid reflux.

Statistical Analysis

All raw data were recorded and processed in Microsoft Excel 2007 and R. The presentation of data follows the CONSORT recommendations for reporting results of Randomized Clinical Trials (RCTs). Statistical procedures were carried out using $\alpha=0.05$ as the significance level.

We applied the Wilcoxon rank-sum test to explore the intergroup differences in the z-scores of weight, height, total scores and sub-scores of ASQ-3, ABC, and SRS at baseline, per-subject changes from 0 to 6 weeks, and per-subject changes from 6 to 12 weeks. Linear mixed models were also used to account for repeated measures.

Due to having several primary outcomes, false discovery rate (FDR) was used to adjust for multiple comparisons. Secondary outcomes were analyzed using similar methods as that of primary outcomes. In addition, linear regression was performed to check for correlations between clinical indices and microbiome compositions.

Microbiome Data Processing and Analysis

The sequencing reads were filtered using the QIIME2 (v2019.10) based on quality scores (Bolyen et al., 2019). Deblur was used to denoise with default parameters and obtain an abundance table of samples by amplicon sequence variants (ASVs)(Amir et al., 2017).

Alpha diversities were calculated with QIIME2. Bray-Curtis distance was used to characterize microbiome beta diversity. Taxonomies for ASVs were assigned using the sklearn-based taxonomy classifier trained on the sequences at 99% similarity level from Greengenes v13.8. Significant differences in the relative abundance of microbial phyla, genera, and alpha diversity between placebo and probiotics groups were identified by Kruskal-Wallis tests. A false discovery rate (FDR) based on the Benjamini-Hochberg (BH) adjustment was applied for multiple comparisons (Jiang et al., 2017).

PICSRUSt2 was used to infer microbial functional content based on ASVs' abundant tables and then produced the Kyoto Encyclopedia of Genes and Genomes (KEGG) orthologs (KO), Enzyme Classification numbers, and pathway abundance table(Czech et al., 2020; Douglas et al., 2020). The differential analyses were performed on the fold ratios between probiotics and placebo groups with a permutation-based nonparametric test, and the top differential features were rendered and plotted with Calour(Xu et al., 2019). All raw data from 16s rRNA Illumina amplicon sequencing have been deposited in The National Center for Biotechnology Information (NCBI) Sequence Read Archive (SRA, PRJNA643297).

Results

1. Demographic Features of PWS Participants

Figure 14:
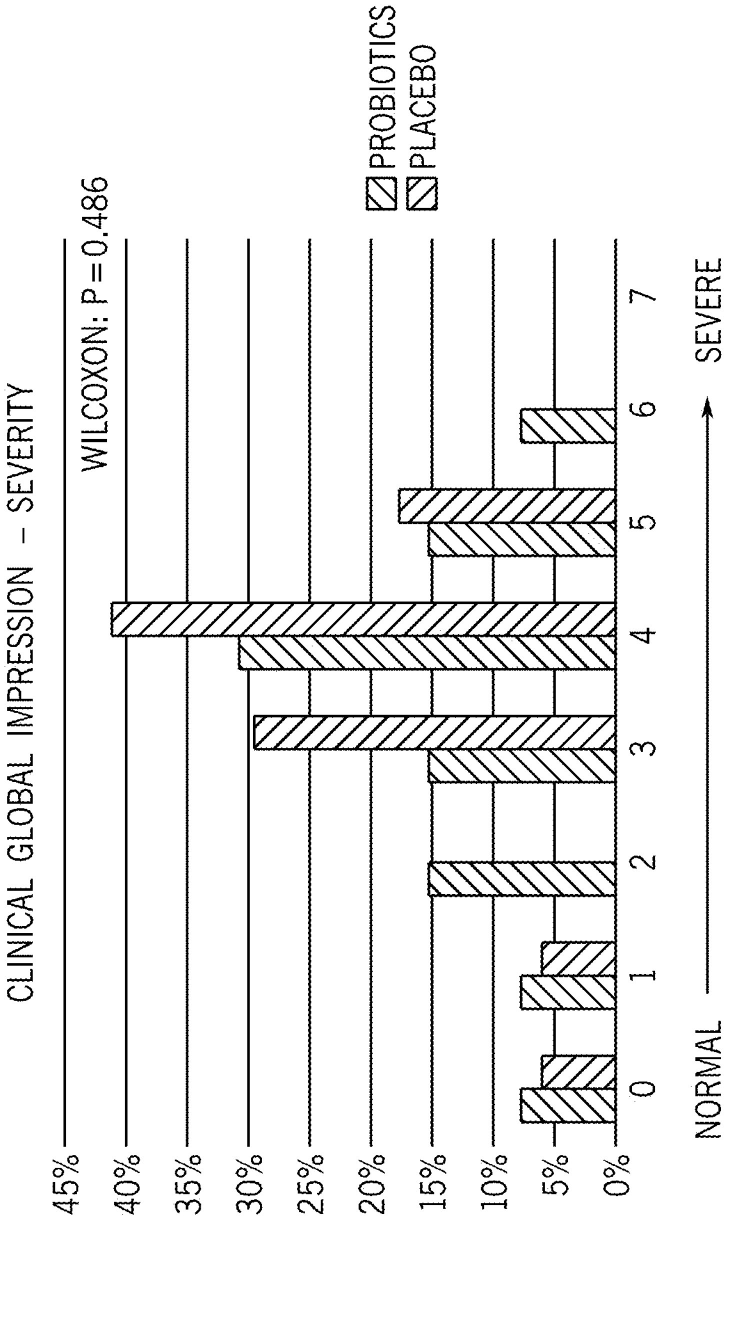
FIG. 14. Clinical Global Impression (CGI)—Severity at Baseline between two groups for the study on *B. lactis*. Comparison of CGI-S at baseline between probiotics group (blue) and placebo group (yellow). There is no difference in overall severity level found between groups (p>0.05).

A total of 65 subjects with genetically confirmed diagnosis of Prader-Willi syndrome were enrolled. Of which, 31 subjects aged 49.4±34.4 months were randomized to receive active probiotic, BB-11, while 34 subjects aged 55.5±41.9 months were randomized to receive placebo. Groupwise comparisons of baseline age and gender distributions did not indicate any significant differences (P>0.05). Detailed demographic characteristics and co-morbid GI symptoms of the enrolled participants are summarized in Table 1. The overall severity presented by CGI-S scores at baseline compared between groups is presented in FIG. 14. No group differences were observed (P>0.05). 47.5% of subjects display one or more GI symptoms within the study population, as shown in Table 2, below.

TABLE 2

Demographic features and co-morbid GI symptoms of participants.

| | | Probiotic Group | Placebo Group | P-value* |
|---|---|---|---|---|
| Age (months, N (mean ± SD)) | All subjects | 31 (49.4 ± 34.3) | 34 (55.5 ± 41.9) | 0.26 |
| | >5 years | 11 (90.3 ± 26.1) | 11 (106.6 ± 32.9) | 0.27 |
| | ≤5 years | 22 (28.9 ± 12.3) | 24 (31.1 ± 14.5) | 0.12 |
| Sex (N (%)) | Male | 22 (67%) | 25 (71%) | 0.73 |
| | Female | 11 (33%) | 10 (29%) | |
| Genotype (N (%)) | Deletion | 11 (33%) | 9 (26%) | 0.71 |
| | Disomy | 20 (61%) | 21 (60%) | |
| | Other/Unknown | 2 (6%) | 4 (11%) | |
| Weight (kg, mean ± SD) | | 19.6 ± 13.7 | 23.7 ± 16.9 | 0.16 |
| Height (cm, mean ± SD) | | 98.1 ± 18.8 | 104 ± 22.9 | 0.18 |
| BMI (mean ± SD) | | 18.4 ± 6.28 | 19.4 ± 6.01 | 0.22 |
| GI Symptoms (has ≥1) | | 0.87 ± 1.63 | 1.39 ± 1.75 | 0.24 |

*Chi-square test was performed on sex and genotype, for which the p-values were >0.05 across the groups. T-test was performed on age, weight, height, BMI, and GI symptoms for which P-values were non-significant at $\alpha = 0.05$ across the groups.

No serious or severe adverse events were observed. All the observed adverse events and major causes of drop out are listed as a table in FIG. 15. There was no significant difference found between the two groups (P>0.05).

Figure 16A:
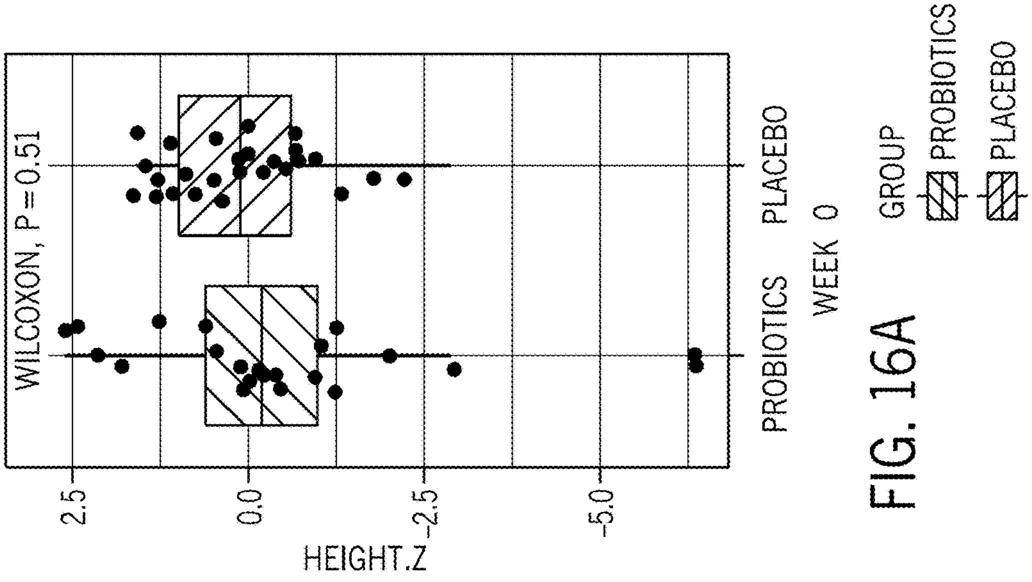
FIG. 16A-16F. Comparison of the height (A-C) and weight (D-F) z-score changes at baseline, from week 0 to 6, and from week 6 to 12 between probiotic groups (blue) and placebo (yellow) using Wilcoxon rank-sum test for the study on *B. lactis*.
Figure 16B:
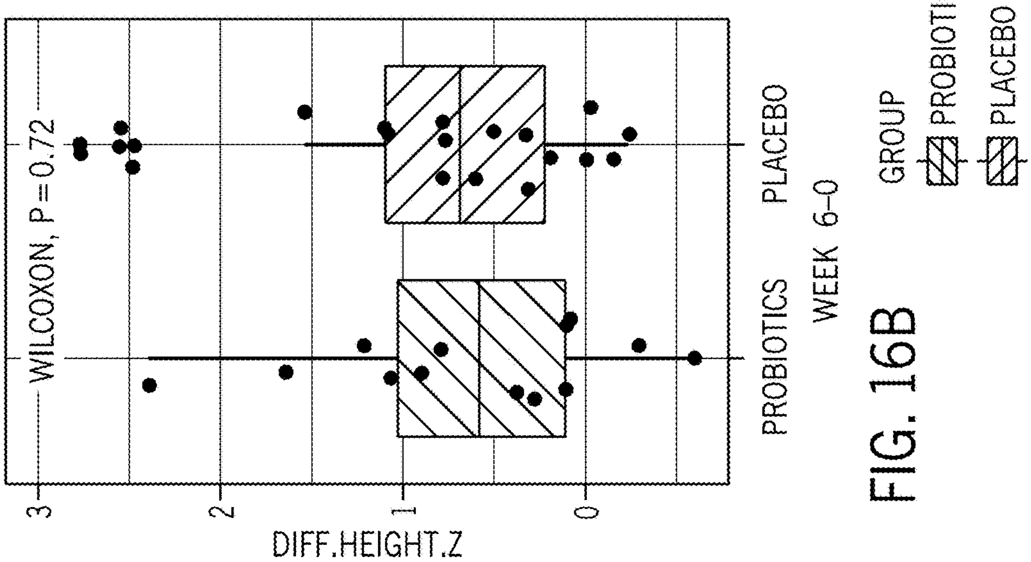
Figure 16C:
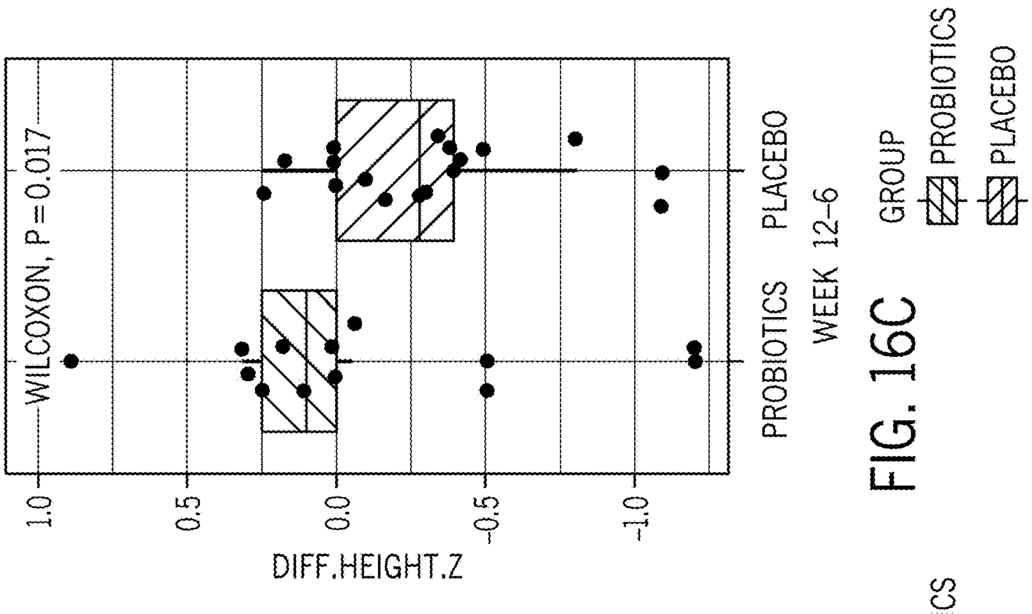
Figure 16D:
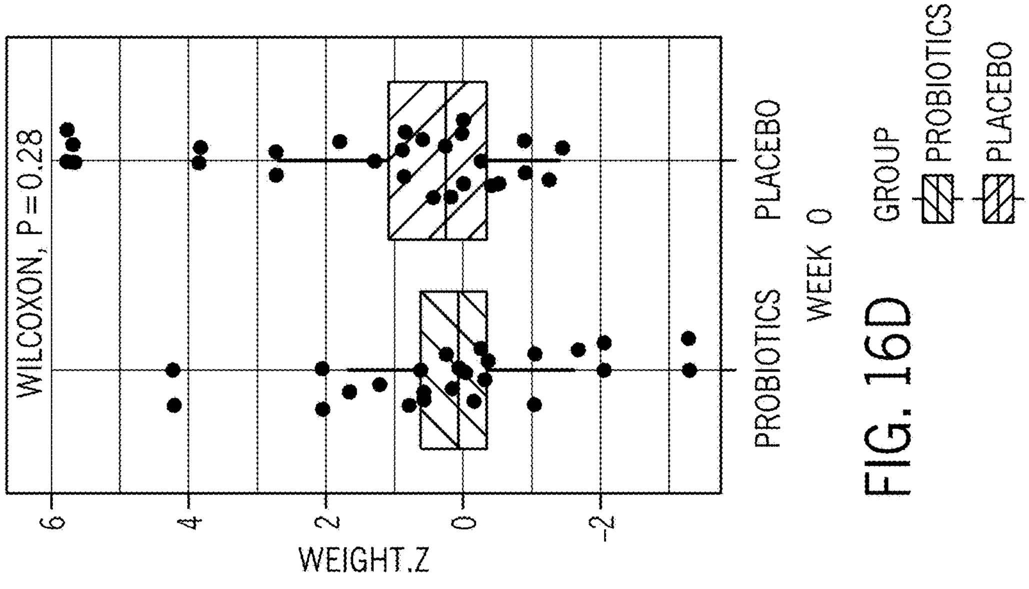
Figure 16E:
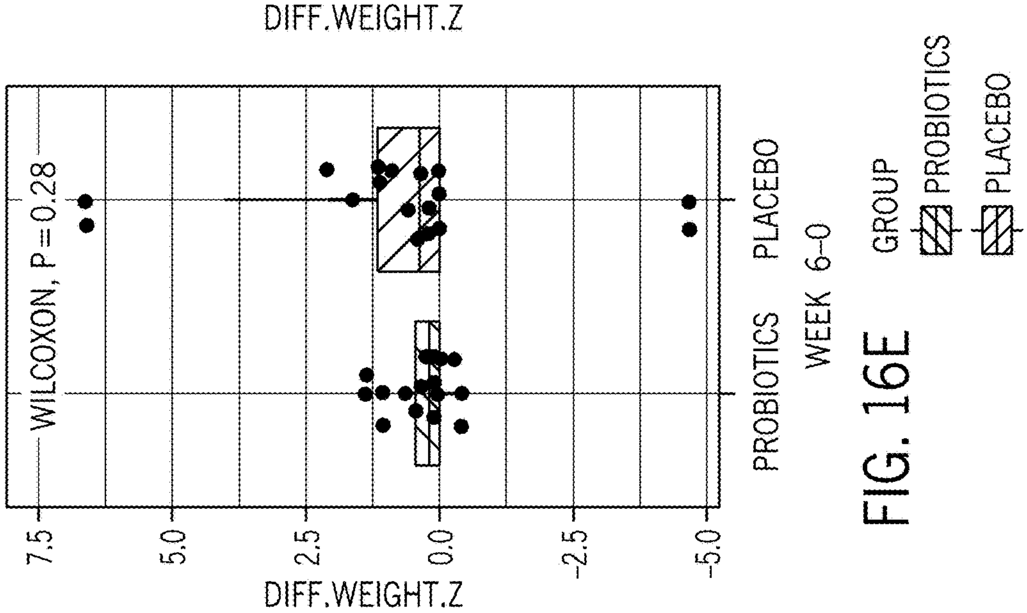
Figure 16F:
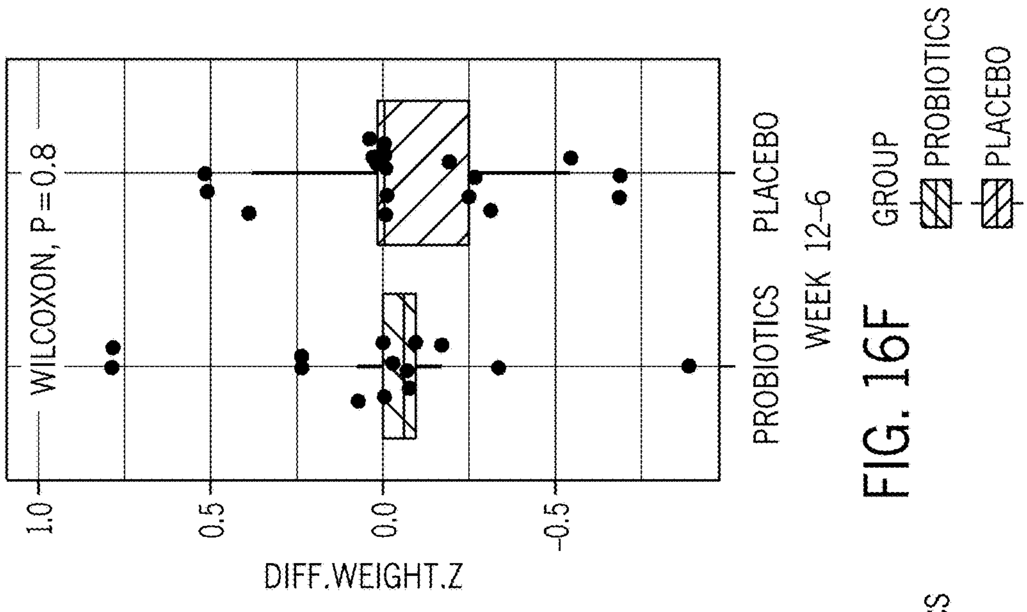
Figure 17B:
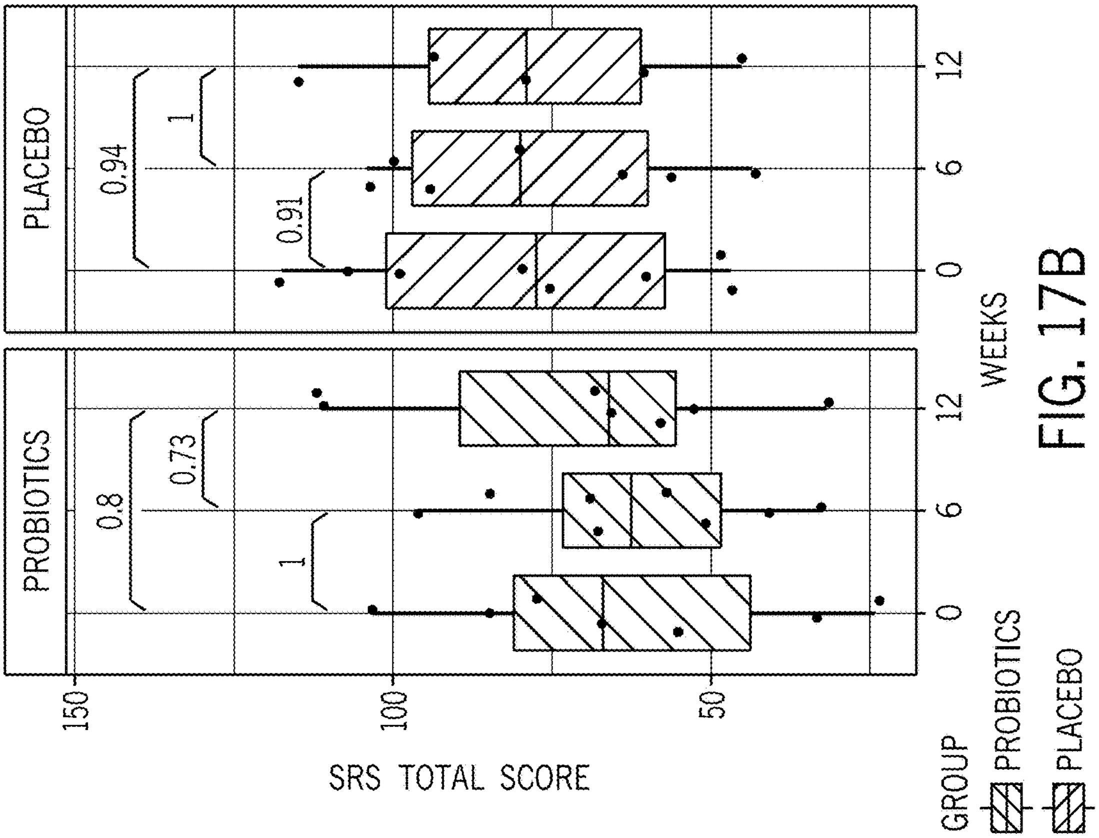
FIG. 17A-17D. Comparison of the ABC total score (A), SRS-2 total score (B), ASQ-3 total score (C) and RRB score (D) over the intervention course between probiotics group (blue) and placebo group (brown) for the study on *B. lactis*. There was no group significance found (P>0.05).
Figure 17A:
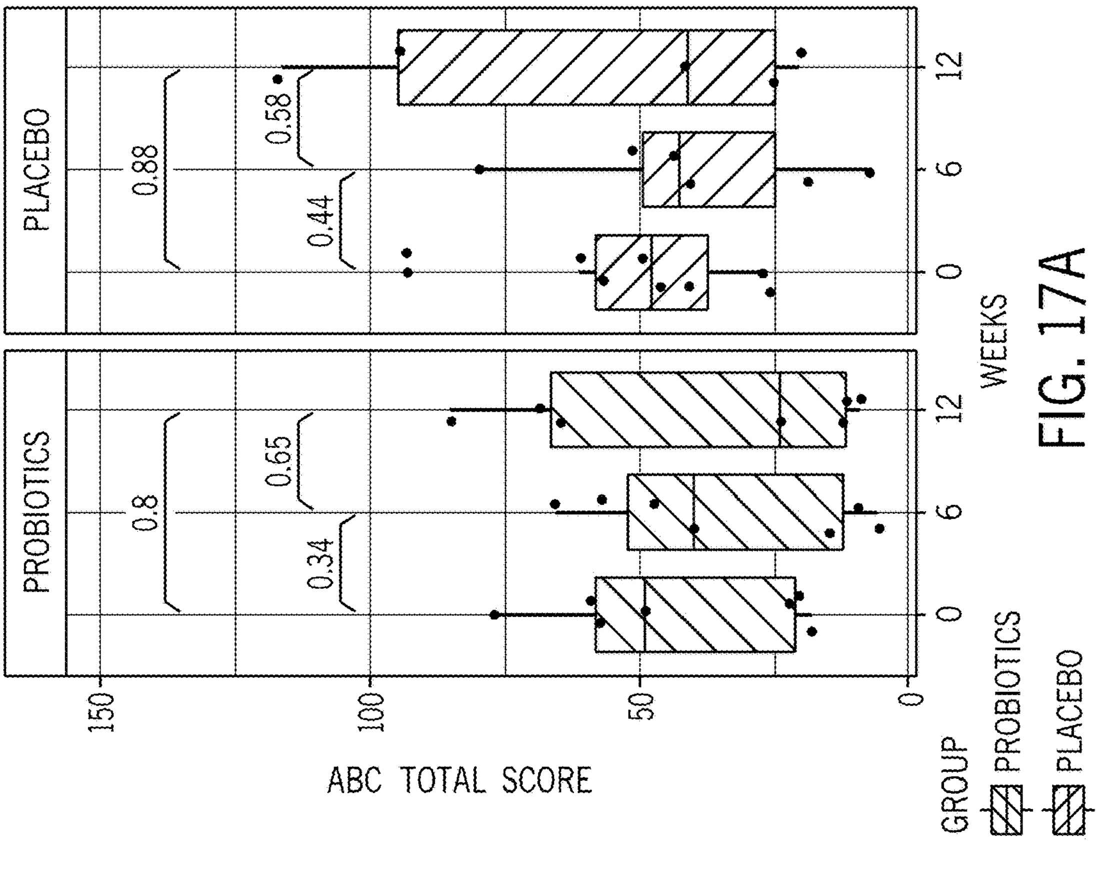
Figure 17D:
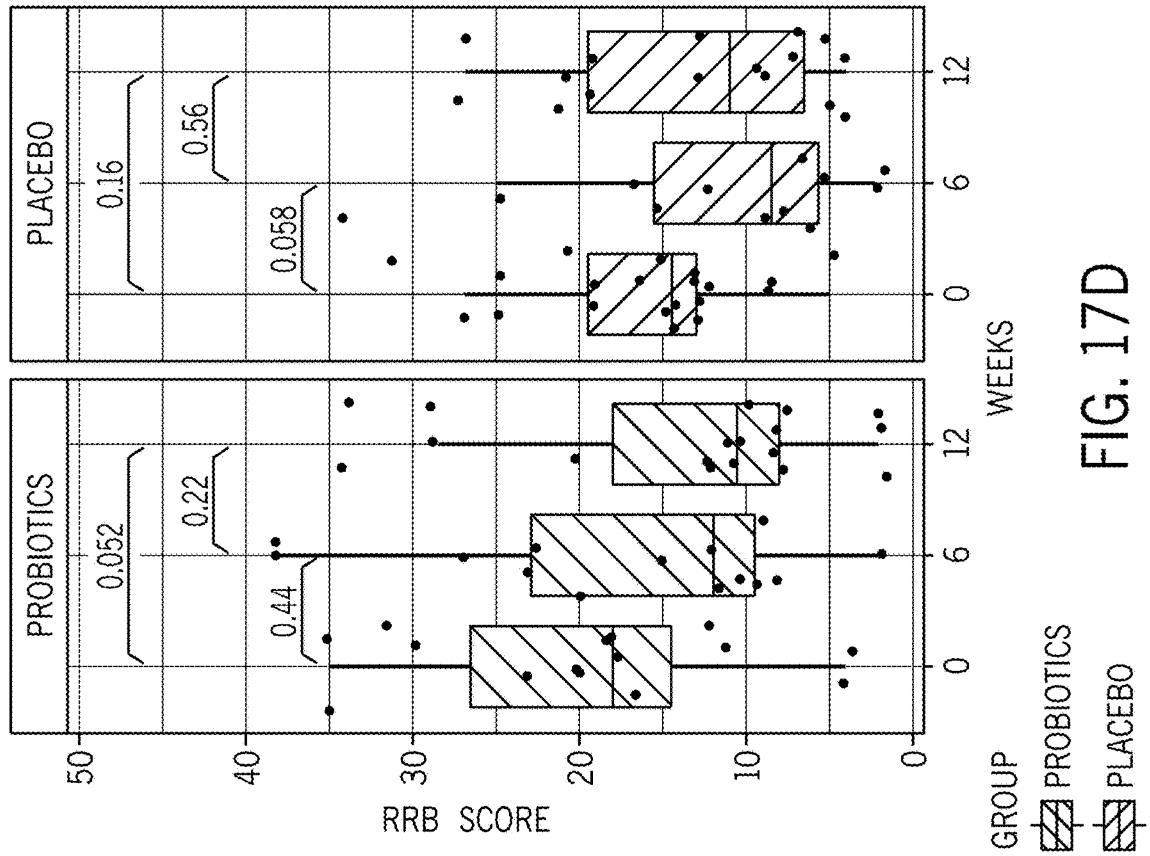
Figure 17C:
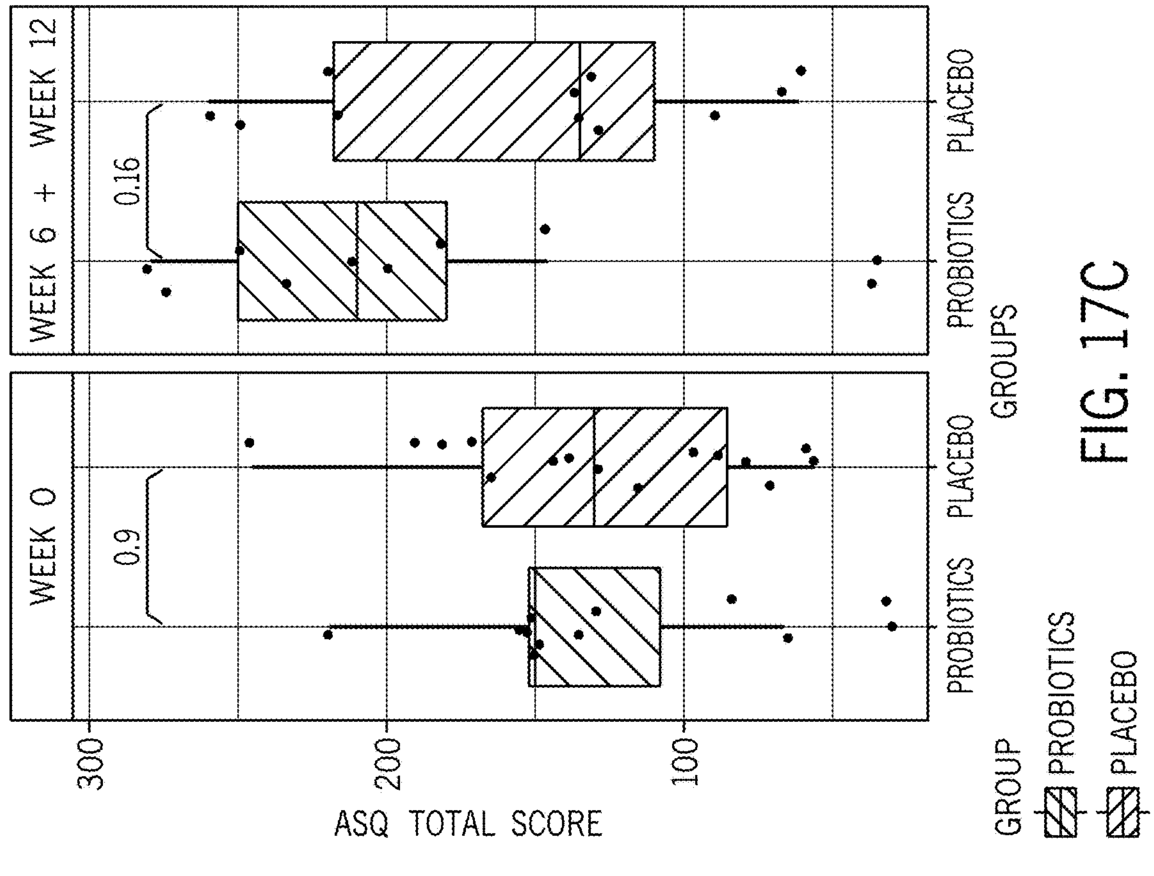

2. Effects of Probiotics on Weight, Height, Psychological Measurements, and CGI-I Anthropometric measures were collected and analyzed throughout the treatment course. The height increase from 6 to 12 weeks was significantly greater in the probiotics group than the placebo group (mean difference=2.58 cm, P<0.05, FIG. 16A-C). No significant changes in weight over time were observed in either group (FIG. 16D-F).

Results obtained from psychological measurements, including the ASQ-3, ABC, SRS, and RRB, are shown in FIG. 17. No significant difference was found with the linear mixed effect model (P>0.05) for ASQ-3, ABC, SRS, and RRB scores.

Figure 18:
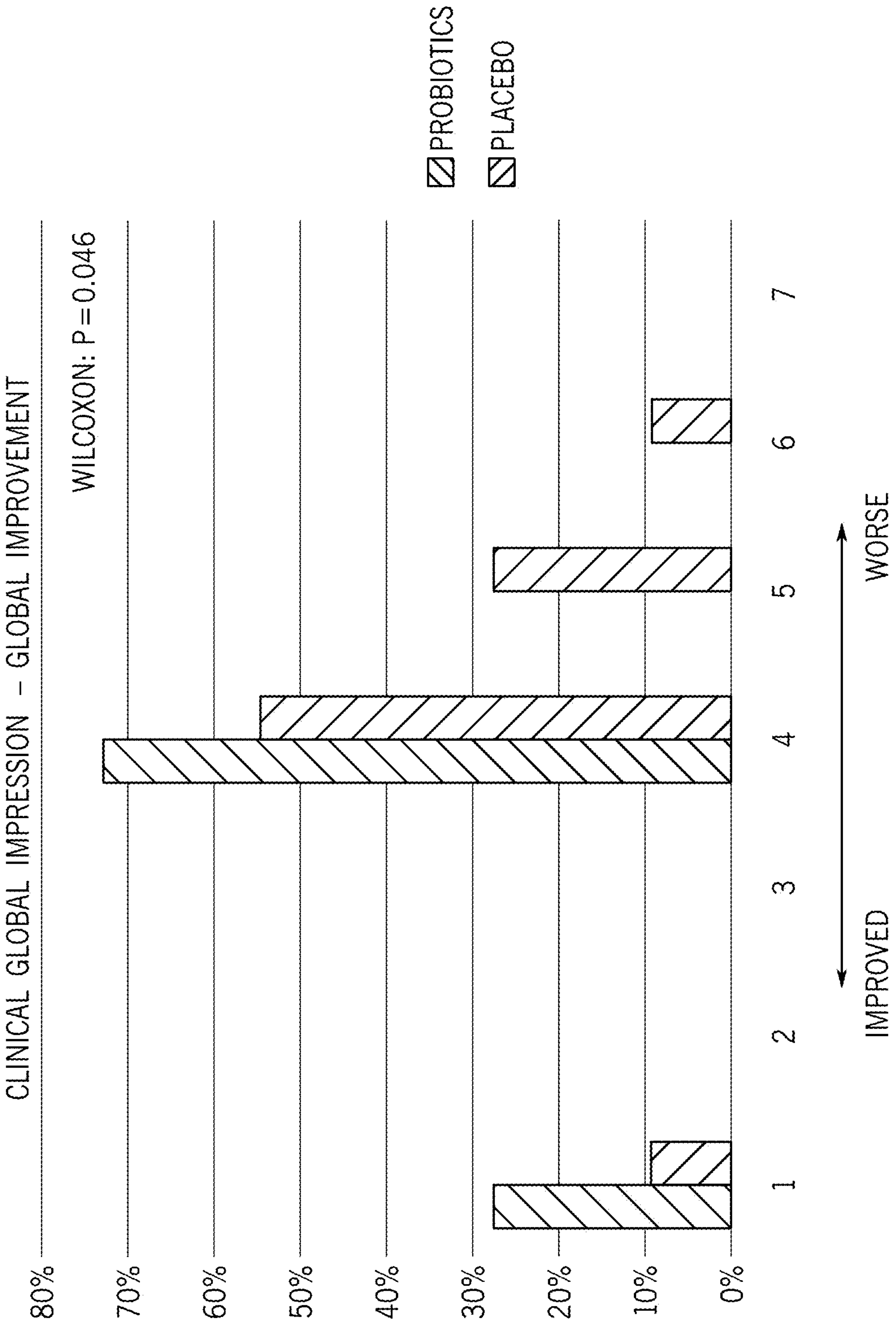
FIG. 18. CGI-I of probiotics and placebo at 12 weeks for the study on *B. lactis*. Percentage of participants given each improvement level was displayed as bar plot, probiotics group (blue) had overall significantly better improvement than the placebo group (yellow, p<0.05).

The overall improvement of symptoms during the treatment course was measured using the CGI-I scale. We observed significantly greater symptom improvement in the probiotics group compared to the placebo group (FIG. 18, P<0.05).

3. Changes in Microbiome Composition and Function with Probiotics Intervention

Figure 19A:
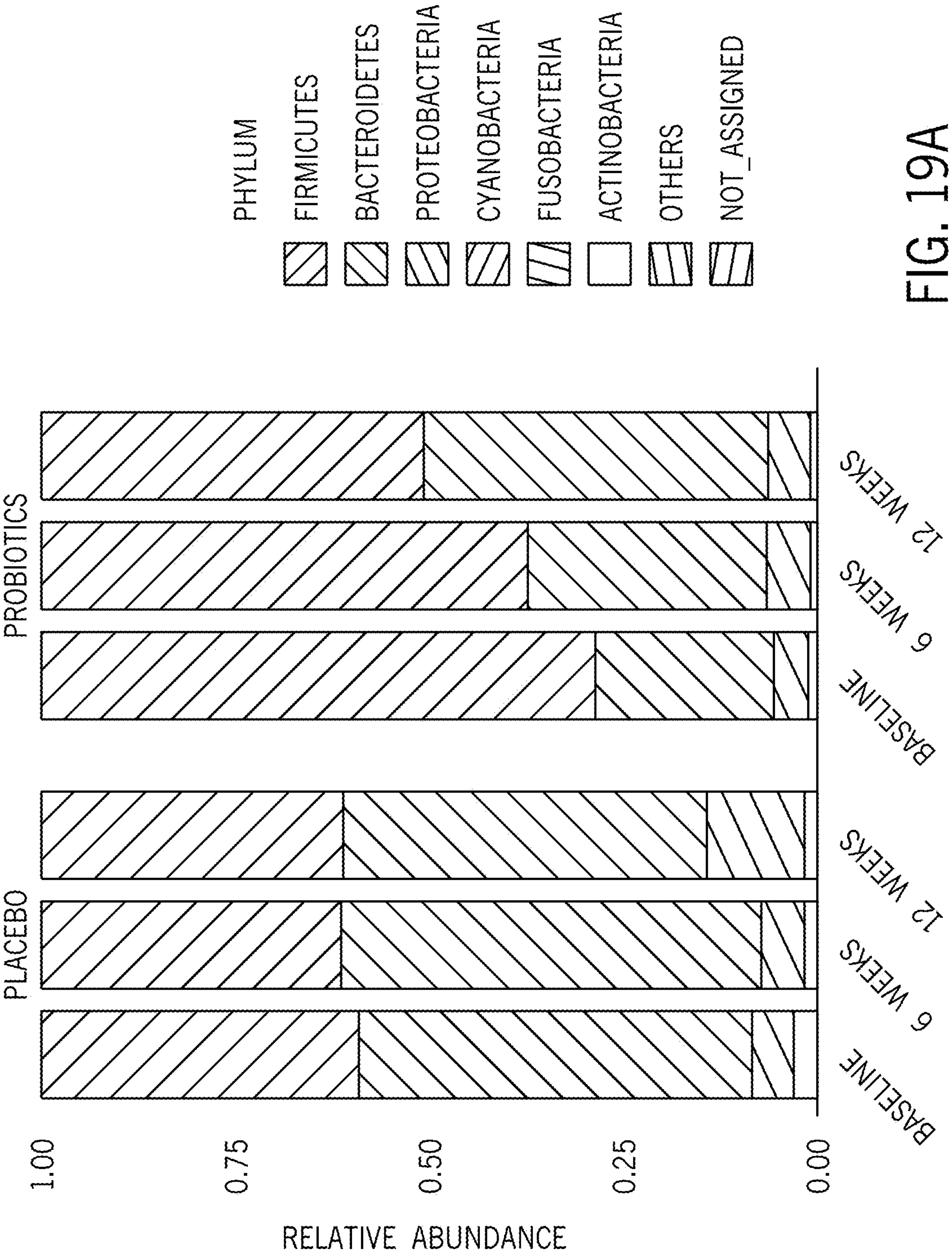
FIG. 19A-19C. Summary of phylum and genus level gut microbiota relative abundances in both probiotics and placebo group subjects at baseline, 6 weeks, and 12 weeks for the study on *B. lactis*.
Figure 19B:
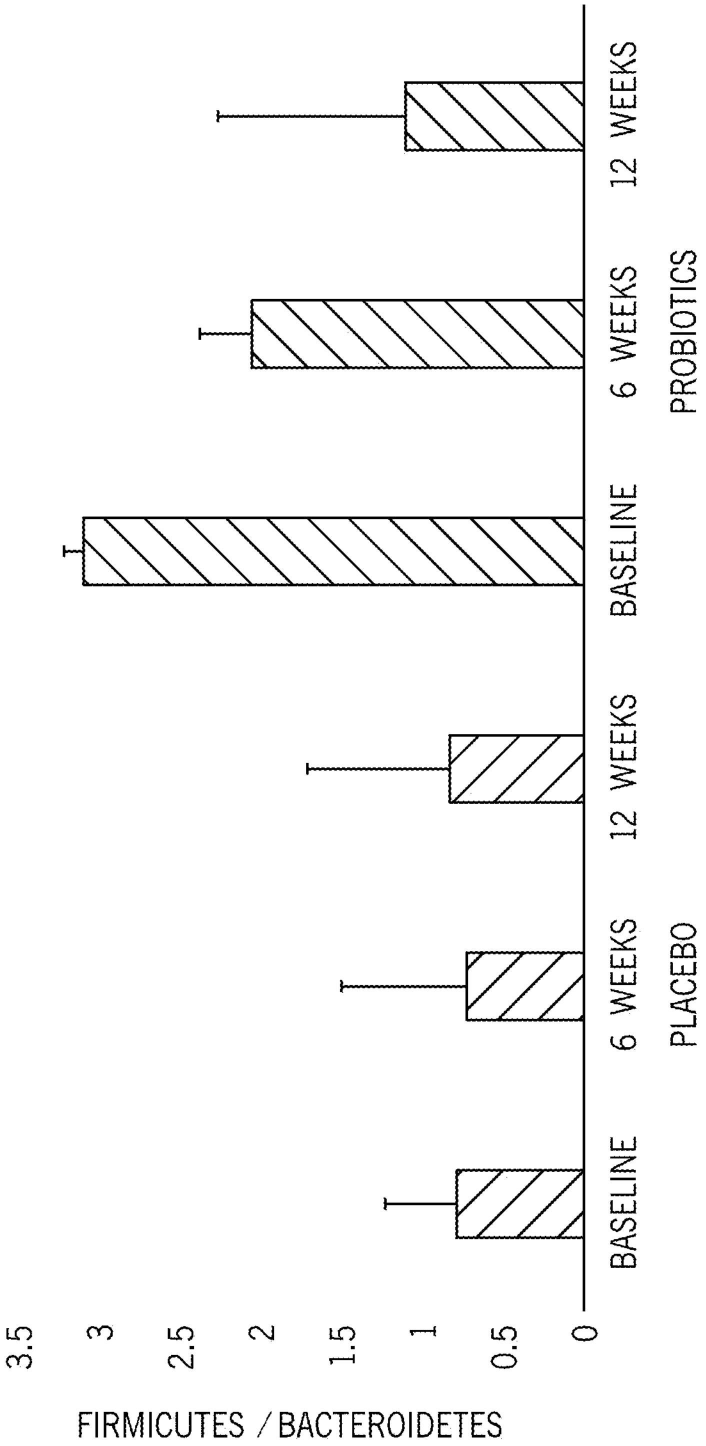
Figure 19C:
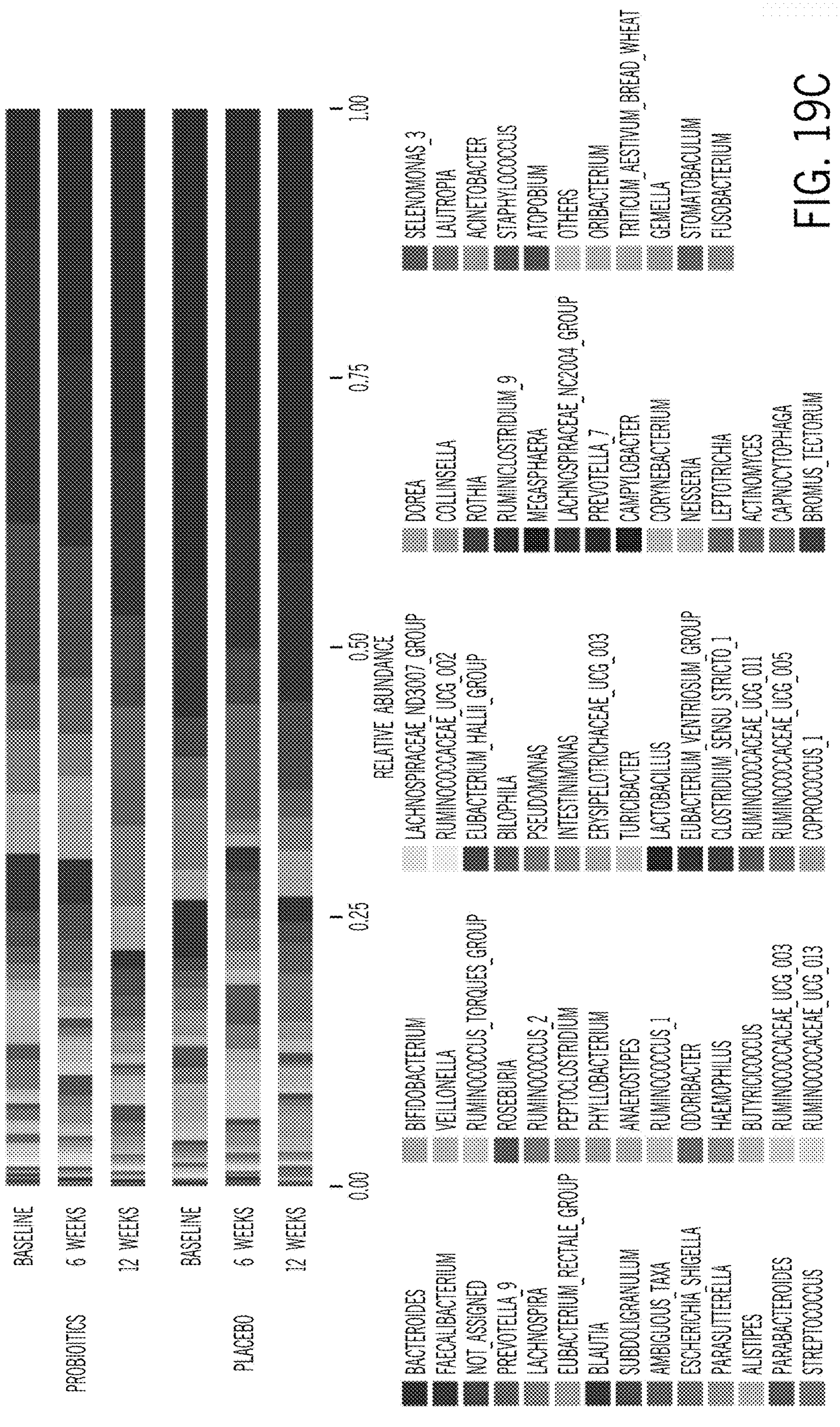
Figure 20A:
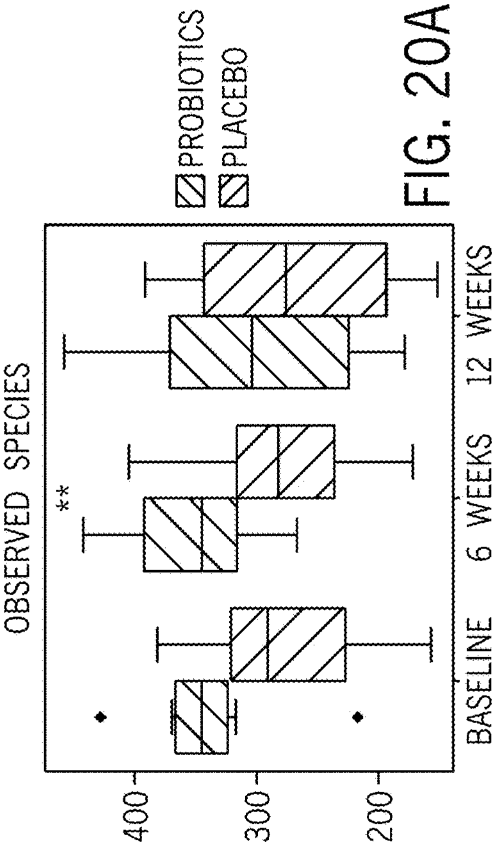
FIG. 20A-20E. α and β diversity index changes from probiotics intervention for the study on *B. lactis*. (A) observed species index; (B) faith's phylogenetic diversity; (C) Shannon index; (D) Simpson index. * P<0.05; ** P<0.01, via t-test. (E) R diversity with Nonmetric multidimensional scaling (NMDS) score plots of gut microbial data based on a Bray-Curtis dissimilarity matrix. Placebo (red dots) and probiotics (blue dots).
Figure 20B:
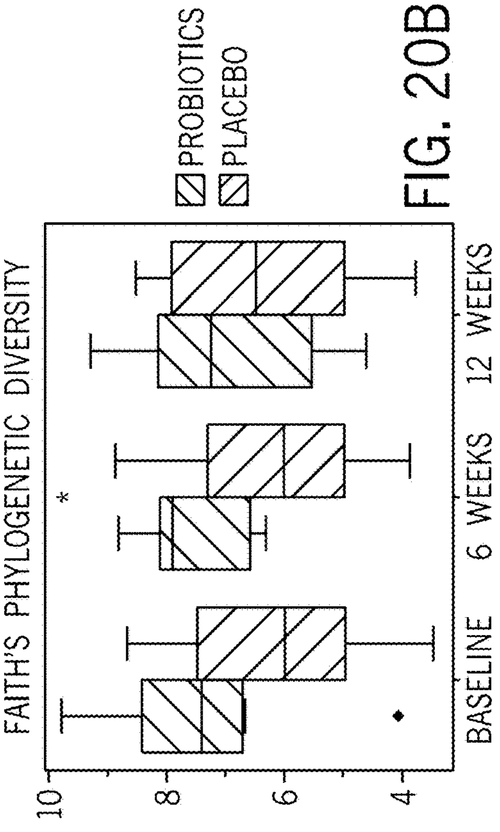
Figure 20C:
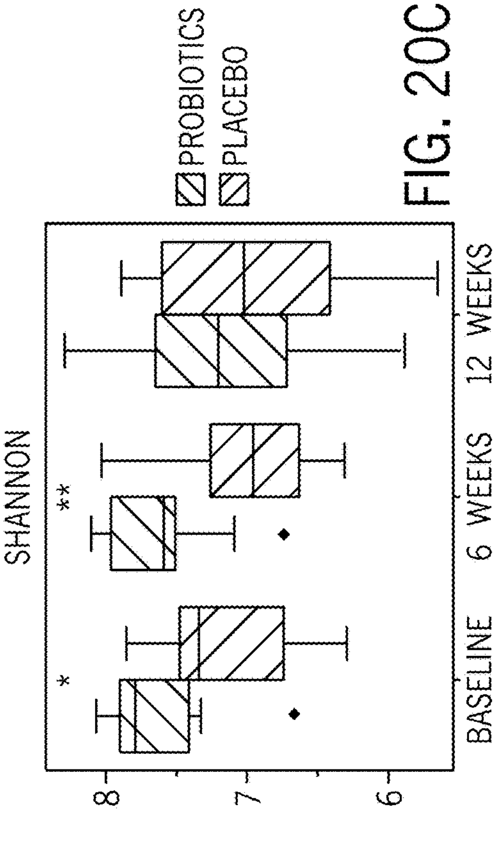
Figure 20D:
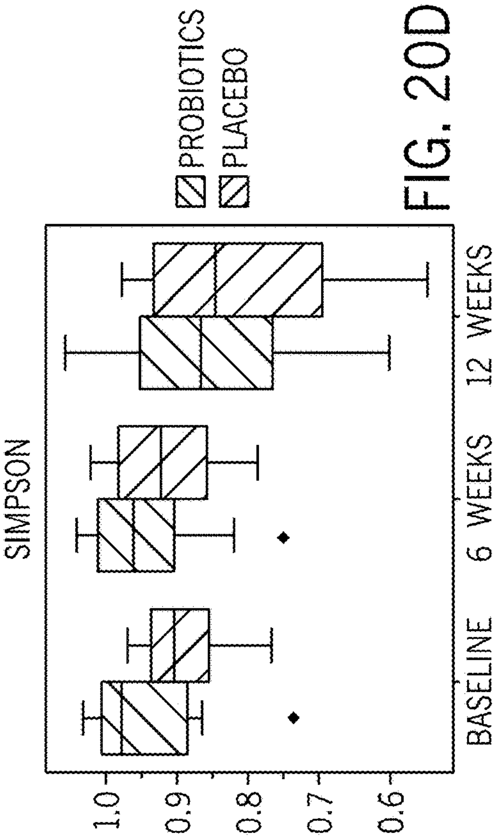
Figure 20E:
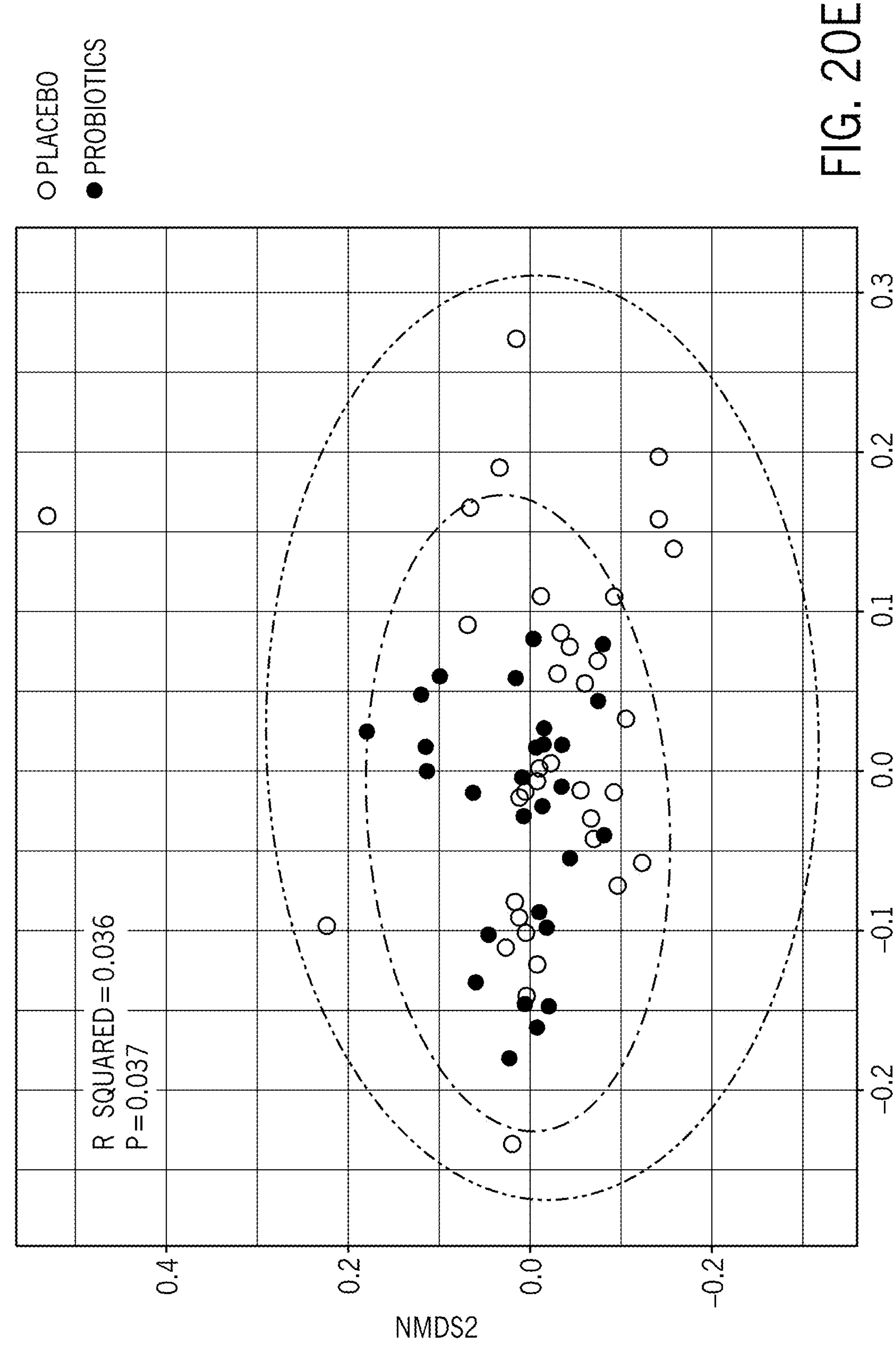
Figure 21A:
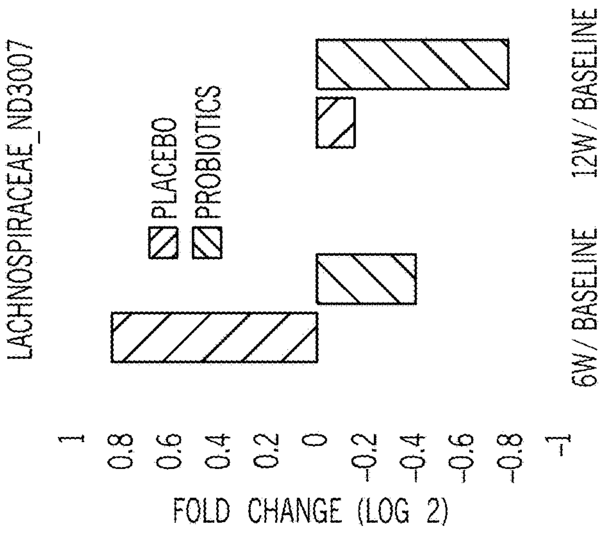
FIG. 21A-21I. Fold change of relative abundance at genus/species level over the course of intervention for the probiotics group (blue) and placebo (orange) for the study on *B. lactis*. Each bar represents the log 2 transferred relative change of gut microbial abundance of 6 and 12 weeks compared with the baseline. Significant differences are marked with * to indicate P<0.05.
Figure 21B:
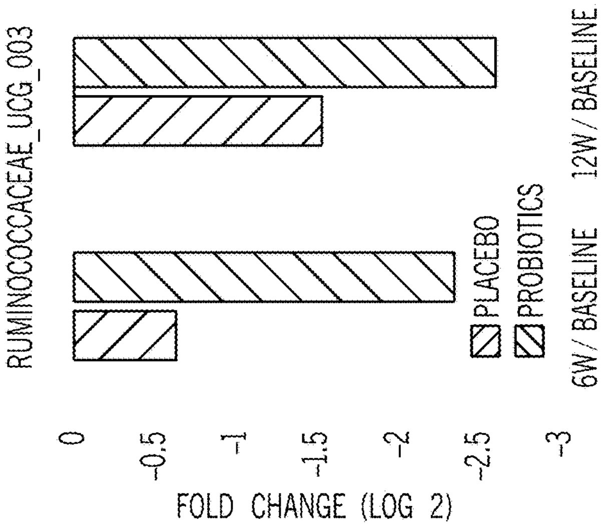
Figure 21C:
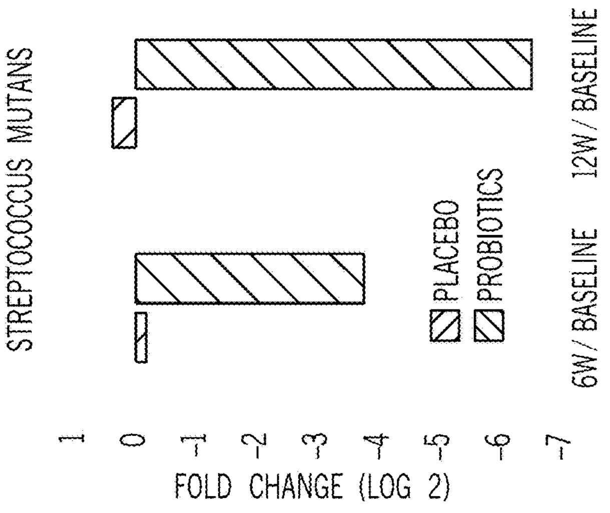
Figure 21D:
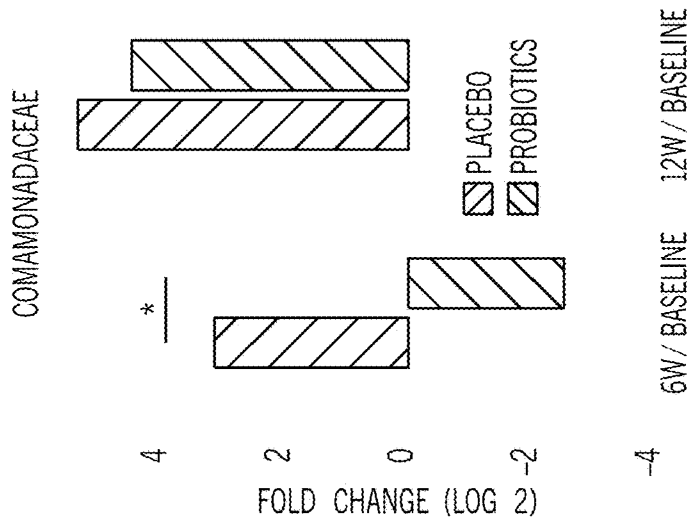
Figure 21E:
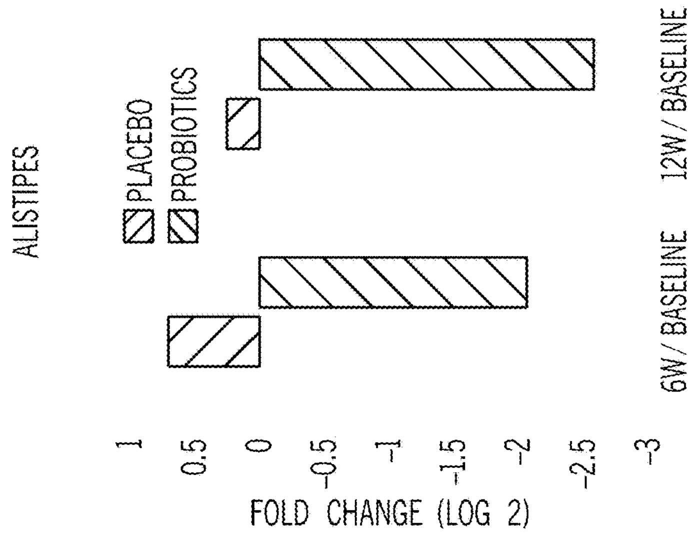
Figure 21F:
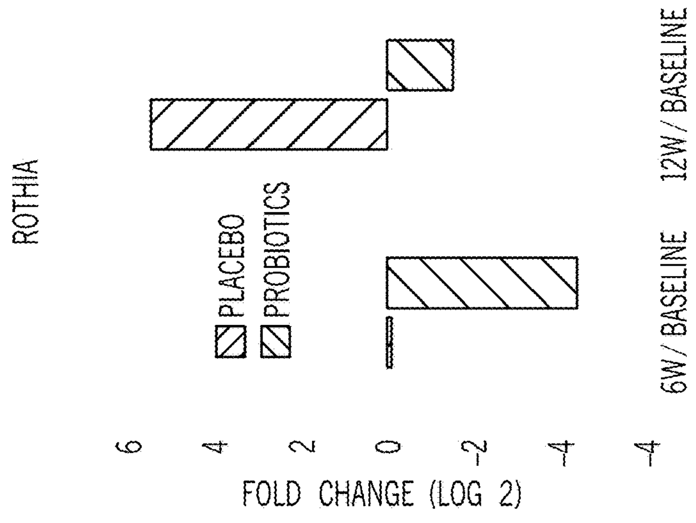
Figure 21I:
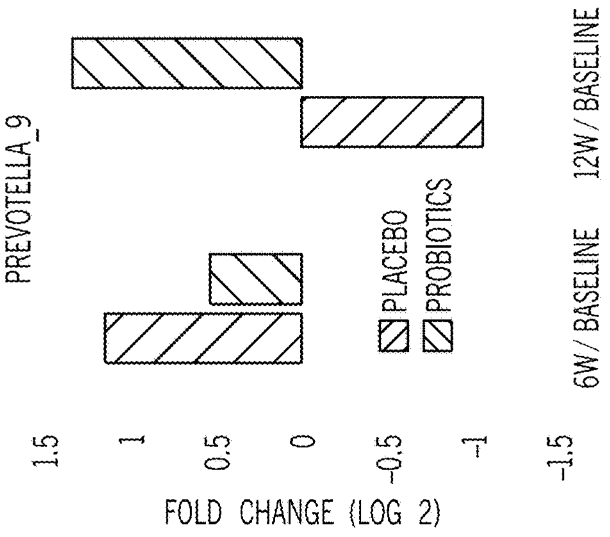
Figure 21H:
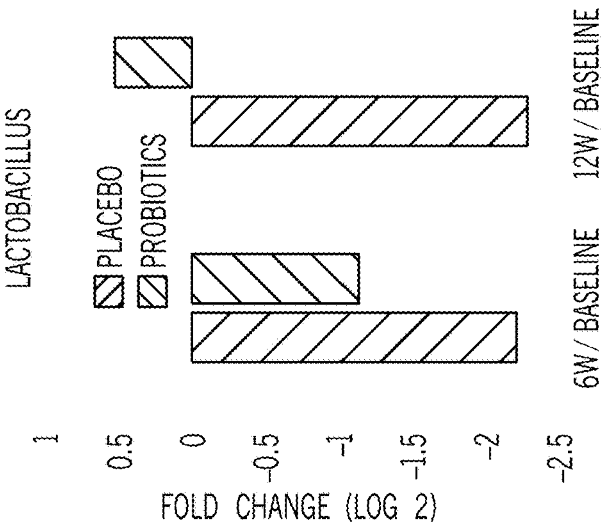
Figure 21G:
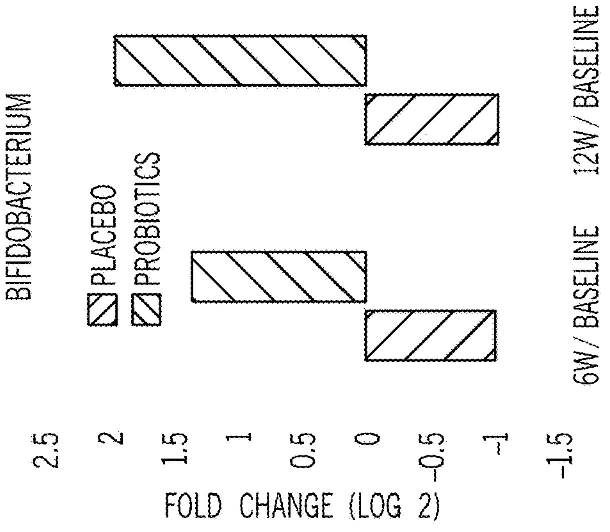
Figure 22C:
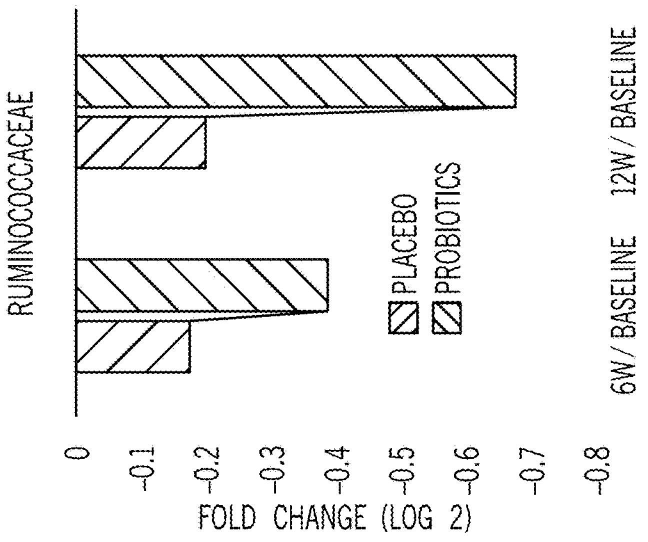
FIG. 22A-22I. Fold change of relative of abundance at family level for the study on *B. lactis*. Each bar represents the log 2 transferred relative change of gut microbial abundance compared with the baseline at 6 and 12 weeks.
Figure 22B:
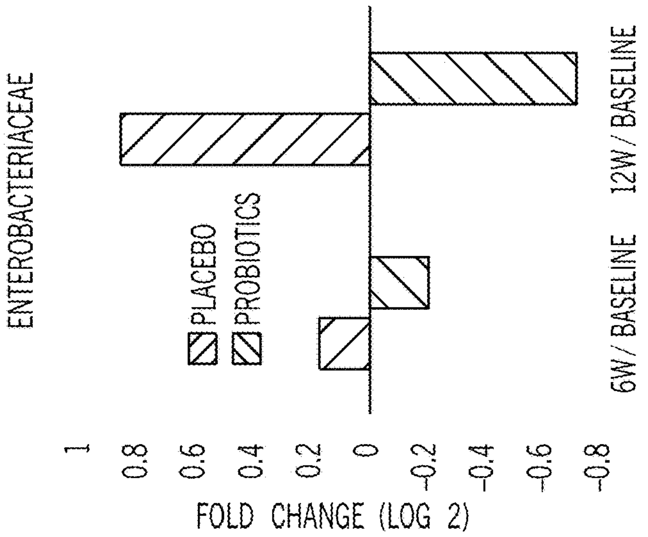
Figure 22A:
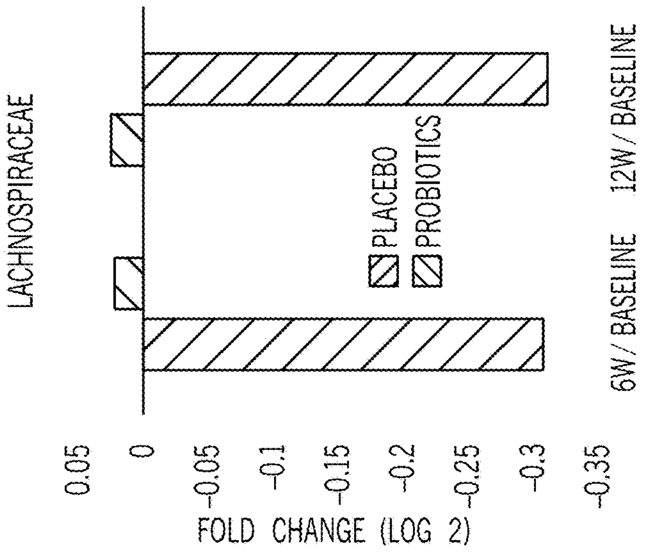
Figure 22D:
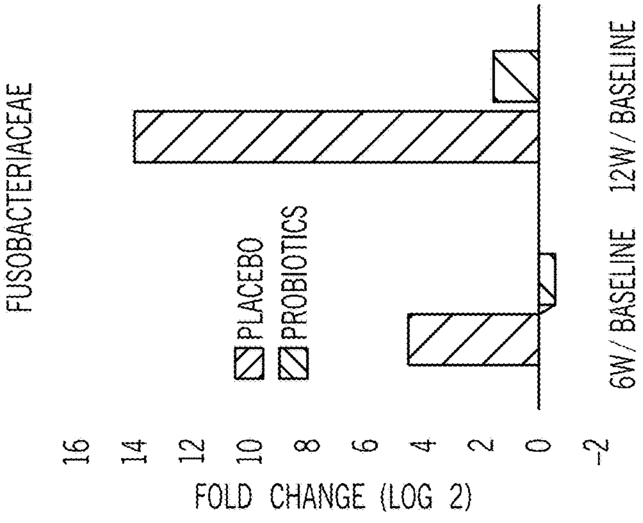
Figure 22E:
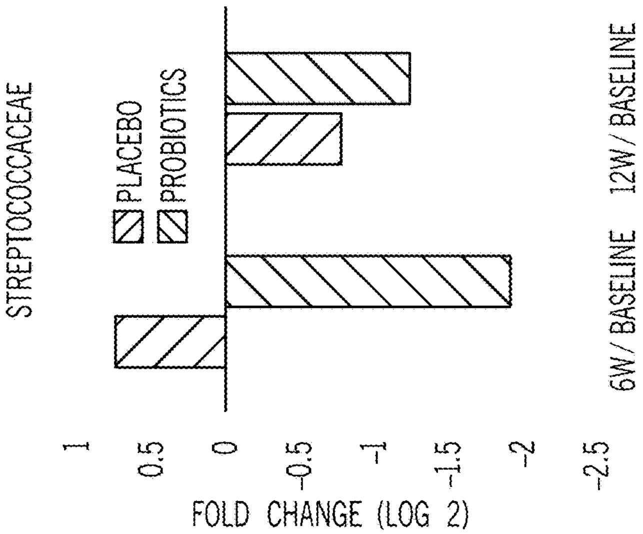
Figure 22F:
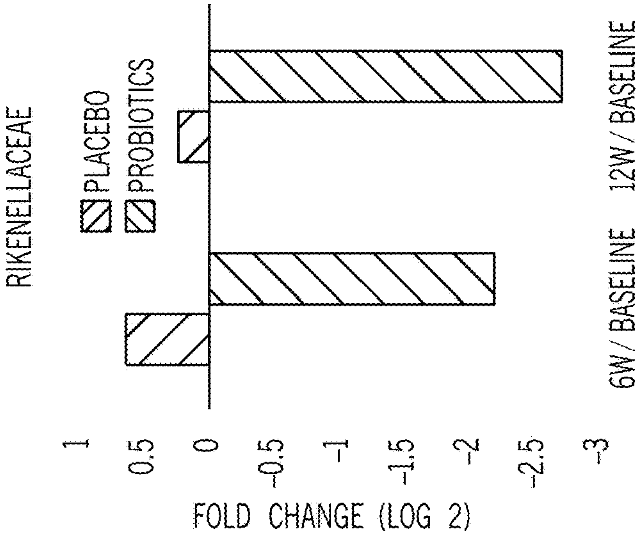
Figure 22G:
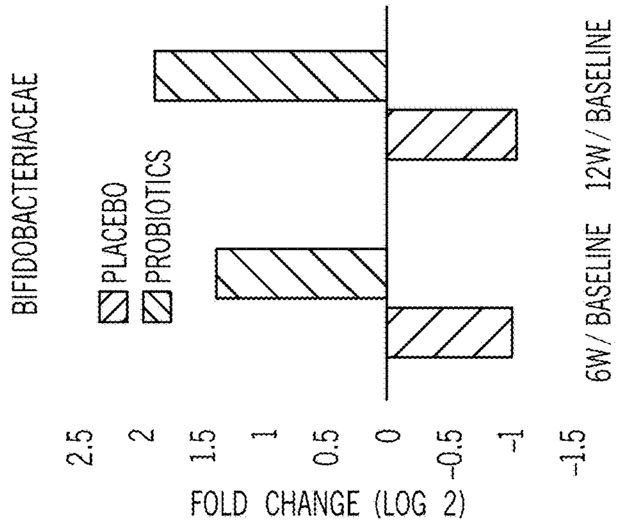
Figure 22H:
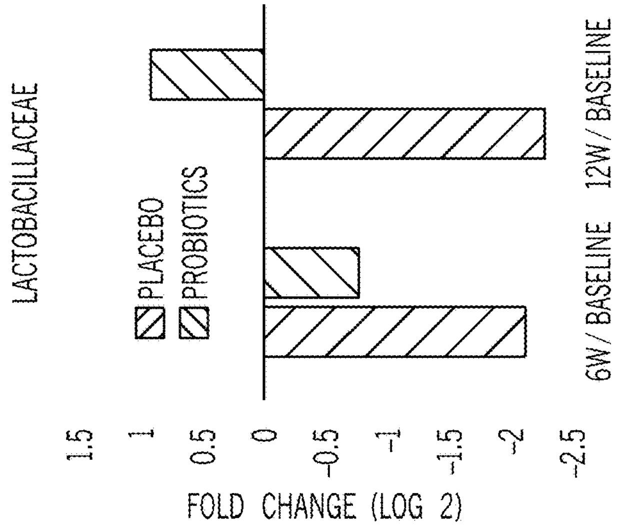
Figure 22I:
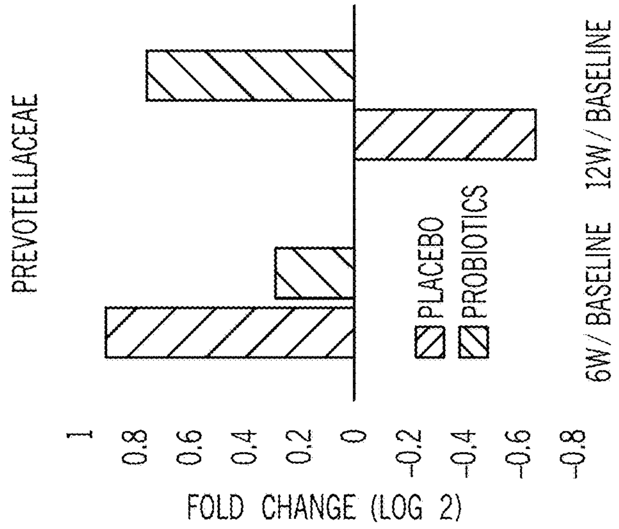

After sequencing, we obtained a total of 3,088,722 raw reads and an average of 49,818 reads per sample (range=29, 329-119,440 reads). Overall phylum and genus level variations in gut microbiota composition over the intervention course are shown in FIG. 19 for both probiotics and placebo groups.

α diversity slightly but significantly increased in the probiotics group compared with the placebo group after 6 weeks (FIG. 20A-D). β-diversity, analyzed by a permutational multivariate ANOVA (PERMANOVA), showed a significant separation with probiotics treatment (F-statistic=2.2526; $R^2$=0.035613; P<0.05, NMDS Stress=0.19048, FIG. 20E).

In order to characterize the change in abundance of potentially clinically significant bacteria over the intervention course, we presented the fold changes of several selected bacterial genera and families in FIG. 21. The relative abundances of Lachnospiraceae ND3007, Ruminococcaceae UCG-003, *Streptococcus mutans*, Comamonadaceae, *Alistipes*, and *Rothia* showed decreasing trends from baseline levels in the probiotics group at both 6 and 12 weeks (FIG. 21A-F). Among such bacterial taxa, only Comamonadaceae showed a significant decrease among probiotic group subjects at 6 weeks compared to baseline levels (FIG. 21D, P<0.05). In contrast, *Bifidobacterium, Lactobacillus*, and *Prevotella* 9 were increased from baseline at 12 weeks in the probiotics group (FIG. 21G-I). At the family level, we found similar trends in both groups (FIG. 22).

Figure 23:
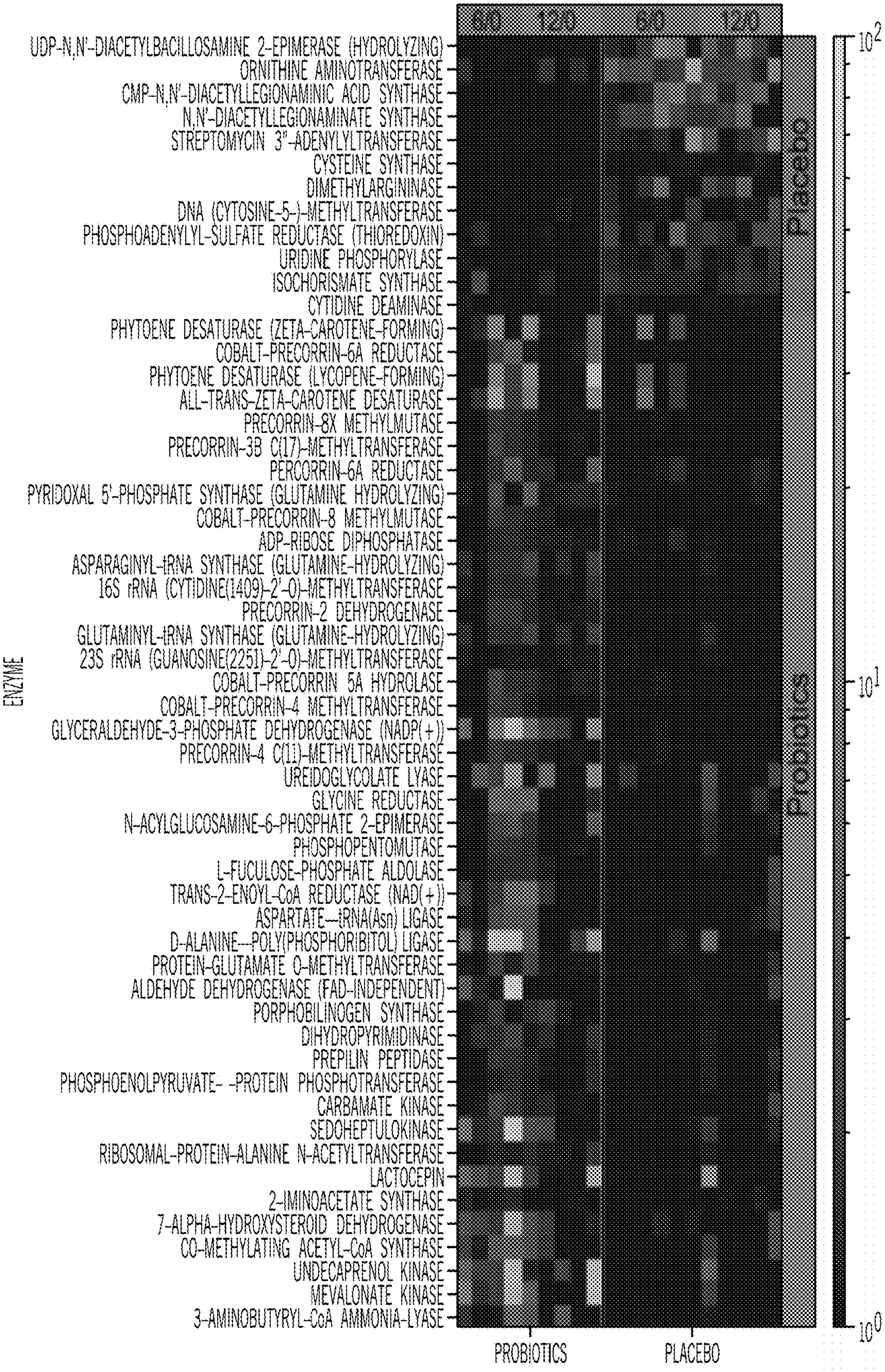
FIG. 23. The predicted KEGG enzyme abundance based on PICSRUSt2 functional gene analysis for the probiotics and placebo groups for the study on *B. lactis*. The average abundance of KEGG enzyme differentially enriched in placebo and probiotics according to level 3.
Figure 24:
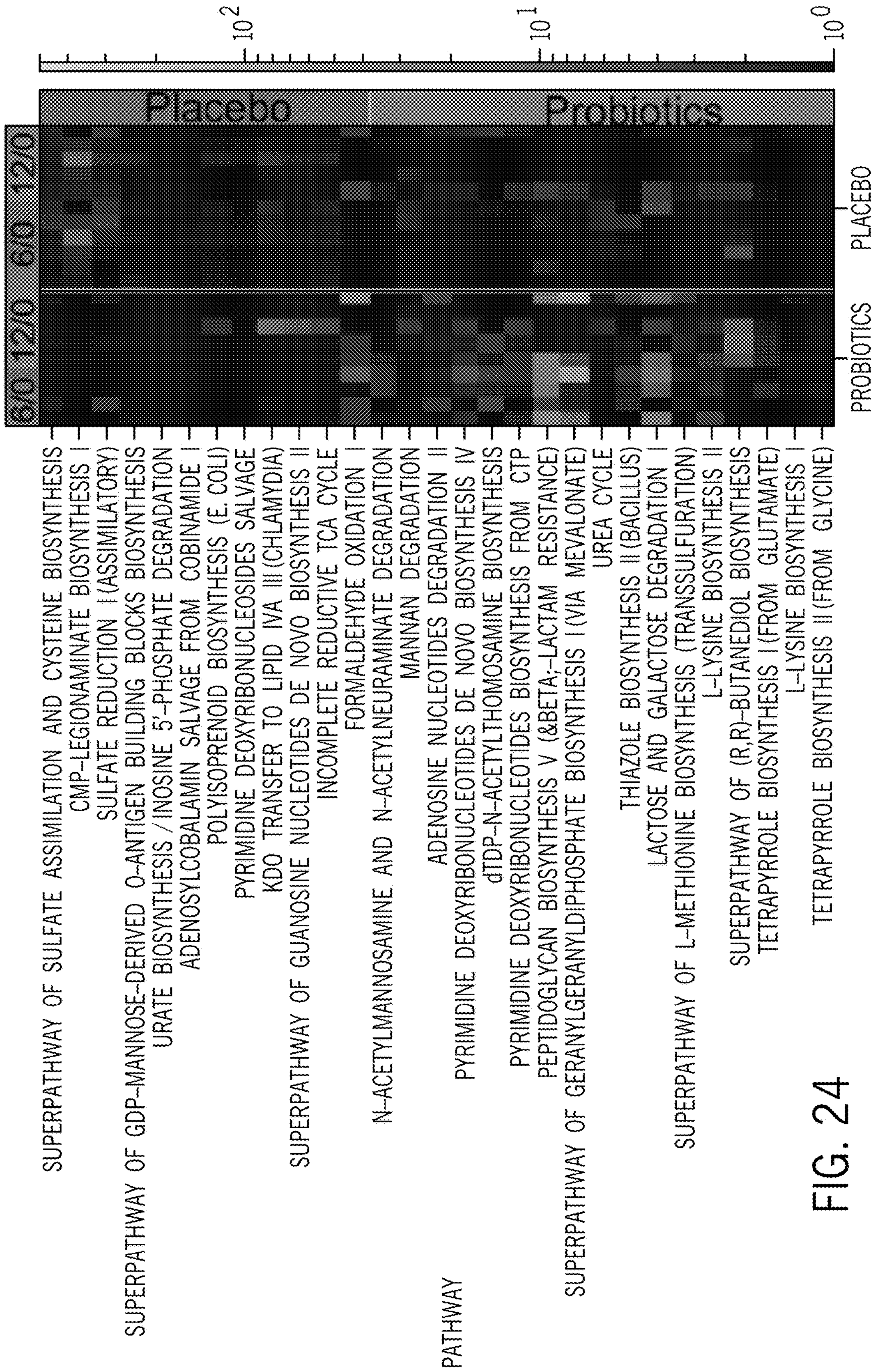
FIG. 24. Comparison of the predicted KEGG pathway in placebo and probiotics groups for the study on *B. lactis*. The average abundance of KEGG pathway differentially enriched in placebo and probiotics according to level 1.
Figure 25:
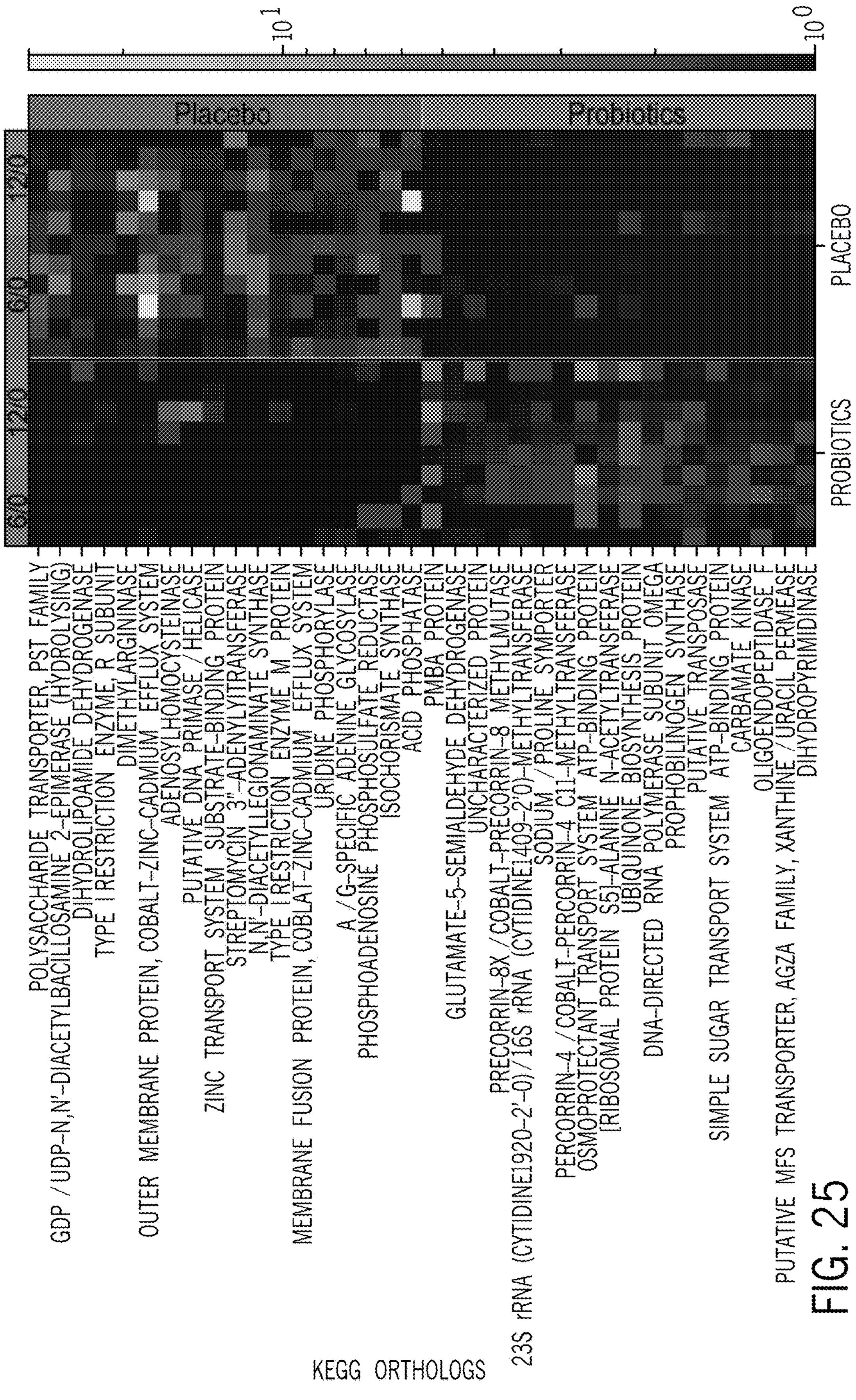
FIG. 25. Comparison of the predicted KEGG orthologous (KO) between placebo and probiotics groups for the study on *B. lactis*. The average abundance of KEGG pathway differentially enriched in placebo and probiotics according to level 2.

Functional gene predictive analysis indicated that several genes had different abundances in the probiotics group after the 12-week treatment period. Notably, genes encoding the ubiquinone biosynthesis protein (ubiB, k03688), phytoene desaturase (EC:1.3.99.29), phytoene desaturase (lycopene-forming) (EC:1.3.99.31), and all-trans-zeta-carotene desaturase (EC:1.3.99.26) were all upregulated, while the genes encoding dimethylargininase (k01482) and acid phosphatase (phoN, k09474, EC:3.1.3.2) were downregulated (FIG. 23). These findings do not meet the false discovery criteria for significance with multiple comparisons. The analysis results from the predicted KEGG pathway, shown in FIG. 24, and the predicted KO, shown in FIG. 25, further compare the gene expression of the probiotics and placebo groups.

4. Correlation Between Gut Microbiota Abundances and Clinical Indices

Figure 26:
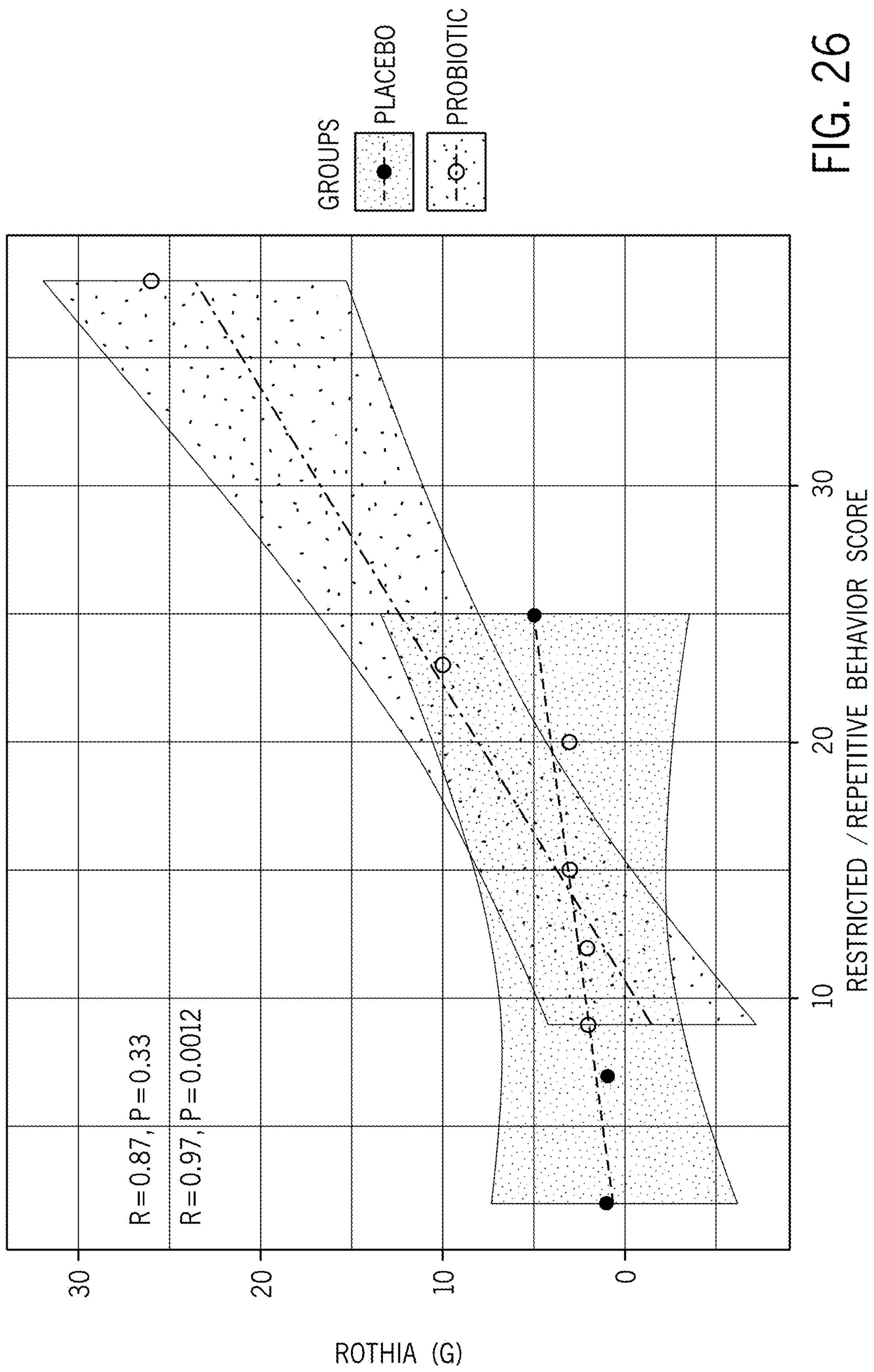
FIG. 26. Correlation between the abundance of bacterial genera and clinical indices for the study on *B. lactis* using spearman's method was performed for the probiotics (blue) and placebo (yellow) group at the 6-week time point. Probiotic group showed positive correlation between RRB scores and *Rothia* (R=0.97, P<0.005). No significant correlation was observed in the placebo group.
Figure 27:
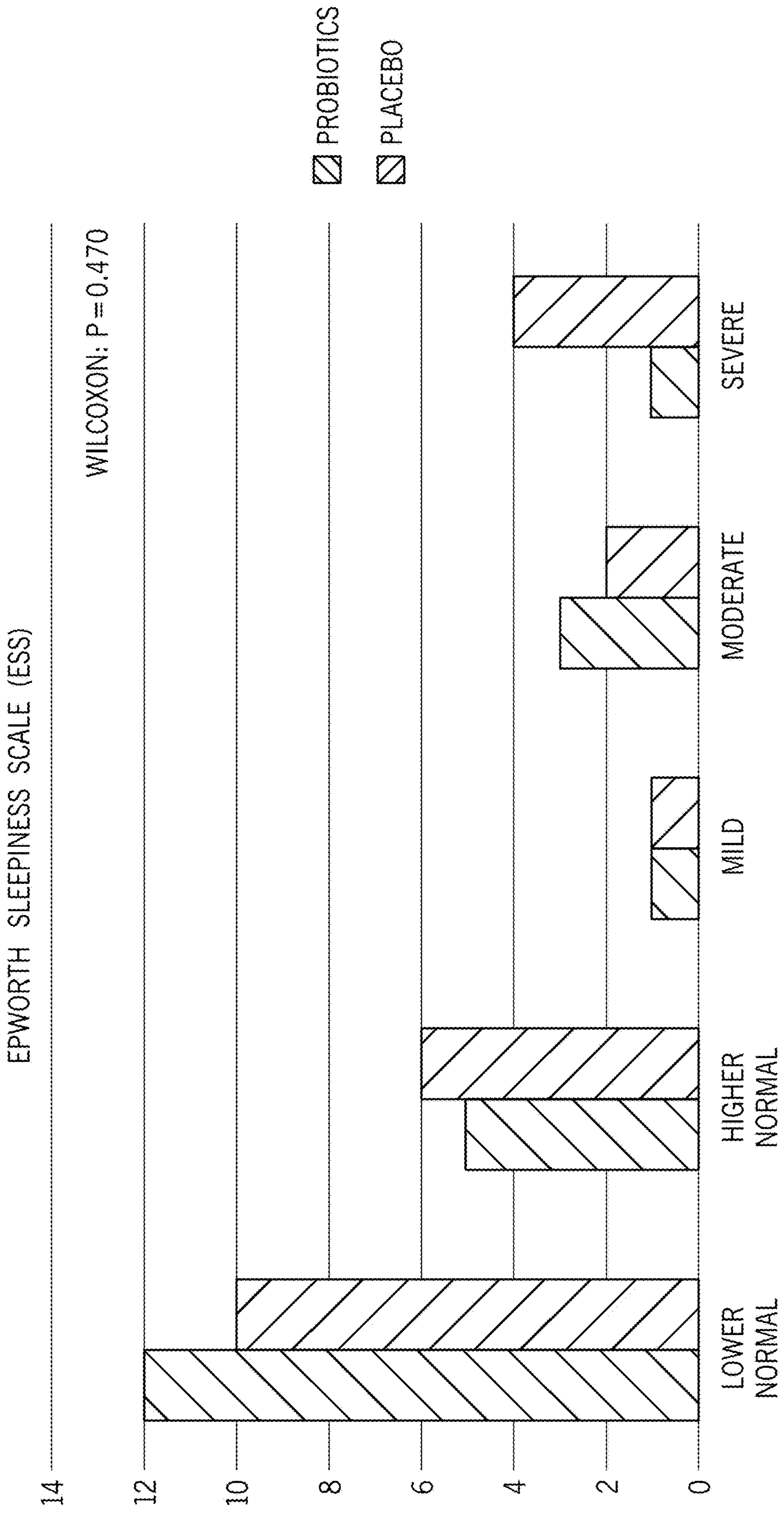
FIG. 27. Epworth Sleepiness Scale (ESS) at baseline between two groups for the study on *B. lactis*. Comparison of ESS scores at baseline between probiotics group (blue) and placebo group (yellow). There was no difference in sleepiness level found between groups (p>0.05).
Figure 28:
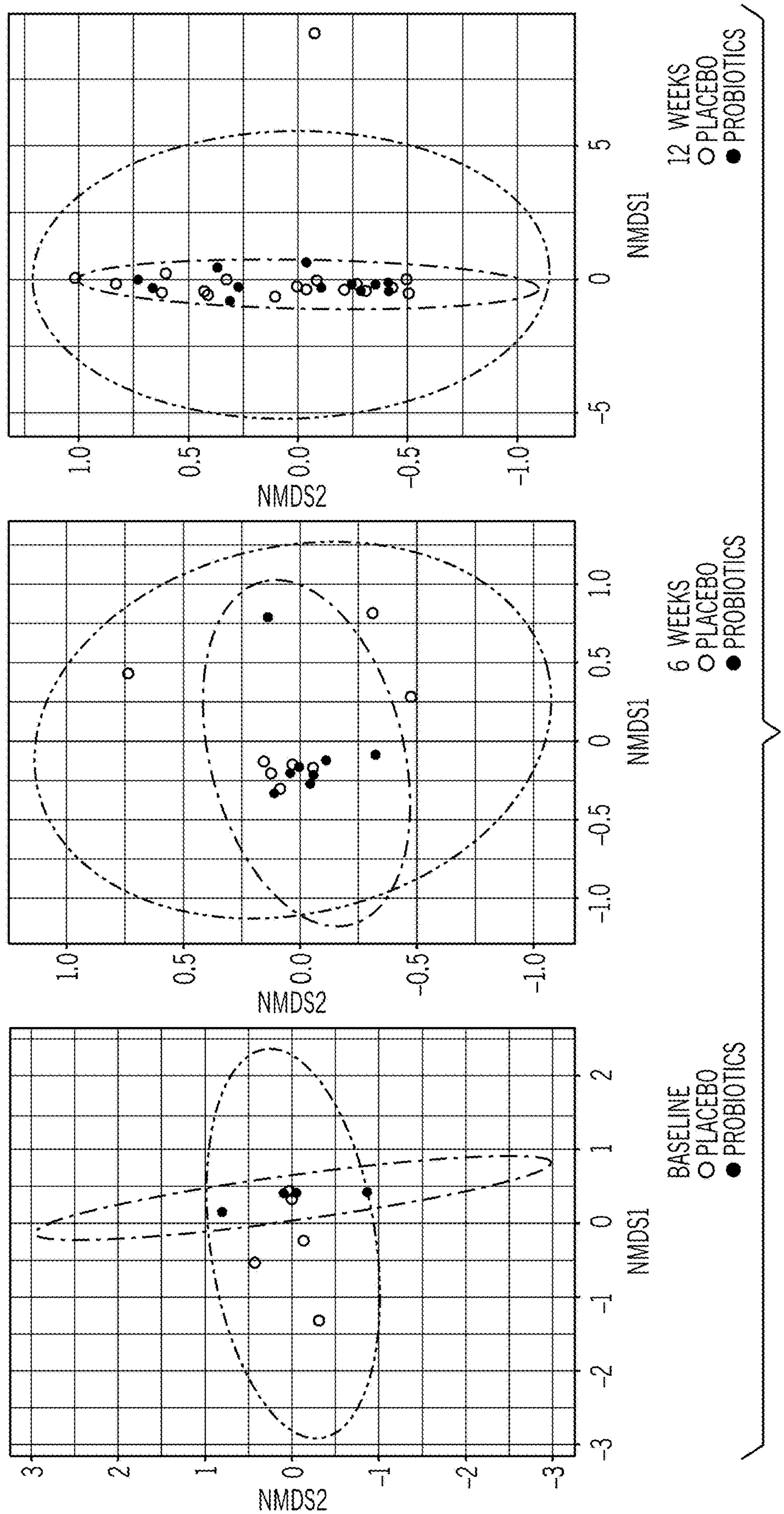
FIG. 28. Gut microbiome community clustering in fecal samples derived from PWS subjects consuming placebo or probiotics as baseline, 6 or 12 weeks shown with nonmetric multidimensional scaling (NMDS) on a Bray-Curtis dissimilarity matrix in the study on *B. lactis*.
Figure 29B:
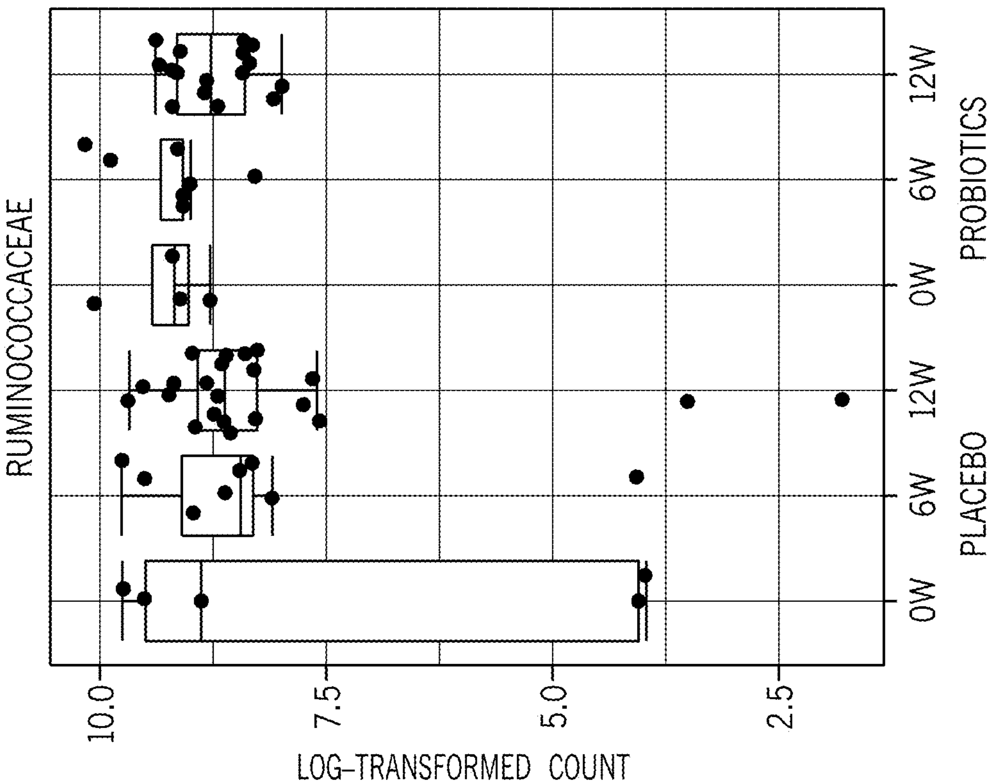
FIG. 29A-29J. Relative abundance plots of the family level of gut microbiota composition in subjects consuming probiotics or placebo at baseline, 6 and 12 weeks for the study on *B. lactis*. (A-D) Family level analysis; (E-J) Genus level analysis in the study on *B. lactis*.
Figure 29A:
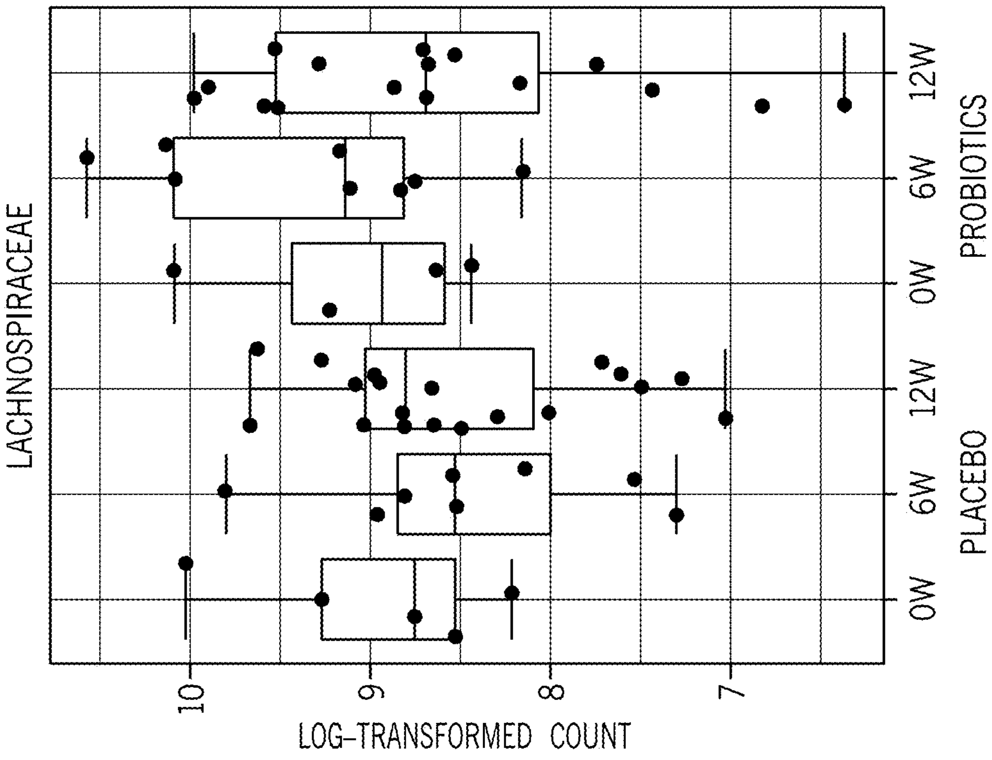
Figure 29C:
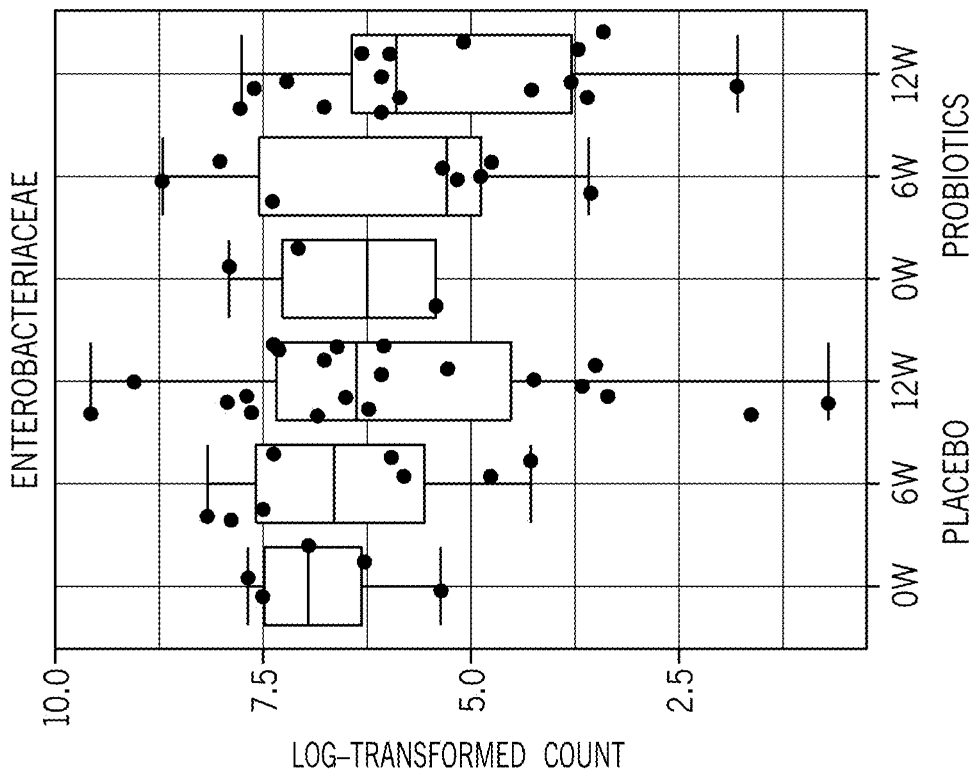
Figure 29D:
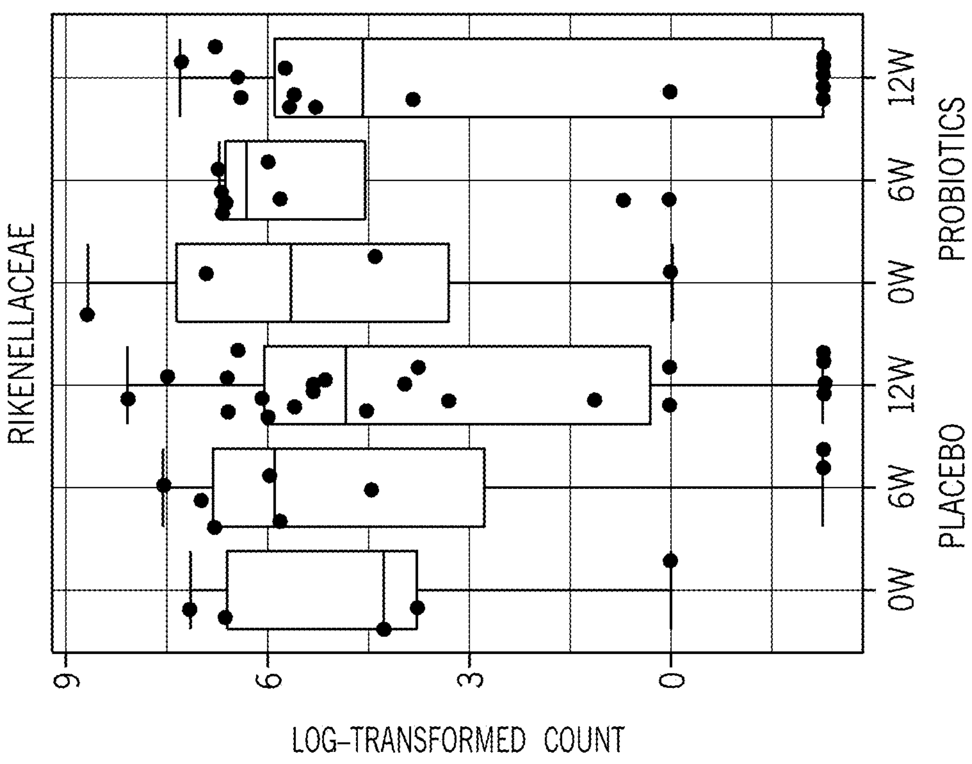
Figure 29E:
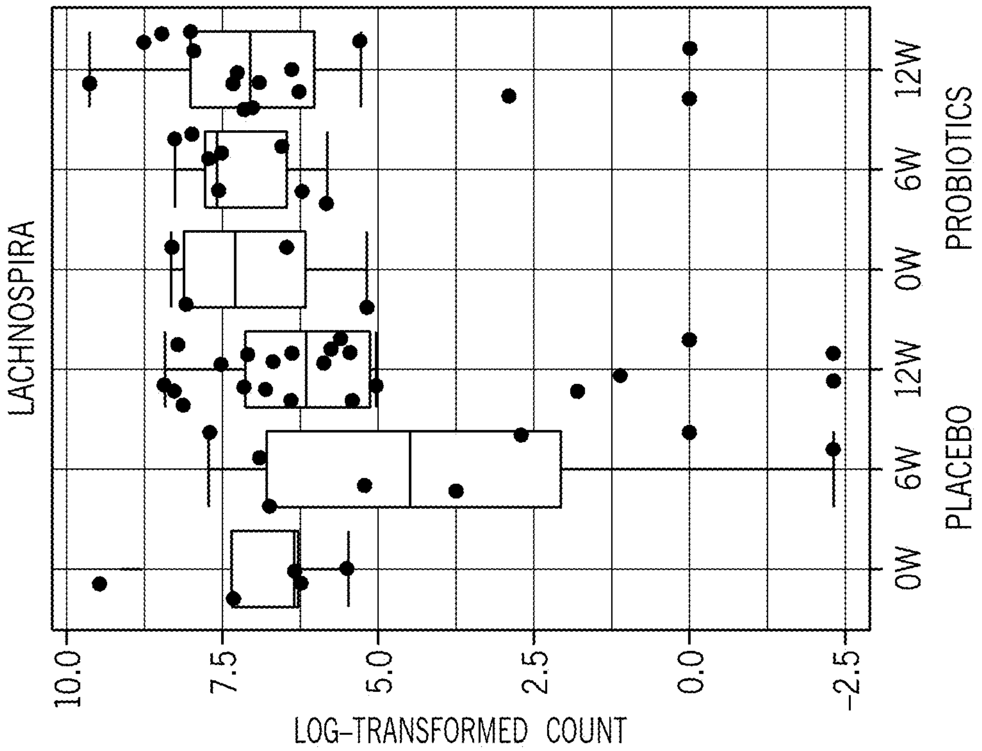
Figure 29F:
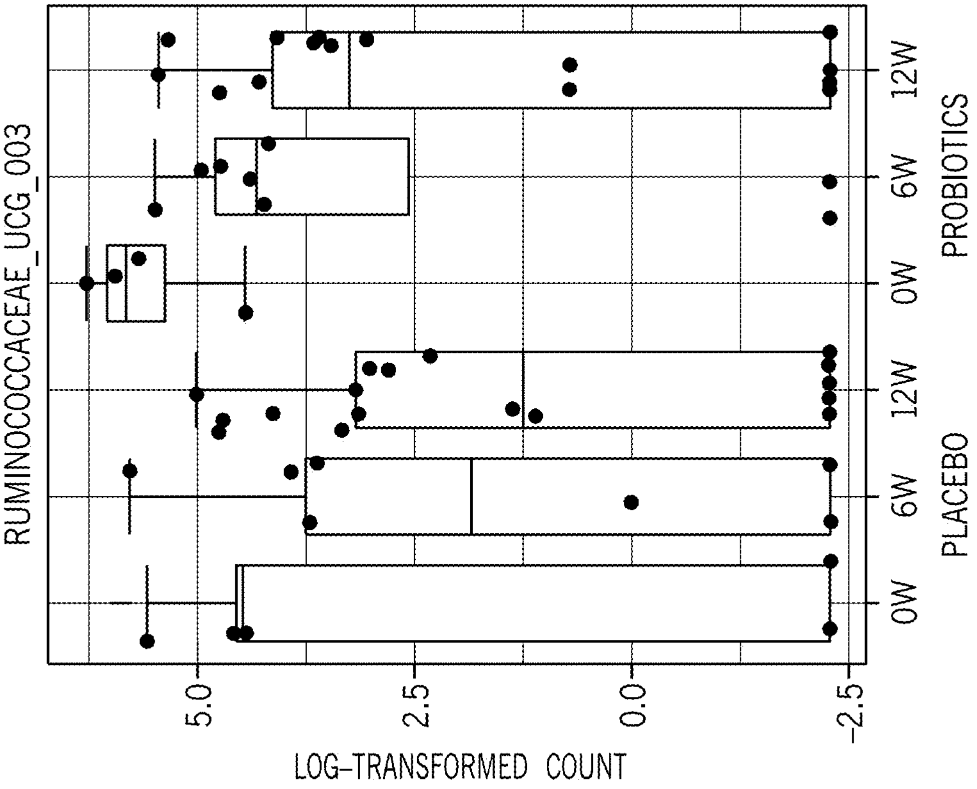
Figure 29G:
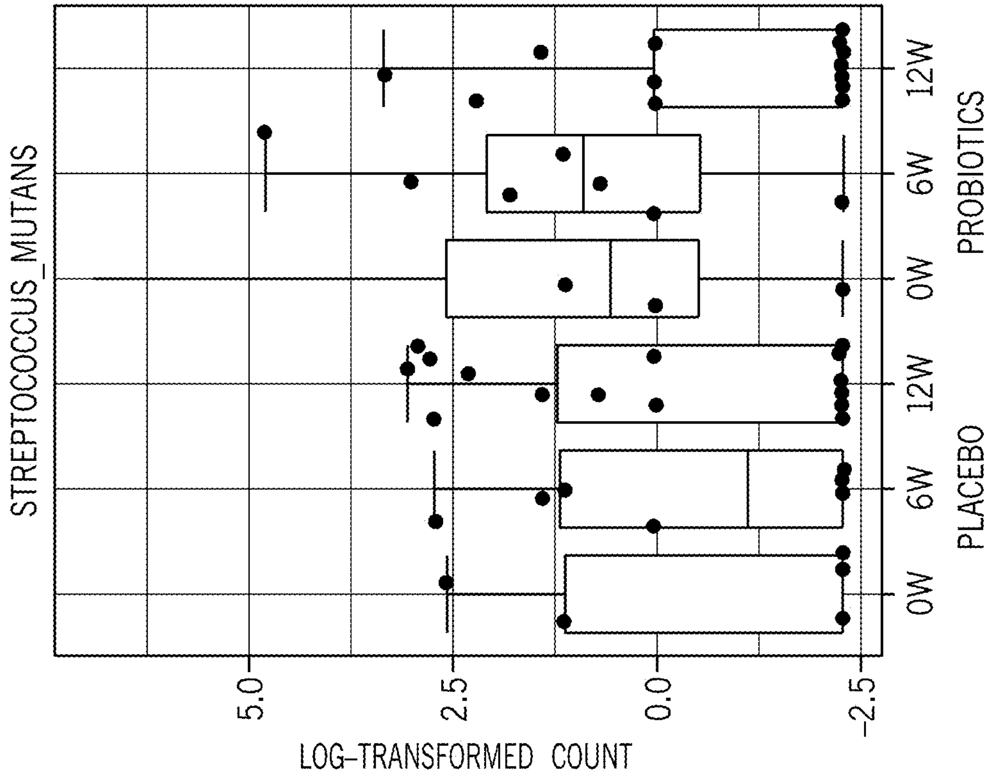
Figure 29H:
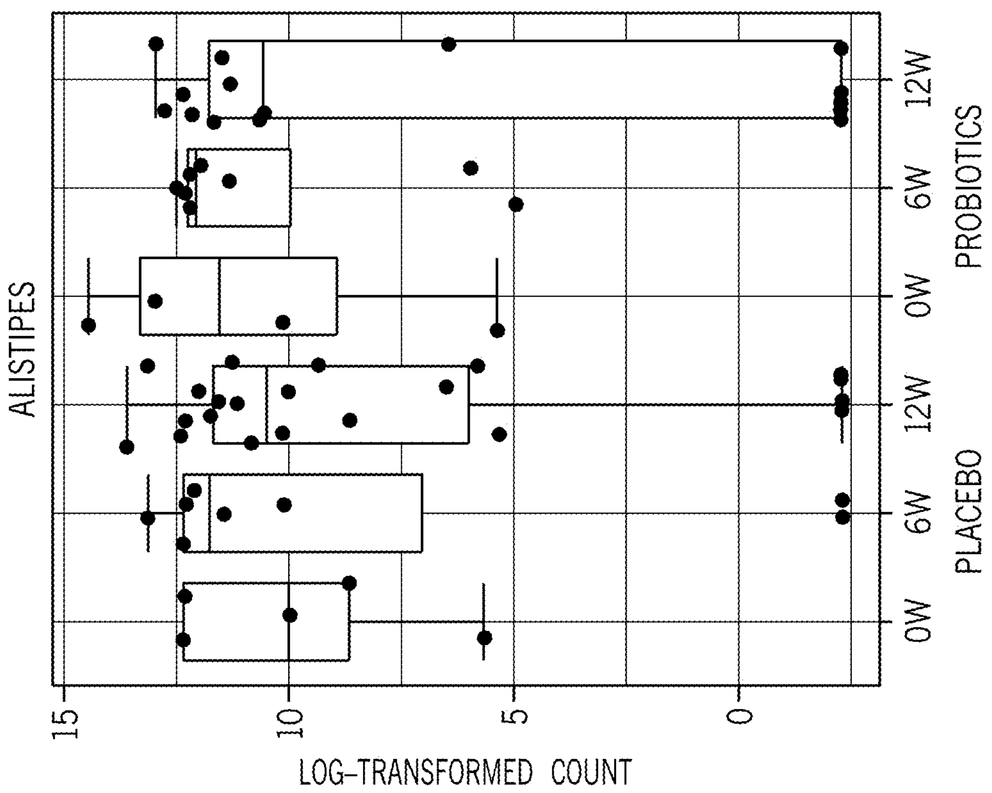
Figure 29I:
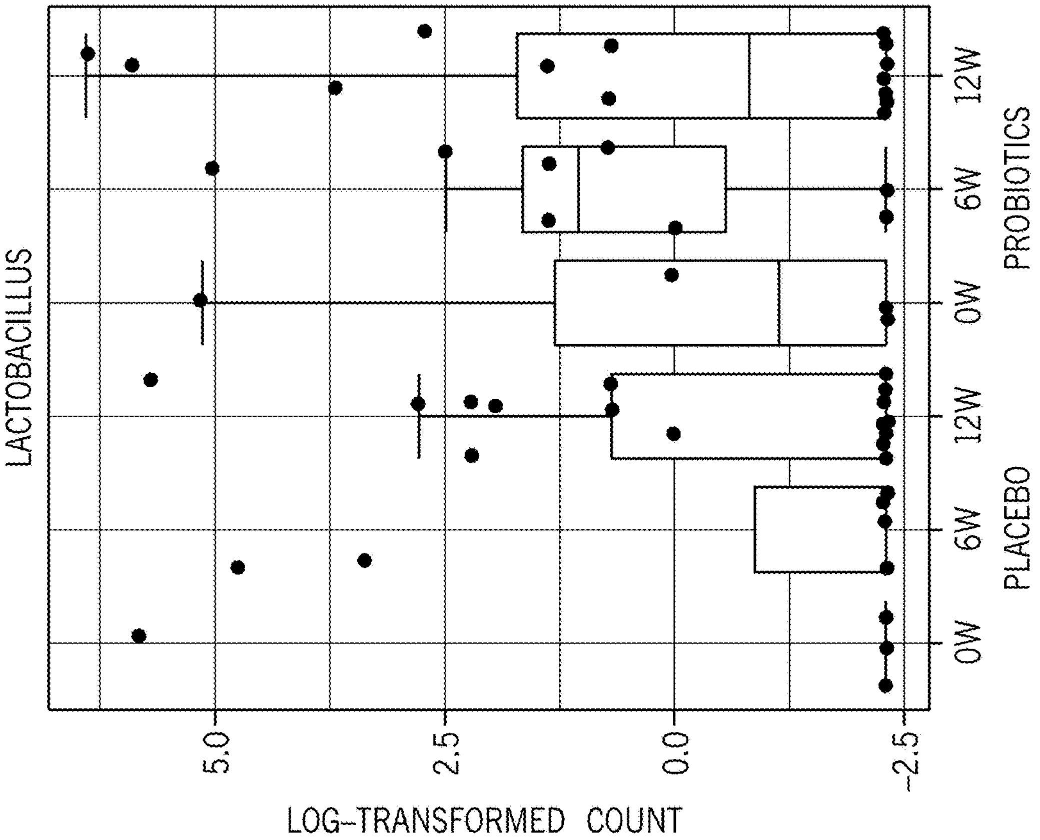
Figure 29J:
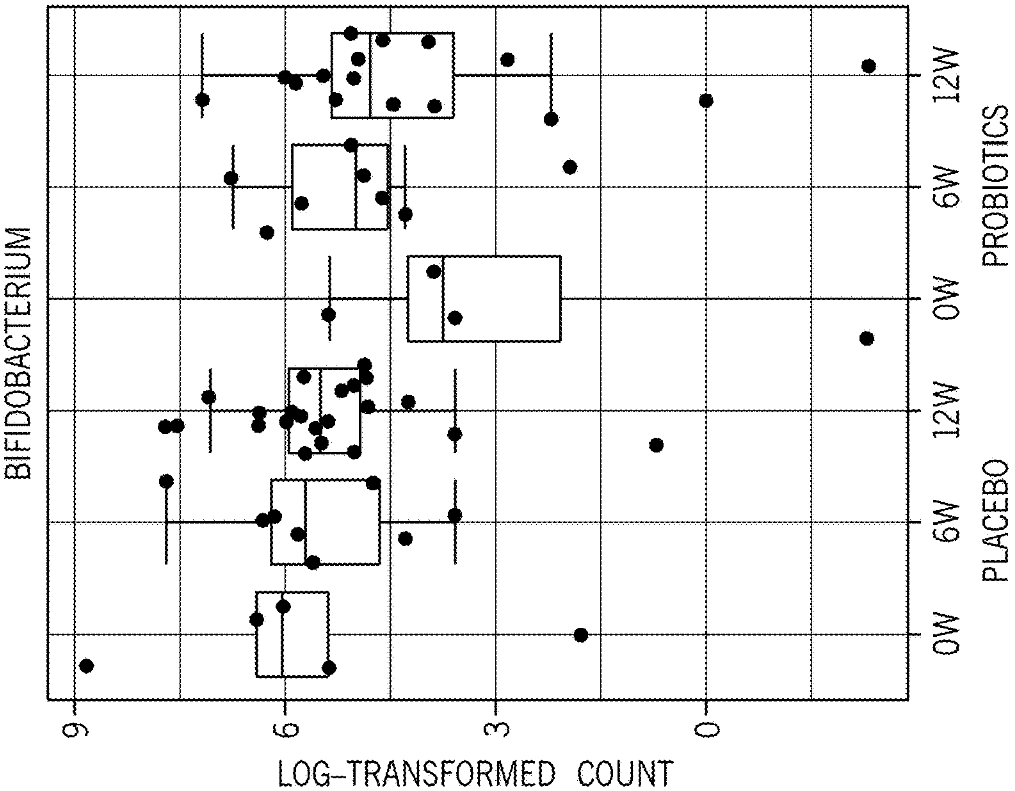
Figure 30A:
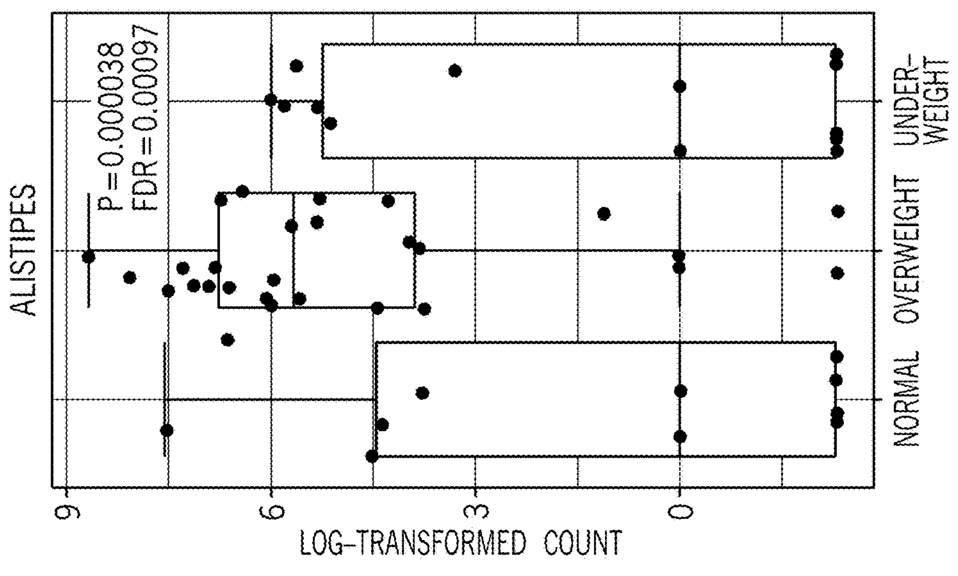
FIG. 30A-30D. Important gut microbial related to obesity at genus level for the study on *B. lactis*. (A-C) The relative abundances of genus related to obesity. (D) The overall composition of gut microbiome in normal and abnormal weight groups were showed significant divided (F-statistic=1.7239; R2=0.067015; P=0.011). PERMANOVA result labeled.
Figure 30B:
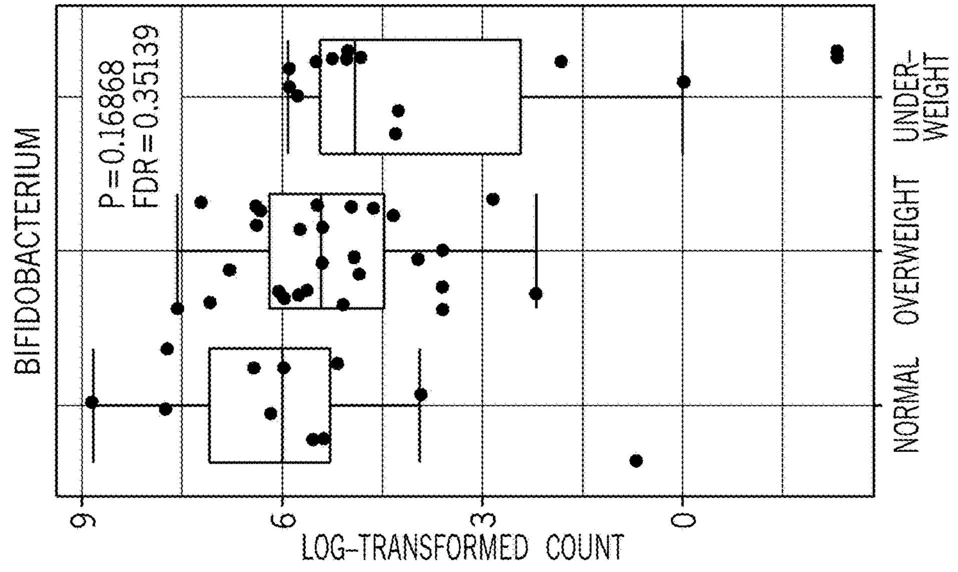
Figure 30C:
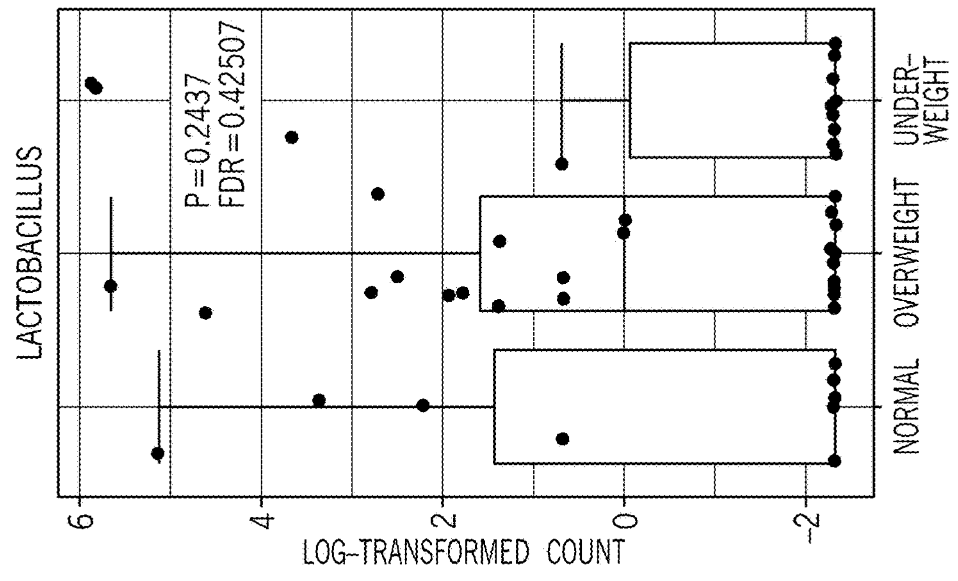
Figure 30D:
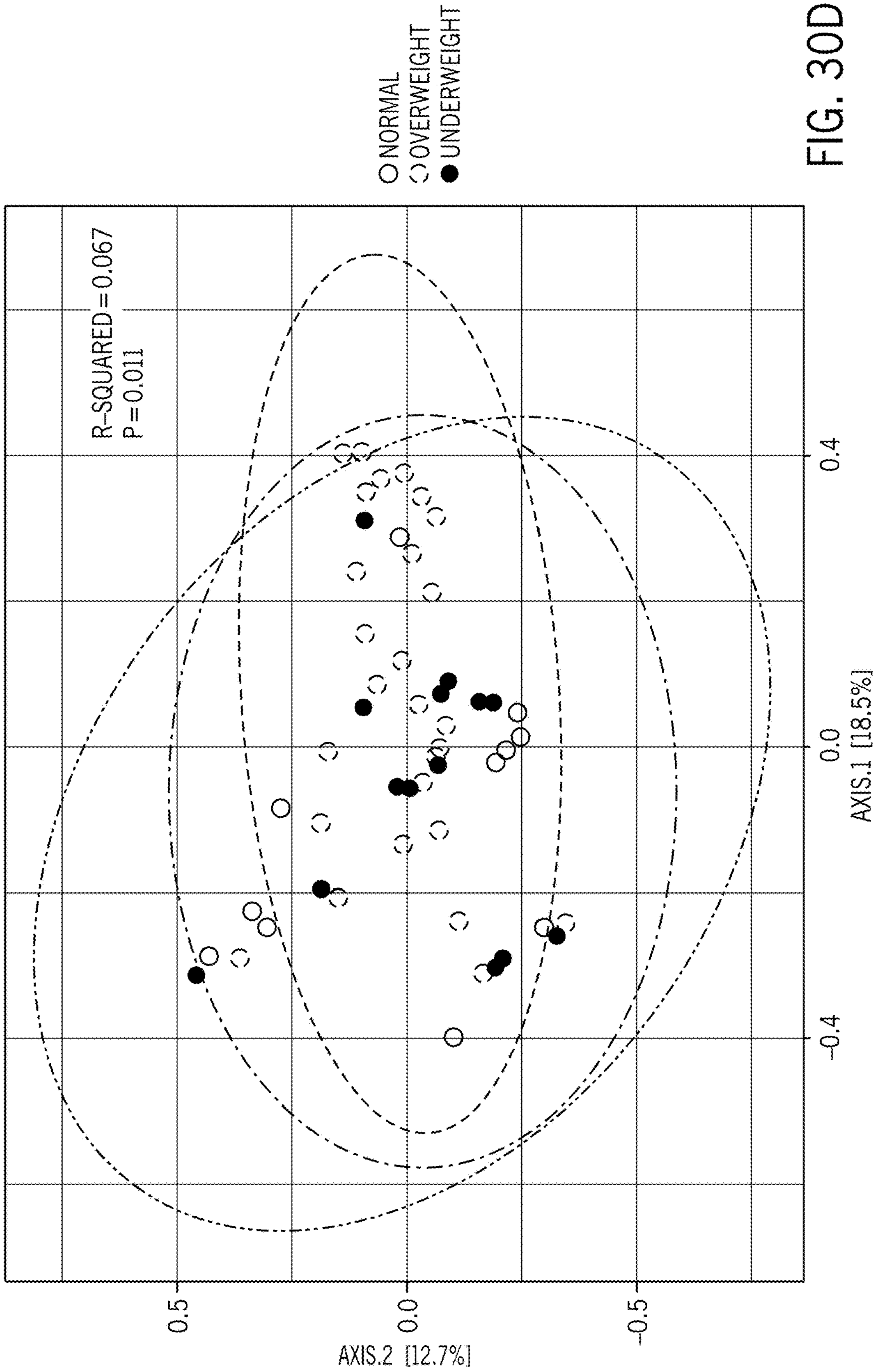
Figure 31A:
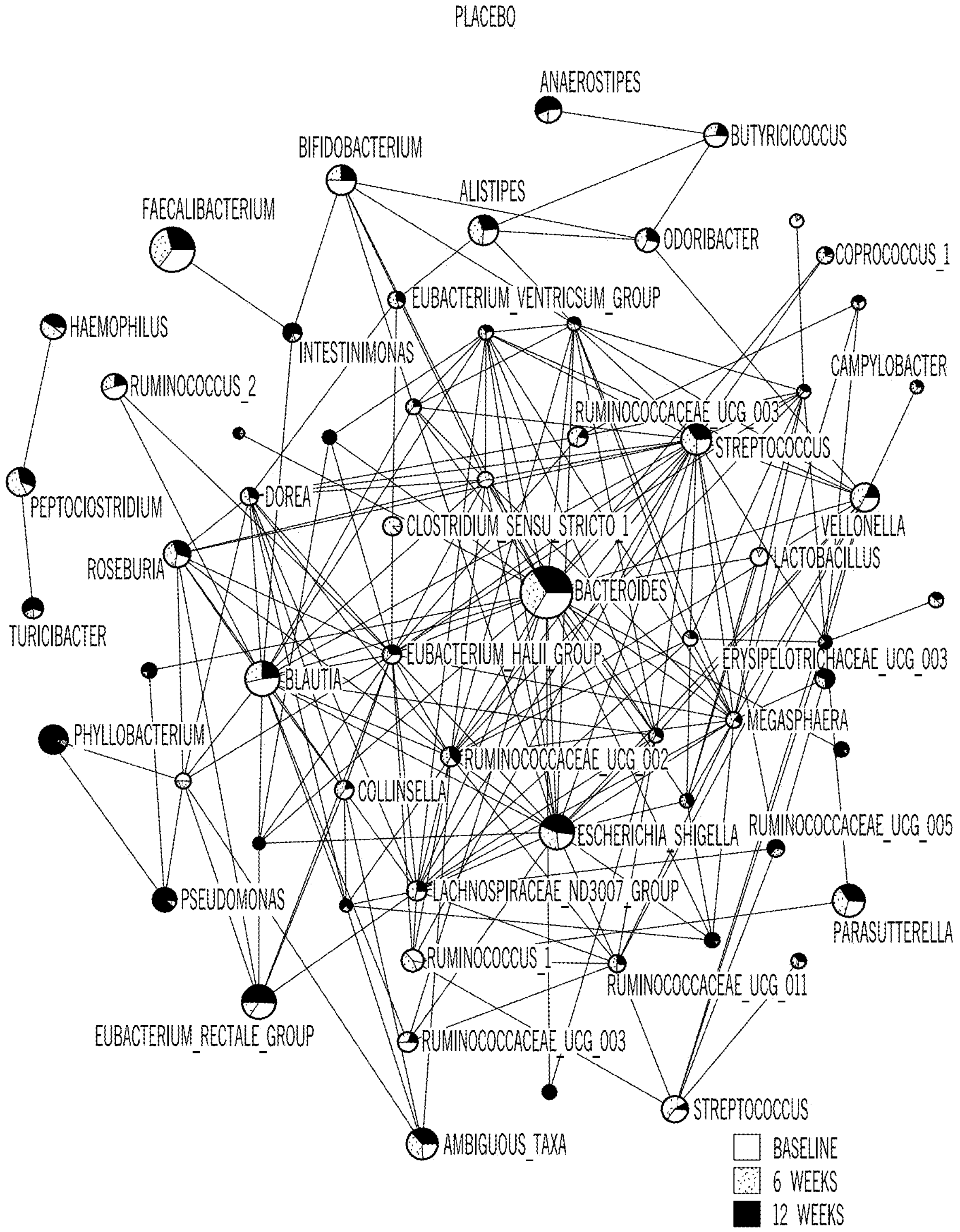
FIG. 31A-31B. Phylogenetic genera co-occurrence network analysis showing the dominant bacterial groups associated with intervention from 3 time points between placebo (A) and probiotics (B) groups based on the SparCC correlation algorithms for the study on *B. lactis*. Each node presents a bacterial genus. Each color represents a relative abundance at different time point (green: baseline, red:6 weeks, purple:12 weeks). The node size indicates the relative abundance of each genus, and the density of the lines represents the SparCC coefficient. Each edge represents correlations between taxa pairs. Permutation of SparCC=100, p-value threshold=0.05, correlation threshold=0.5.
Figure 31B:
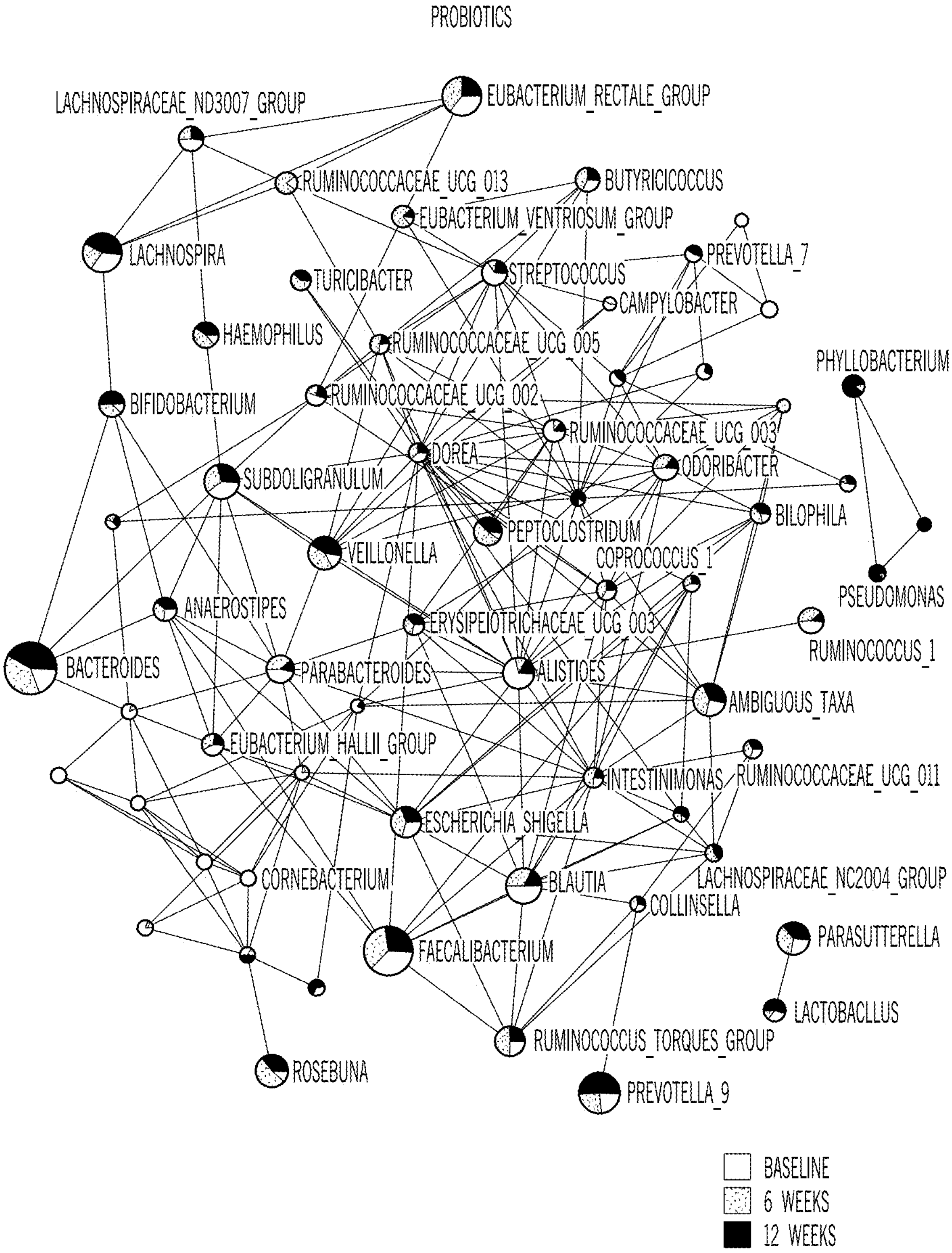
Figure 32A:
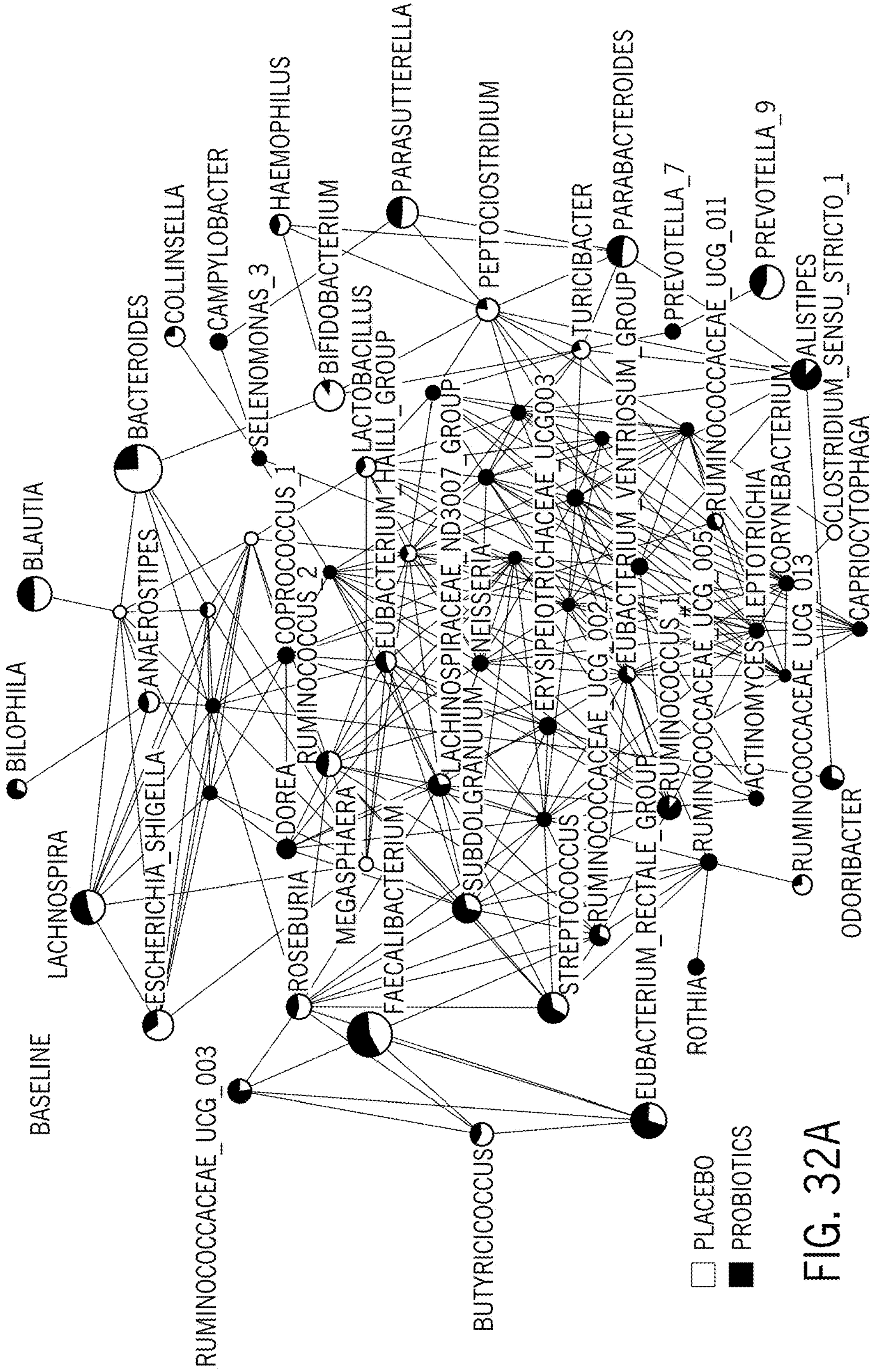
FIG. 32A-32C. Network of correlation of placebo and probiotics consuming at baseline, 6 and 12 weeks (A-C, respectively) for the study on *B. lactis.*
Figure 32B:
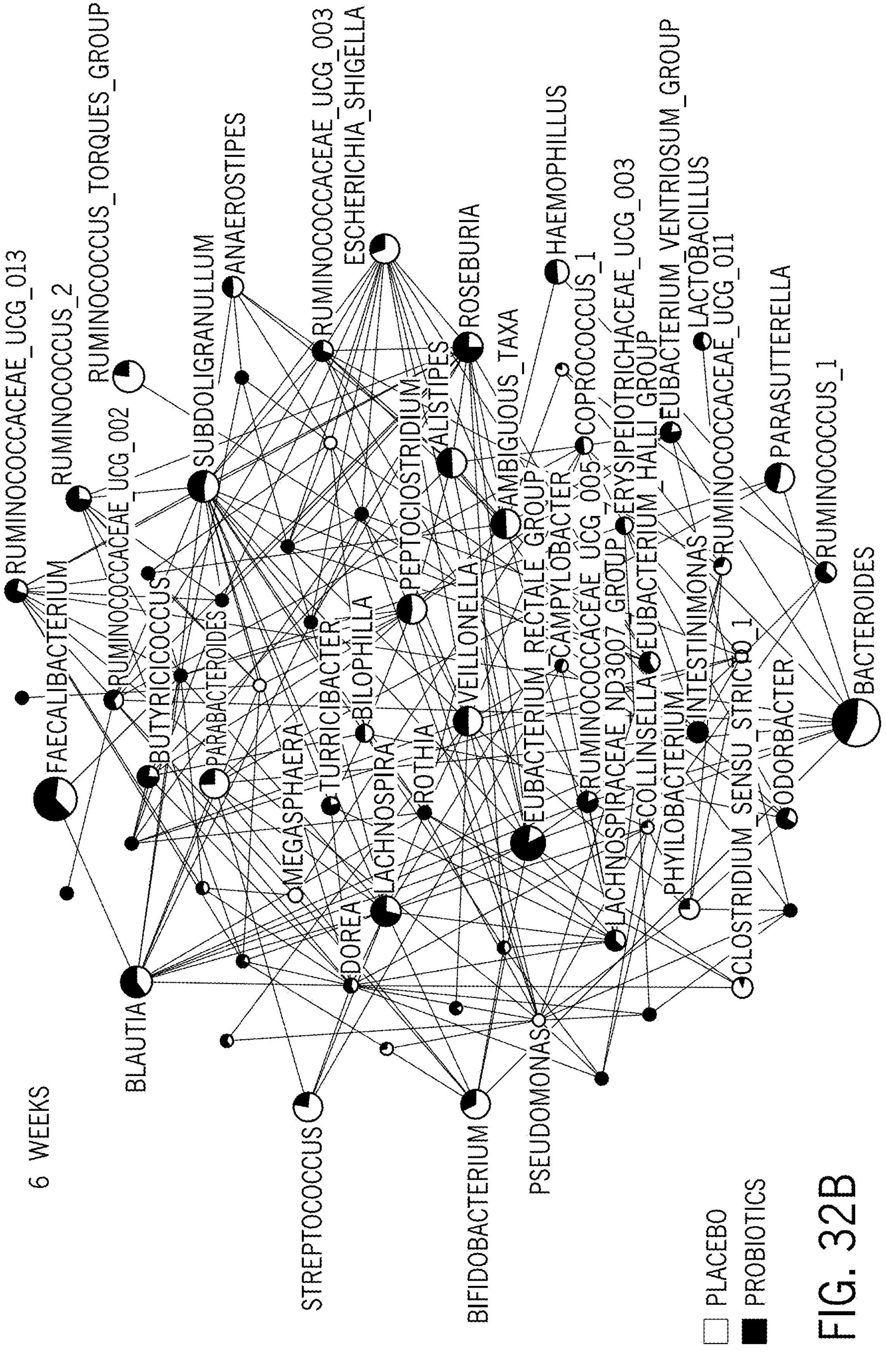
Figure 32C:
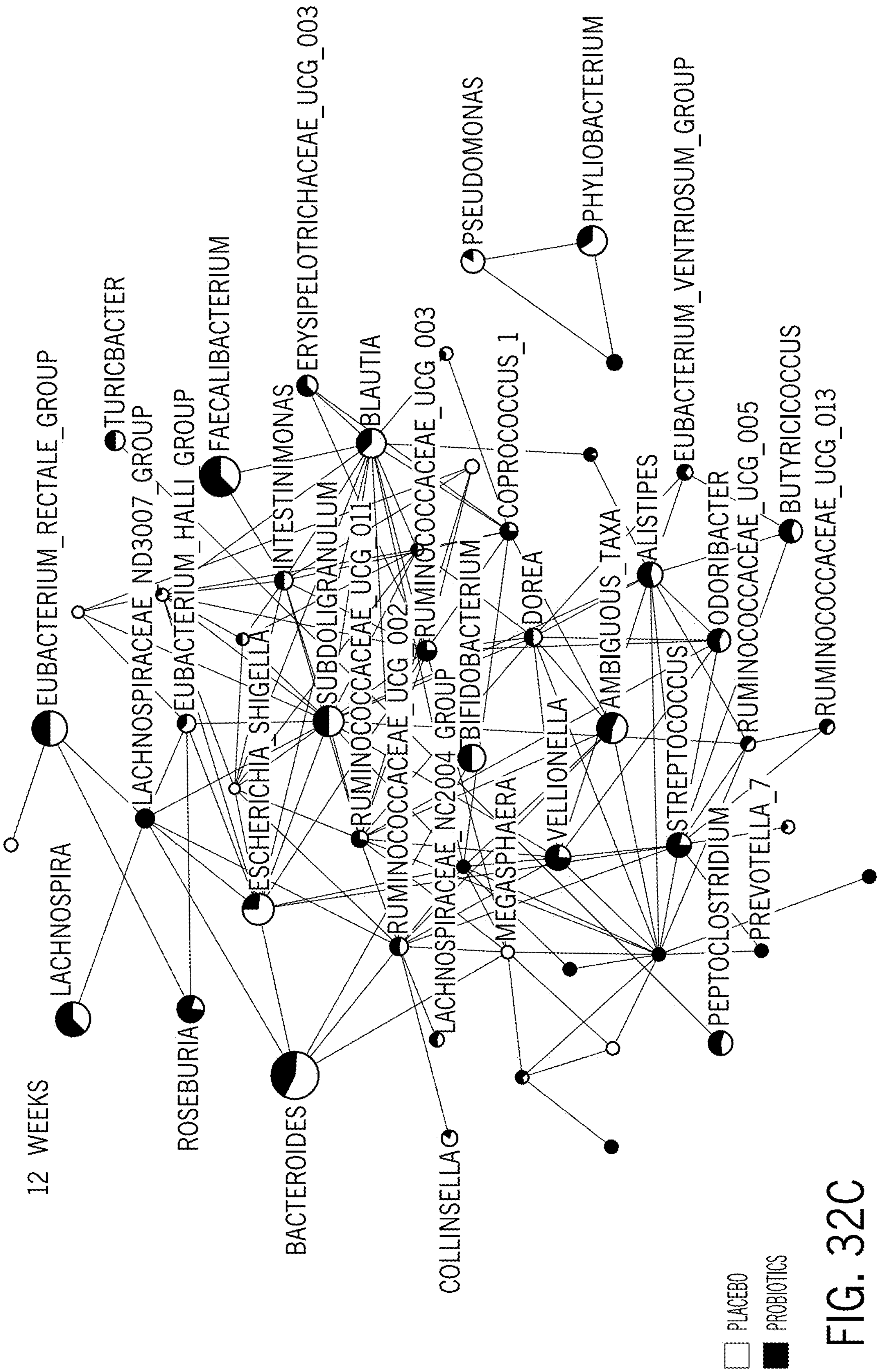

Clinical indices were correlated with the abundance of bacterial genera; one correlation was found to be significant in the probiotics group while no significant correlations were observed in the placebo group. Specifically, a positive correlation was discovered between the RRB scores and *Rothia* in the probiotics group at week 6 (FIG. 26, R=0.97, P<0.005).

Discussion

In our 12-week, randomized, double-blind, placebo-controlled trial of 65 PWS patients, BL-11 increased height in PWS subjects without changing weight. We observed that, during the treatment period, the probiotics group had a significantly greater height increase than the placebo group (p<0.05). Interventions with other probiotics in the past have failed to elicit improvement in height(Onubi et al., 2015). This study provides novel evidence for the use of BL-11 as an early intervention for patients with PWS. Interventions that lead to increased height in PWS may benefit patients at early developmental stages most and substantially improve long-term prognosis. PWS individuals were found to have absolute or functional Growth Hormone (GH) deficiency, and GH replacement is currently the most effective treatment for PWS(Bakker, Lindberg, Heissler, Wollmann, Camacho-Hubner, Hokken-Koelega, et al., 2017; Junli Zhu & Xuejun Kong, 2017). GH was found not only to increase height, but also decrease body fat and improve cognition, motor, and mental function. With earlier initiation of GH treatment, better efficacy and prognostic benefit have been observed(Bakker, Lindberg, Heissler, Wollmann, Camacho-Hubner, & Hokken-Koelega, 2017). One study found probiotics *L. reuteri* could increase growth hormone level in mice(Varian et al., 2018), which reveals a potential mechanism by which probiotics can enhance height and treat PWS patients: promotion of endogenous growth hormone release. Our findings warrant further investigation into the biological mechanisms of probiotics, a promising intervention for PWS with better tolerance and convenience than GH replacement (Onubi et al., 2015).

We did not observe significant weight reduction within the intervention period, possibly due to the majority of our participants being less than five years old, an age range at which obesity is not yet a major problem. Interestingly, the microbiome composition changes we observed with the intervention of *B. lactis* have been previously linked to weight or adiposity reduction (Amat-Bou et al., 2020; Barz et al., 2019; Carreras et al., 2018; Huo et al., 2020; Mekkes et al., 2014; Pedret et al., 2019a; Uusitupa et al., 2020b), improve fasting insulin sensitivity (Amat-Bou et al., 2020) and inflammatory attenuation (Ibarra et al., 2018; Meng et al., 2017). Notably, we found a significant separation of the gut microbiome β-diversity between the probiotics and the placebo group after treatment. Baseline β-diversity has been directly correlated with long-term weight loss when adhering to a controlled diet (Grembi et al., 2020). Therefore, probiotics supplementation may have preventative effects or may facilitate diet-induced weight reduction.

After administration of BL-11, we also noted reduction in the abundance of several bacterial genera and species that have been implicated in the pathology of obesity and associated inflammation. Ruminococcaceae UCG-003, associated with VLDL and metabolic syndrome, has also been implicated in inflammatory bowel diseases (Hall et al., 2017; Vojinovic et al., 2019). Lachnospiraceae ND3007 has been linked to elevated cholesterol, signs of insulin resistance, and infant obesity(Liang et al., 2020; Tun et al., 2018; J.

Wang et al., 2020). Elevated *Streptococcus* has been associated with inflammatory GI disorders, maternal inflammation, bacteremia, and antibiotic use during pregnancy (Iakovlev et al., 2020; N. Li et al., 2019). *Rothia* was found to have a higher abundance in a gestational diabetic cohort than a healthy pregnant cohort (Crusell et al., 2018). The Comamonadaceae family is generally regarded as pathogenic in humans (Willems, 2013).

Conversely, *Bifidobacterium, Lactobacillus*, and *Prevotella* were each found to be considerably increased in the gut after BL-11 treatment. *Bifidobacterium*, the genus to which the interventional probiotic belongs, is widely regarded as beneficial to gut health and weight reduction (Alyousif et al., 2018; Barz et al., 2019; Carreras et al., 2018; Dimidi et al., 2019; Huo et al., 2020; Ibarra et al., 2018; S.-C. Li et al., 2019; Oliveira et al., 2017; Pedret et al., 2019a; Taipale et al., 2016; Uusitupa et al., 2020b). *Lactobacillus*, in addition to having protective effects against weight gain in humans, has been found to inhibit the activity of proinflammatory interleukins, which have been linked to obesity and poor obesity-related outcomes (Ayyanna et al., 2018; Cox et al., 2015; Rosing et al., 2017b). The effect of *Prevotella* in the gut microbiome remains uncertain, as evidence linking this genus to health benefit and disease have both been reported. Wang et al. (2019) reported that *Prevotella*-9 was found to be significantly decreased in both mice put on a high-fat diet and Zeng et al. (2018) reported the same in women with PCOS who were insulin-resistant (X. Wang et al., 2019; Zeng et al., 2019). Further, Park et al. (2013) reported an increased abundance of *Prevotella* in obesity improved mice and Kovatcheva-Datchary et al. (2015) reported dietary fiber-induced improvements in postprandial blood glucose and insulin were found to be positively associated with the abundance of *Prevotella* (Kovatcheva-Datchary et al., 2015; Parks et al., 2013). On the other hand, one study found that the Provetellaceae family had greater relative abundance in 3 obese patients, compared to 3 normal weight patients(Zhang et al., 2009). Another study, investigating fecal bacteria composition in HIV-positive patients, found that *Prevotella* was positively correlated with BMI, although most participants in this study had a BMI within the normal range (Pinto-Cardoso et al., 2017). The conflicting findings about *Prevotella* in gut health and obesity may indicate the importance of balancing the abundance of this genus within the microbiome.

Furthermore, by using predictive functional gene analysis, we found the enhancement of antioxidant production-related pathways that exert anti-inflammatory and anti-obesity effects. The gene encoding the ubiquinone biosynthesis protein (ubiB, k03688), responsible for the biosynthesis of ubiquinone (CoQ10), was found to have increased abundance following probiotics treatment. CoQ10 supplementation can be useful in the treatment of a variety of chronic cardiovascular, inflammatory, and obesity-related disease (Zozina et al., 2018). We also found an elevated abundance of genes encoding phytoene desaturase (EC: 1.3.99.29), phytoene desaturase (lycopene-forming), (EC: 1.3.99.31), and all-trans-zeta-carotene desaturase (EC: 1.3.99.26), which all contribute to the biosynthesis of carotenoids, previously found to have beneficial effects on obesity and obesity-associated pathologies(Mounien et al., 2019; Paes-Silva et al., 2019; Wiese et al., 2019). We also found downregulation of two enzymes, dimethylargininase (k01482) and acid phosphatase (phoN, k09474, EC:3.1.3.2), which have been linked to obesity development and elevated cholesterol and triglyceride levels in human patients (Arlouskaya et al., 2019; Bottini et al., 2002; Lång et al., 2011).

Taken together, the microbiome composition data and predictive functional gene analysis indicate that the diversity separation caused by BL-11 probiotics treatment favors protection against obesity and obesity-related pathology.

Although we did not find a significant change in psychological measurements (ASQ-3, ABC, SRS, and RRB), CGI-I showed significant overall improvement in the probiotics group after the treatment period compared with the placebo group ($P<0.05$).

Interestingly, we found that the RRB score was positively correlated with *Rothia* at the genus level ($P<0.005$). RRB is one of the core symptoms of ASD, which has been reported in as many as 25-40% of PWS cases (Bennett et al., 2015; Salehi et al., 2018). *Rothia*, in addition to being linked to diabetes (Crusell et al., 2018), has been reported to be more prevalent in children with ASD than typically-developing children (12.2-fold-change; FDR, $P<0.05$) (Forsyth et al., 2020). While the mechanism by which the BL-11 improved clinical impression of PWS patients is unknown, the correlation found between *Rothia* and RRB indicates that the BL-11 may be modulating signaling in the gut-brain axis. Further investigation of *Rothia* and other microbiome markers may reveal potent and feasible targets for neuropsychiatric therapies.

Our randomized trial showed that treatment with probiotic B. *Lactis* strain (BL-11) for 12 weeks significantly increased height, a novel finding with vital implications for early treatment in PWS. Probiotic treatment also improved overall clinical symptoms as indicated by CGI-I and altered microbiome composition and function to favor anti-obesity. There are some limitations to the study that deserve consideration. First, despite our adoption of proper recruitment and retention strategies, PWS participant enrollment and retention for this trial were challenging, the sample size was relatively small and limited further subgroup analysis. Second, although there was no statistical difference in clinical indices between the probiotics and placebo groups at baseline, the broad age range used in this study resulted in high subject population heterogeneity and potentially variable treatment efficacy. Third, assessment of fecal microbiome was not controlled for dietary habits, which may influence the microbial abundances at the individual level. Thus, future studies with larger sample sizes, improved control for environmental factors, and subgroup stratification are warranted. Due to the limitations of the study listed above, further studies are warranted to investigate the mechanism and efficacy of BL-11 probiotics treatment in PWS.

REFERENCES

1. Cassidy S B, Schwartz S, Miller J L, Driscoll D J. Prader-Willi syndrome. *Genet Med* (2012) 14:10-26. doi: 10.1038/gim.0b013e31822bead0
2. Cassidy S B, Forsythe M, Heeger S, Nicholls R D, Schork N, Benn P, Schwartz S. Comparison of phenotype between patients with Prader-Willi syndrome due to deletion 15q and uniparental disomy 15. *Am J Med Genet* (1997) 68:433-440. doi:10.1002/(sici)1096-8628 (19970211)68:4<433::aid-ajmg12>3.0.co; 2-t
3. Salehi P, Herzig L, Capone G, Lu A, Oron A P, Kim S. Comparison of Aberrant Behavior Checklist profiles across Prader-Willi syndrome, Down syndrome, and autism spectrum disorder. *Am J Med Genet A* (2018) 176:2751-2759. doi:10.1002/ajmg.a.40665
4. Olsson L M, Poitou C, Tremaroli V, Coupaye M, Aron-Wisnewsky J, Backhed F, Clement K, Caesar R. Gut microbiota of obese subjects with Prader-Willi syndrome is linked to metabolic health. *Gut* (2020) 69:1229-1238. doi:10.1136/gutjnl-2019-319322
5. Zhang C, Yin A, Li H, Wang R, Wu G, Shen J, Zhang M, Wang L, Hou Y, Ouyang H, et al. Dietary Modulation of Gut Microbiota Contributes to Alleviation of Both Genetic and Simple Obesity in Children. *Ebiomedicine* (2015) 2:968-984. doi:10.1016/j.ebiom.2015.07.007
6. Deng L, Wang R, Li H, Zhang C, Zhao L, Zhang M. miRNA-Gene Regulatory Network in Gnotobiotic Mice Stimulated by Dysbiotic Gut Microbiota Transplanted From a Genetically Obese Child. *Front Microbiol* (2019) 10:1517. doi:10.3389/fmicb.2019.01517
7. Ke X, Walker A, Haange S-B, Lagkouvardos I, Liu Y, Schmitt-Kopplin P, Bergen M von, Jehmlich N, He X, Clavel T, et al. Synbiotic-driven improvement of metabolic disturbances is associated with changes in the gut microbiome in diet-induced obese mice. *Mol Metab* (2019) 22:96-109. doi:10.1016/j.molmet.2019.01.012
8. Hibberd A A, Yde C C, Ziegler M L, Honoré AH, Saarinen M T, Lahtinen S, Stahl B, Jensen H M, Stenman L K. Probiotic or synbiotic alters the gut microbiota and metabolism in a randomised controlled trial of weight management in overweight adults. *Benef Microbes* (2019) 10:121-135. doi:10.3920/bm2018.0028
9. Vindegaard N, Speyer H, Nordentoft M, Rasmussen S, Benros M E. Gut microbial changes of patients with psychotic and affective disorders: A systematic review. *Schizophr Res* (2020) doi:10.1016/j.schres.2019.12.014
10. Kong X, Liu J, Cetinbas M, Sadreyev R, Koh M, Huang H, Adeseye A, He P, Zhu J, Russell H, et al. New and Preliminary Evidence on Altered Oral and Gut Microbiota in Individuals with Autism Spectrum Disorder (ASD): Implications for ASD Diagnosis and Subtyping Based on Microbial Biomarkers. *Nutrients* (2019) 11:2128. doi: 10.3390/nu11092128
11. Liu J, Wan G, Huang M, Agyapong G, Zou T, Zhang X, Liu Y-W, Song Y, Tsai Y-C, Kong X. Probiotic Therapy for Treating Behavioral and Gastrointestinal Symptoms in Autism Spectrum Disorder: A Systematic Review of Clinical Trials. *Curr Medical Sci* (2019) 39:173-184. doi:10.1007/s11596-019-2016-4
12. Dickerson F, Adamos M, Katsafanas E, Khushalani S, Origoni A, Savage C, Schweinfurth L, Stallings C, Sweeney K, Goga J, et al. Adjunctive probiotic microorganisms to prevent rehospitalization in patients with acute mania: A randomized controlled trial. *Bipolar Disord* (2018) 20:614-621. doi:10.1111/bdi.12652
13. Ventura M, Zink R. Rapid Identification, Differentiation, and Proposed New Taxonomic Classification of *Bifidobacterium lactis*. *Appl Environ Microb* (2002) 68:6429-6434. doi:10.1128/aem.68.12.6429-6434.2002
14. Huo Y, Lu X, Wang X, Wang X, Chen L, Guo H, Zhang M, Li Y. *Bifidobacterium animalis* subsp. *lactis* A6 Alleviates Obesity Associated with Promoting Mitochondrial Biogenesis and Function of Adipose Tissue in Mice. *Molecules* (2020) 25:1490. doi:10.3390/molecules25071490
15. Carreras N L, Martorell P, Chenoll E, Genovés S, Ramón D, Aleixandre A. Anti-obesity properties of the strain *Bifidobacterium animalis* subsp. *lactis* CECT 8145 in Zücker fatty rats. *Benef Microbes* (2018) 9:629-641. doi: 10.3920/bm2017.0141
16. Pedret A, Valls R M, Calderón-Pérez L, Llauradó E, Companys J, Pla-Pagà L, Moragas A, Martín-Luján F, Ortega Y, Giralt M, et al. Effects of daily consumption of the probiotic *Bifidobacterium animalis* subsp. *lactis* CECT 8145 on anthropometric adiposity biomarkers in abdominally obese subjects: a randomized controlled trial. *Int J Obesity* (2019) 43:1863-1868. doi:10.1038/s41366-018-0220-0
17. Barz M L, Daniel N, Varin T V, Naimi S, Demers-Mathieu V, Pilon G, Audy J, Laurin É, Roy D, Urdaci M C, et al. In vivo screening of multiple bacterial strains identifies *Lactobacillus rhamnosus* Lb102 and *Bifidobacterium animalis* ssp. *lactis* Bf141 as probiotics that improve metabolic disorders in a mouse model of obesity. *Faseb J* (2019) 33:4921-4935. doi:10.1096/fj.201801672r
18. Uusitupa H-M, Rasinkangas P, Lehtinen M J, Mäkelä SM, Airaksinen K, Anglenius H, Ouwehand A C, Maukonen J. *Bifidobacterium animalis* subsp. *lactis* 420 for Metabolic Health: Review of the Research. *Nutrients* (2020) 12:892. doi:10.3390/nu12040892
19. Mekkes M C, Weenen T C, Brummer R J, Claassen E. The development of probiotic treatment in obesity: a review. *Benef Microbes* (2014) 5:19-28. doi:10.3920/bm2012.0069
20. Ibarra A, Latreille-Barbier M, Donazzolo Y, Pelletier X, Ouwehand A C. Effects of 28-day *Bifidobacterium animalis* subsp. *lactis* HN019 supplementation on colonic transit time and gastrointestinal symptoms in adults with functional constipation: A double-blind, randomized, placebo-controlled, and dose-ranging trial. *Gut Microbes* (2017) 9:00-00. doi:10.1080/19490976.2017.1412908
21. Meng H, Ba Z, Lee Y, Peng J, Lin J, Fleming J A, Furumoto E J, Roberts R F, Kris-Etherton P M, Rogers C J. Consumption of *Bifidobacterium animalis* subsp. *lactis* BB-12 in yogurt reduced expression of TLR-2 on peripheral blood-derived monocytes and pro-inflammatory cytokine secretion in young adults. *Eur J Nutr* (2017) 56:649-661. doi:10.1007/s00394-015-1109-5
22. Amat-Bou et al. (2020) Effects of *Bifidobacerium animalis* subsp. *lactis* (BPL1) supplementation in children and adolescents with Prader-Willy Syndrome: a randomized crossover trial. *Nutrients* 2020, 12, 3123).
23. GROUP WMGRS, Onis M. WHO Child Growth Standards based on length/height, weight and age. *Acta Paediatr* (2006) 95:76-85. doi:10.1111/j.1651-2227.2006.tb02378.x
24. J S, D B, E T. Ages & Stages Questionnaires. (2009)
25. Aman M G, Singh N N, Stewart A W, Field C J. The aberrant behavior checklist: a behavior rating scale for the assessment of treatment effects. *Am J Ment Retard* (1985) 89:485-91.
26. J C, C G. Social Responsive Scale (SRS) Manual. (2005)
27. JE G. GARS-3: Gilliam Autism Rating Scale-Third Edition. (2014)
28. Bolyen E, Rideout J R, Dillon M R, Bokulich N A, Abnet C C, Al-Ghalith G A, Alexander H, Alm E J, Arumugam M, Asnicar F, et al. Reproducible, interactive, scalable and extensible microbiome data science using QIIME 2. *Nat Biotechnol* (2019) 37:852-857. doi:10.1038/s41587-019-0209-9
29. Amir A, McDonald D, Navas-Molina J A, Kopylova E, Morton J T, Xu Z Z, Kightley E P, Thompson L R, Hyde E R, Gonzalez A, et al. Deblur Rapidly Resolves Single-Nucleotide Community Sequence Patterns. *Msystems* (2017) 2:e00191-16. doi:10.1128/msystems.00191-16
30. Jiang L, Amir A, Morton J T, Heller R, Arias-Castro E, Knight R. Discrete False-Discovery Rate Improves Identification of Differentially Abundant Microbes. *Msystems* (2017) 2:e00092-17. doi:10.1128/msystems.00092-17
31. Douglas G M, Maffei V J, Zaneveld J, Yurgel S N, Brown J R, Taylor C M, Huttenhower C, Langille M G I.

PICRUSt2: An improved and customizable approach for metagenome inference. *Biorxiv* (2020)672295. doi:10.1101/672295
32. Czech L, Barbera P, Stamatakis A. Genesis and Gappa: processing, analyzing and visualizing phylogenetic (placement) data. *Bioinformatics* (2020) 36:3263-3265. doi:10.1093/bioinformatics/btaa070
33. Xu Z Z, Amir A, Sanders J, Zhu Q, Morton J T, Bletz M C, Tripathi A, Huang S, McDonald D,
Jiang L, et al. Calour: an Interactive, Microbe-Centric Analysis Tool. *Msystems* (2019) 4: doi:10.1128/msystems.00269-18
34. Onubi O J, Poobalan A S, Dineen B, Marais D, McNeill G. Effects of probiotics on child growth: a systematic review. *J Heal Popul Nutrition* (2015) 34:8. doi:10.1186/s41043-015-0010-4
35. Zhu J, Kong X. Current Treatments of Prader-Willi Syndrome: A Systematic Review. *N A J Med Sci* (2018) 10 (4):156-163. doi:10.7156/najms.2017.1004156
36. Bakker N E, Lindberg A, Heissler J, Wollmann H A, Camacho-Hübner C, Hokken-Koelega A C, Committee K S. Growth Hormone Treatment in Children With Prader-Willi Syndrome: Three Years of Longitudinal Data in Prepubertal Children and Adult Height Data From the KIGS Database. *J Clin Endocrinol Metabolism* (2017) 102:1702-1711. doi:10.1210/jc.2016-2962
37. Varian B J, Gourishetti S, Poutahidis T, Lakritz J R, Levkovich T, Kwok C, Teliousis K, Ibrahim Y M, Mirabal S, Erdman S E. Correction: Beneficial bacteria inhibit cachexia. *Oncotarget* (2018) 9:29536-29536. doi:10.18632/oncotarget.25750
38. Grembi J A, Nguyen L H, Haggerty T D, Gardner C D, Holmes S P, Parsonnet J. Gut microbiota plasticity is correlated with sustained weight loss on a low-carb or low-fat dietary intervention. *Sci Rep-uk* (2020) 10:1405. doi:10.1038/s41598-020-58000-y
39. Vojinovic D, Radjabzadeh D, Kurilshikov A, Amin N, Wijmenga C, Franke L, Ikram M A, Uitterlinden A G, Zhernakova A, Fu J, et al. Relationship between gut microbiota and circulating metabolites in population-based cohorts. *Nat Commun* (2019) 10:5813. doi:10.1038/s41467-019-13721-1
40. Hall A B, Yassour M, Sauk J, Garner A, Jiang X, Arthur T, Lagoudas G K, Vatanen T, Fornelos N, Wilson R, et al. A novel *Ruminococcus* gnavus clade enriched in inflammatory bowel disease patients. *Genome Med* (2017) 9:103. doi:10.1186/s13073-017-0490-5
41. Wang J, Xiong K, Zhao S, Zhang C, Zhang J, Xu L, Ma A. Long-Term Effects of Multi-Drug-Resistant Tuberculosis Treatment on Gut Microbiota and Its Health Consequences. *Front Microbiol* (2020) 11:53. doi:10.3389/fmicb.2020.00053
42. Liang Y, Ming Q, Liang J, Zhang Y, Zhang H, Shen T. Gut microbiota dysbiosis in Polycystic ovary syndrome (PCOS): association with obesity—A preliminary report. *Can J Physiol Pharm* (2019) 0: doi:10.1139/cjpp-2019-0413
43. Tun H M, Bridgman S L, Chari R, Field C J, Guttman D S, Becker A B, Mandhane P J, Turvey S E, Subbarao P, Sears M R, et al. Roles of Birth Mode and Infant Gut Microbiota in Intergenerational Transmission of Overweight and Obesity From Mother to Offspring. *Jama Pediatr* (2018) 172:368. doi:10.1001/jamapediatrics.2017.5535
44. Iakovlev A A, Volkov A, Bashtovaya O, Shcherbakova I, Ghazudin T, Leonova G, Tarasova G. P081 The structure of the proteomic profile and gut microbiota in patients with primary immunodeficiency, common variable immunodeficiency and inflammatory bowel disease. *J Crohn's Colitis* (2020) 14:S175-S176. doi:10.1093/ecco-jcc/jjz203.210
45. Li N, Yang J, Zhang J, Liang C, Wang Y, Chen B, Zhao C, Wang J, Zhang G, Zhao D, et al. Correlation of Gut Microbiome Between ASD Children and Mothers and Potential Biomarkers for Risk Assessment. *Genom Proteom Bioinform* (2019) 17:26-38. doi:10.1016/j.gpb.2019.01.002
46. Crusell M K W, Hansen T H, Nielsen T, Allin K H, Rühlemann MC, Damm P, Vestergaard H, Rørbye C, Jørgensen NR, Christiansen O B, et al. Gestational diabetes is associated with change in the gut microbiota composition in third trimester of pregnancy and postpartum. *Microbiome* (2018) 6:89. doi:10.1186/s40168-018-0472-x
47. Willems A. The Prokaryotes, Alphaproteobacteria and Betaproteobacteria. (2014)777-851. doi:10.1007/978-3-642-30197-1_238
48. Dimidi E, Zdanaviciene A, Christodoulides S, Taheri S, Louis P, Duncan P I, Emami N, Crabbé R, Castro C A D, McLean P, et al. Randomised clinical trial: *Bifidobacterium lactis* NCC2818 probiotic vs placebo, and impact on gut transit time, symptoms, and gut microbiology in chronic constipation. *Aliment Pharm Therap* (2019) 49:251-264. doi:10.1111/apt.15073
49. Alyousif Z, Miller J L, Sandoval M Y, MacPherson C W, Nagulesapillai V, Dahl W J. The effects of *Bifidobacterium animalis* ssp. *lactis* B94 on gastrointestinal wellness in adults with Prader-Willi syndrome: study protocol for a randomized controlled trial. *Trials* (2018) 19:256. doi:10.1186/s13063-018-2648-x
50. Oliveira L F F, Salvador S L, Silva P H F, Furlaneto F A C, Figueiredo L, Casarin R, Ervolino E, Palioto D B, Souza S L S, Taba M, et al. Benefits of *Bifidobacterium animalis* subsp. *lactis* Probiotic in Experimental Periodontitis. *J Periodontol* (2017) 88:197-208. doi:10.1902/jop.2016.160217
51. Taipale T J, Pienihakkinen K, Isolauri E, Jokela J T, Soderling E M. *Bifidobacterium animalis* subsp. *lactis* BB-12 in reducing the risk of infections in early childhood. *Pediatr Res* (2016) 79:65-69. doi:10.1038/pr.2015.174
52. Li S-C, Hsu W-F, Chang J-S, Shih C-K. Combination of *Lactobacillus acidophilus* and *Bifidobacterium animalis* subsp. *lactis* Shows a Stronger Anti-Inflammatory Effect than Individual Strains in HT-29 Cells. *Nutrients* (2019) 11:969. doi:10.3390/nu11050969
53. Rosing J A, Walker K C, Jensen B A H, Heitmann B L. Oral *Lactobacillus* Counts Predict Weight Gain Susceptibility: A 6-Year Follow-Up Study. *Obesity Facts* (2017) 10:473-482. doi:10.1159/000478095
54. Ayyanna R, Ankaiah D, Arul V. Anti-inflammatory and Antioxidant Properties of Probiotic Bacterium *Lactobacillus* mucosae AN1 and *Lactobacillus fermentum* SNR1 in Wistar Albino Rats. *Front Microbiol* (2018) 9:3063. doi:10.3389/fmicb.2018.03063
55. Cox A J, West N P, Cripps A W. Obesity, inflammation, and the gut microbiota. *Lancet Diabetes Endocrinol* (2015) 3:207-215. doi:10.1016/s2213-8587(14)70134-2
56. Wang X, Chen D, Li Y, Zhao S, Chen C, Ning D. Alleviating effects of walnut green husk extract on disorders of lipid levels and gut bacteria flora in high fat diet-induced obesity rats. *J Funct Food* (2019) 52:576-586. doi:10.1016/j.jff.2018.11.022

57. Zeng B, Lai Z, Sun L, Zhang Z, Yang J, Li Z, Lin J, Zhang Z. Structural and functional profiles of the gut microbial community in polycystic ovary syndrome with insulin resistance (IR-PCOS): a pilot study. *Res Microbiol* (2018) 170:43-52. doi:10.1016/j.resmic.2018.09.002
58. Parks B W, Nam E, Org E, Kostem E, Norheim F, Hui S T, Pan C, Civelek M, Rau C D, Bennett B J, et al. Genetic Control of Obesity and Gut Microbiota Composition in Response to High-Fat, High-Sucrose Diet in Mice. *Cell Metab* (2013) 17:141-152. doi:10.1016/j.cmet.2012.12.007
59. Kovatcheva-Datchary P, Nilsson A, Akrami R, Lee Y S, De Vadder F, Arora T, Hallen A, Martens E, Björck I, Backhed F. Dietary Fiber-Induced Improvement in Glucose Metabolism Is Associated with Increased Abundance of Prevotella. *Cell Metab* (2015) 22:971-982. doi: 10.1016/j.cmet.2015.10.001
60. Zhang H, DiBaise J K, Zuccolo A, Kudrna D, Braidotti M, Yu Y, Parameswaran P, Crowell M D, Wing R, Rittmann B E, et al. Human gut microbiota in obesity and after gastric bypass. *Proc National Acad Sci* (2009) 106: 2365-2370. doi:10.1073/pnas.0812600106
61. Pinto-Cardoso S, Lozupone C, Briceño O, Alva-Hernández S, Téllez N, Adriana A, Murakami-Ogasawara A, Reyes-Terán G. Fecal Bacterial Communities in treated HIV infected individuals on two antiretroviral regimens. *Sci Rep-uk* (2017) 7:43741. doi:10.1038/srep43741
62. Zozina V I, Covantev S, Goroshko O A, Krasnykh L M, Kukes V G. Coenzyme Q10 in Cardiovascular and Metabolic Diseases: Current State of the Problem. *Curr Cardiol Rev* (2018) 14:164-174. doi:10.2174/1573403x14666180416115428
63. Paes-Silva R P, Gadelha PCFP, Lemos M da CC de, Castro CMMB de, Arruda I K G de, Diniz A da S. Adiposity, inflammation and fat-soluble vitamins in adolescents. *J Pediat* (2018) 95:575-583. doi:10.1016/j.jped.2018.05.008
64. Mounien L, Tourniaire F, Landrier J-F. Anti-Obesity Effect of Carotenoids: Direct Impact on Adipose Tissue and Adipose Tissue-Driven Indirect Effects. *Nutrients* (2019) 11:1562. doi:10.3390/nu11071562
65. Wiese M, Bashmakov Y, Chalyk N, Nielsen D S, Krych L, Kot W, Klochkov V, Pristensky D, Bandaletova T, Chernyshova M, et al. Prebiotic Effect of Lycopene and Dark Chocolate on Gut Microbiome with Systemic Changes in Liver Metabolism, Skeletal Muscles and Skin in Moderately Obese Persons. *Biomed Res Int* (2019) 2019:1-15. doi:10.1155/2019/4625279
66. Arlouskaya Y, Sawicka A, Glowala M, Giebułtowicz J, Korytowska N, Tałałaj M, Nowicka G, Wrzosek M. Asymmetric Dimethylarginine (ADMA) and Symmetric Dimethylarginine (SDMA) Concentrations in Patients with Obesity and the Risk of Obstructive Sleep Apnea (OSA). *J Clin Medicine* (2019) 8:897. doi:10.3390/jcm8060897
67. Lång P, Zakaroff-Girard A, Wåhlén K, Andersson J, Olsson T, Bambace C, Jocken J, Bouloumié A, Andersson G, Amer P. Expression and secretion of the novel adipokine tartrate-resistant acid phosphatase from adipose tissues of obese and lean women. *Int J Obesity* (2011) 35:1502-1510. doi:10.1038/ijo.2011.17
68. Bottini N, MacMurray J, Peters W, Rostamkhani M, Comings D E. Association of the acid phosphatase (ACP1) gene with triglyceride levels in obese women. *Mol Genet Metab* (2002) 77:226-229. doi:10.1016/s1096-7192(02)00120-8
69. Bennett J A, Germani T, Haqq A M, Zwaigenbaum L. Autism spectrum disorder in Prader-Willi syndrome: A systematic review. *Am J Med Genet A* (2015) 167:2936-2944. doi:10.1002/ajmg.a.37286
70. Forsyth A, Raslan K, Lyashenko C, Bona S, Snow M, Khor B, Herrman E, Ortiz S, Choi D, Maier T, et al. Children with Autism Spectrum Disorder: Pilot Studies Examining the Salivary Microbiome and Implications for Gut Metabolism and Social Behavior. *Hum Microbiome J* (2019) 15:100066. doi:10.1016/j.humic.2019.100066
71. Quigley E M M. Gut bacteria in health and disease. *Gastroenterology Hepatology* (2013) 9:560-9

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

The invention claimed is:

1. A method of treating a pediatric subject diagnosed with or at risk of Prader-Willi syndrome (PWS), the method comprising: administering to the subject an effective amount of a probiotic comprising *Lactobacillus reuteri* (*L. reuteri*) strain LR-99, deposited at the China General Microbiological Culture Collection Center under CGMCC No. 21577, wherein the treatment comprises administering the effective dose of the probiotic for at least about 3 weeks.

2. The method of claim 1, wherein the probiotic further comprises an additional *Lactobacillus* sp., a *Saccharomyces* sp., a *Bacillus* sp., and/or *Eubacterium hallii.*

3. The method of claim 1, wherein the subject is suffering from one or more of the following symptoms or conditions: obesity, short stature, social deficits, fine motor abnormalities, developmental delay, and abnormal behavioral characteristics; wherein after treatment, the subject's symptoms or conditions are improved, as compared to before treatment.

4. The method of claim 3, wherein the developmental delay comprises one or more of communication, gross motor control, fine motor control, problem-solving, and personal-social interaction.

5. The method of claim 3 wherein the abnormal behavioral characteristics comprise one or more of restrictive, repetitive behaviors (RRB), aberrant social interaction (SI), aberrant social communication (SC), aberrant emotional responses (ER), aberrant cognitive style (CS), and maladaptive speech (MS).

6. The method of claim 3, wherein the subject's body-mass index (BMI) after treatment is lower than the subject's BMI before treatment.

7. The method of claim 4, wherein the subject's Ages and Stages Questionnaires, 3rd Edition (ASQ-3) score is statistically improved for one or more of communication, gross motor function, fine motor function, problem-solving, and personal-social interaction after treatment as compared to the subject's ASQ-3 score before treatment.

8. The method of claim 5, wherein the subject's Gilliam Autism Rating Scale, Third Edition (GARS-3) score is statistically improved for one or more of RRB, SI, SC, ER, CS and MS after treatment as compared to the subject's GARS-3 score before treatment.

9. The method of claim 1, wherein the treatment comprises administering an effective dose of the probiotic once per day, twice per day, three times per day, or four times per day.

10. The method of claim 1, wherein the treatment comprises administering an effective dose of the probiotic for at least about 4 weeks, 5 weeks, 6 weeks, 7 weeks, 8 weeks, 9 weeks, 10 weeks, 11 weeks, or at least about 12 weeks.

11. The method of claim 1, wherein the effective amount comprises about $1\times10^5$ to about $1\times10^{15}$, about $1\times10^6$ to about $1\times10^{14}$, about $1\times10^7$ to about $1\times10^{13}$, about $1\times10^8$ to about $1\times10^{12}$, about $1\times10^9$ to about $1\times10^{11}$, about $1\times10^{10}$ to about $9\times10^{10}$, or about $3\times10^{10}$ colony forming units (CFU) of probiotic.

12. The method of claim 1, wherein the subject is administered one or more additional therapeutics.

13. The method of claim 1, wherein the probiotic is administered twice per day at a dose of about $3\times10^{10}$ CFU for 12 weeks, and wherein after treatment, the subject exhibits a statistically relevant improvement in one or more of BMI, fine motor function, and problem solving skills as measured by ASQ-3 testing.

14. The method of claim 1, wherein the subject's microbiome composition is different after the treatment as compared to before the treatment.

15. The method of claim 14, wherein the microbiome difference comprises a decrease in one or more of *Escherichia-Shigella, Porphyromonas*, and *Ruminococcus torques.*

16. The method of claim 14, wherein the microbiome difference comprises an increase in one or more of *Bifidobacterium, Lactobacillus, Faecalibacteria, Roseburia*, and *Alistipes.*

* * * * *